US011639908B2

(12) United States Patent
Klein et al.

(10) Patent No.: US 11,639,908 B2
(45) Date of Patent: May 2, 2023

(54) SYSTEM AND METHOD FOR SAMPLE PREPARATION IN GMR-BASED DETECTION OF BIOMARKERS

(71) Applicant: ZEPTO LIFE TECHNOLOGY, INC., St. Paul, MN (US)

(72) Inventors: Todd Michael Klein, Wayzata, MN (US); Keping Song, Lauderdale, MN (US); Minggan Li, St. Paul, MN (US); Chad Brian Rheault, Newport, MN (US); Wei Wang, St. Paul, MN (US); Gemma Roselle Mendonsa, Edina, MN (US)

(73) Assignee: ZEPTO LIFE TECHNOLOGY, INC., St. Paul, MN (US)

( * ) Notice: Subject to any disclaimer, the term of this patent is extended or adjusted under 35 U.S.C. 154(b) by 77 days.

(21) Appl. No.: 16/768,107

(22) PCT Filed: Jul. 26, 2019

(86) PCT No.: PCT/US2019/043753
§ 371 (c)(1),
(2) Date: May 29, 2020

(87) PCT Pub. No.: WO2020/023916
PCT Pub. Date: Jan. 30, 2020

(65) Prior Publication Data
US 2021/0370289 A1    Dec. 2, 2021

Related U.S. Application Data

(60) Provisional application No. 62/711,396, filed on Jul. 27, 2018.

(51) Int. Cl.
*G01N 27/12* (2006.01)
*G01N 33/18* (2006.01)
(Continued)

(52) U.S. Cl.
CPC .......... *G01N 27/12* (2013.01); *B01L 3/50273* (2013.01); *B01L 3/502715* (2013.01);
(Continued)

(58) Field of Classification Search
None
See application file for complete search history.

(56) References Cited

U.S. PATENT DOCUMENTS 5,646,001 A    7/1997    Terstappen et al.
6,437,563 B1   8/2002    Simmonds et al.
(Continued)

FOREIGN PATENT DOCUMENTS

EP    3324189 A1    5/2018
JP    2008522151 A  6/2008
(Continued)

OTHER PUBLICATIONS

International Search Report and Written Opinion dated Nov. 13, 2019 in International Application PCT/US2019/043753.
(Continued)

*Primary Examiner* — Lore R Jarrett
(74) *Attorney, Agent, or Firm* — Venable LLP

(57) ABSTRACT

A cartridge assembly, and method of using the same, is provided. The assembly includes a sample processing card and a substrate attached thereto. The card has an injection port for receiving a test sample; at least one metering chamber; a mixing material source for introducing mixing material(s) to the metering chamber; fluid communication channels fluidly connecting the injection port and the mixing material source to the metering chamber; and at least one output port for delivering the test sample to a sensor (e.g., GMR sensor). The substrate has associated therewith: the sensor for sensing analytes in the test sample; electrical contact portions for an electrical connection with a reader
(Continued)

unit; and a memory chip. The assembly further includes a pneumatic interface with port(s) and corresponding communication channel(s) fluidly connected to card. The interface connects with an off-board pneumatic system and enables application of positive and negative pressurized fluid to the card to move the test sample and one or more mixing materials therein and to the sensor.

20 Claims, 53 Drawing Sheets

(51) Int. Cl.
    *G01N 33/487* (2006.01)
    *G01N 33/49* (2006.01)
    *G01N 33/543* (2006.01)
    *B01L 3/00* (2006.01)
    *G01N 27/74* (2006.01)
    *G01N 33/493* (2006.01)
    *G01R 33/09* (2006.01)
    *G01R 33/12* (2006.01)

(52) U.S. Cl.
    CPC .............. *B01L 3/567* (2013.01); *G01N 27/74* (2013.01); *G01N 27/745* (2013.01); *G01N 33/1813* (2013.01); *G01N 33/48707* (2013.01); *G01N 33/49* (2013.01); *G01N 33/493* (2013.01); *G01N 33/54306* (2013.01); *G01R 33/093* (2013.01); *G01R 33/1269* (2013.01); *G01R 33/1276* (2013.01); *B01L 2200/026* (2013.01); *B01L 2200/027* (2013.01); *B01L 2200/04* (2013.01); *B01L 2200/0684* (2013.01); *B01L 2200/14* (2013.01); *B01L 2200/16* (2013.01); *B01L 2300/025* (2013.01); *B01L 2300/0663* (2013.01); *B01L 2300/0681* (2013.01); *B01L 2300/0816* (2013.01); *B01L 2300/0819* (2013.01); *B01L 2300/0883* (2013.01); *B01L 2300/0887* (2013.01); *B01L 2300/123* (2013.01); *B01L 2300/14* (2013.01); *B01L 2400/043* (2013.01); *B01L 2400/0487* (2013.01); *B01L 2400/06* (2013.01)

(56) References Cited

U.S. PATENT DOCUMENTS

| | | |
|---|---|---|
| 2008/0129286 A1 | 6/2008 | Kahlman et al. |
| 2008/0246471 A1 | 10/2008 | Kahlman et al. |
| 2008/0278156 A1 | 11/2008 | De Boer |
| 2008/0309329 A1 | 12/2008 | Kahlman et al. |
| 2009/0066318 A1 | 3/2009 | Kahlman et al. |
| 2009/0184706 A1 | 7/2009 | Duric et al. |
| 2010/0259250 A1 | 10/2010 | Kahlman |
| 2010/0267169 A1 | 10/2010 | Hajimiri et al. |
| 2012/0115214 A1 | 5/2012 | Battrell et al. |
| 2013/0130262 A1 | 5/2013 | Battrell et al. |
| 2013/0331298 A1 | 12/2013 | Rea |
| 2013/0343966 A1 | 12/2013 | Medoro et al. |
| 2014/0178900 A1 | 6/2014 | Jung et al. |
| 2014/0292318 A1 | 10/2014 | Wang et al. |
| 2015/0197784 A1 | 7/2015 | Williams et al. |
| 2016/0011182 A1 | 1/2016 | Qiu |
| 2016/0193603 A1 | 7/2016 | Battrell et al. |
| 2016/0209405 A1 | 7/2016 | Wang et al. |
| 2017/0097337 A1 | 4/2017 | Shultz et al. |
| 2017/0113221 A1 | 4/2017 | Hoffman et al. |
| 2017/0260567 A1 | 9/2017 | Selden et al. |
| 2017/0312751 A1 | 11/2017 | Glezer |
| 2018/0021783 A1 | 1/2018 | Arlett et al. |
| 2018/0067094 A1 | 3/2018 | Sinha et al. |
| 2018/0299407 A1 | 10/2018 | Haratani et al. |

FOREIGN PATENT DOCUMENTS

| | | |
|---|---|---|
| JP | 2009511860 A | 3/2009 |
| JP | 2009511895 A | 3/2009 |
| JP | 2009530602 A | 8/2009 |
| JP | 2009-236933 A | 10/2009 |
| JP | 2009-249512 A | 10/2009 |
| JP | 2009-250926 A | 10/2009 |
| JP | 2009539098 A | 11/2009 |
| JP | 2010500547 A | 1/2010 |
| JP | 2011-221017 A | 11/2011 |
| JP | 2012-516455 A | 7/2012 |
| JP | 2013-518289 A | 5/2013 |
| JP | 2016-509206 A | 3/2016 |
| JP | 2016-534333 A | 11/2016 |
| JP | 2017-520239 A | 7/2017 |
| JP | 2018507403 A | 3/2018 |
| JP | WO2017082227 A1 | 8/2018 |
| KR | 1020160080112 A | 7/2016 |
| WO | 2006059270 A1 | 6/2006 |
| WO | 2007042959 A1 | 4/2007 |
| WO | 2007092909 A2 | 8/2007 |
| WO | 2008047533 A1 | 4/2008 |
| WO | 2008101196 A1 | 8/2008 |
| WO | 2009024922 A2 | 2/2009 |
| WO | 2012085884 | 6/2012 |
| WO | 2016124907 A1 | 8/2016 |
| WO | 2018053501 A1 | 3/2018 |
| WO | 2018057647 A1 | 3/2018 |

OTHER PUBLICATIONS

International Search Report and Written Opinion dated May 8, 2019 in International Application PCT/US2019/021837.
International Preliminary Report on Patentability dated Sep. 22, 2020 in International Application PCT/US2019/021837.
Extended European Search Report dated Apr. 21, 2021 in European Application 19816193.7.
Office Action dated Apr. 27, 2021 in Japanese Application 2019-560705.
Office Action dated May 18, 2021 in Japanese Application 2019-560698.
Notice of Allowance dated May 18, 2021 in Japanese Application 2019-560695.
International Search Report and Written Opinion dated Nov. 15, 2019 in International Application PCT/US2019/043766.
International Preliminary Report on Patentability dated Feb. 11, 2021 in International Application PCT/US2019/043766.
International Preliminary Report on Patentability dated Feb. 11, 2021 in International Application PCT/US2019/043753.
International Search Report and Written Opinion dated Nov. 13, 2019 in International Application PCT/US2019/043720.
International Preliminary Report on Patentability dated Feb. 11, 2021 in International Application PCT/US2019/043720.
International Search Report and Written Opinion dated Nov. 13, 2019 in International Application PCT/US2019/043791.
International Preliminary Report on Patentability dated Feb. 11, 2021 in International Application PCT/US2019/043791.
Office Action dated Feb. 2, 2021 in Japanese Application 2019-560695.
Office Action dated Feb. 2, 2021 in Japanese Application 2019-560691.
Extended European Search Report dated Mar. 15, 2021 in European Application 19816192.9.
Office Action dated Feb. 23, 2022 in Canadian Patent Application No. 3,106,680.
Supplementary European Search Report dated Jan. 5, 2022 in EP Application No. 19816194.5.
Teh et al: "Highly sensitive and selective detection of Pb 2+ ions using a novel and simple DNAzyme-based quartz crystal microbalance with dissipation biosensor", Analyst, vol. 139, No. 20, Jul. 18, 2014, pp. 5170-5175.
Han et al: "CMOS Integrated DNA Microarray Based on GMR Sensors", Electron Devices Meeting, 2006. IEDM '06. International, IEEE, PI, Dec. 2006, pp. 1-4.

(56) References Cited

OTHER PUBLICATIONS

Han et al: "Magnetic Nanotechnology for Biodetection", Journal of the Association for Laboratory Automation, Elsevier, vol. 15, No. 2, Apr. 2010, pp. 93-98.
Yu et al: "Giant Magnetoresistive Biosensors for Molecular Diagnosis: Surface Chemistry and Assay Development", SPIE, vol. 7035, Aug. 2008, pp. 1-9.
Huo et al: "A Novel High-Sensitivity Cardiac Multibiomarker Detection System Based on Microfluidic Chip and GMR Sensors", IEEE Transactions on Magnetics, vol. 51, No. 11, Nov. 2015, pp. 1-4.
Wu et al: "Comparison of Hydroxylated Print Additives on Antibody Microarray Performance", Journal of Proteome Research, vol. 5, No. ii, Oct. 19, 2006, pp. 2956-2965.
Chu et al: "Bioconjugated Magnetic Nanoparticles for the Detection of Bacteria", Journal of Biomedical Nanotechnology, American Scientific Publishers, US, vol. 9, No. 12, Dec. 2013, pp. 1951-1961.
Gaster et al: "Matrix-insensitive protein assays push the limits of biosensors in medicine", Nature Medicine, Oct. 11, 2009, pp. 1-7.
McGhee et al: "DNAzyme sensors for detection of metal ions in the environment and imaging them in living cells", Current Opinion in Biotechnology, London, GB, vol. 45, Apr. 28, 2017, pp. 191-2001.
Wang et al: "Surface Modification for Protein and DNA Immobilization onto GMR Biosensor", IEEE Transactions on Magnetics, vol. 49, No. 1, Jan. 2013, pp. 296-299.
Huo et al: "A novel high-sensitivity cardiac multi-biomarkers detecting system based on microfluidic chip and GMR sensor", 2015 IEEE Magnetics Conference (INTERMAG), IEEE, 2015, p. 1.
Office Action dated Mar. 18, 2022 in Canadian Patent Application No. 3,106,320.
Han et al., "A Novel Zero-Drift Detection Method for Highly Sensitive GMR Biochips", IEEE Transactions on Magnetics, IEEE, USA, vol. 42, No. 10, Oct. 1, 2006, pp. 3560-3562.
Office Action dated Oct. 4, 2022 in Japanese Patent Application No. 2021-143806.
Extended European Search Report dated Dec. 5, 2022 in EP Application No. 22182712.4.

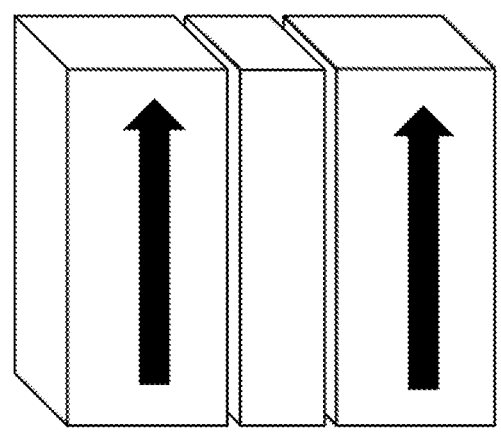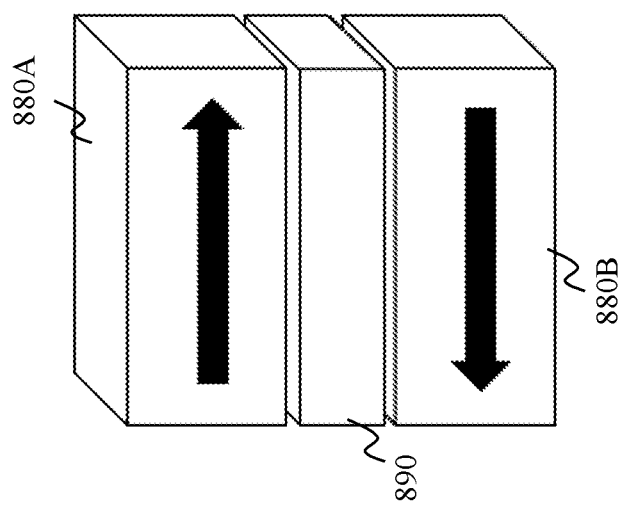
Fig. 2F

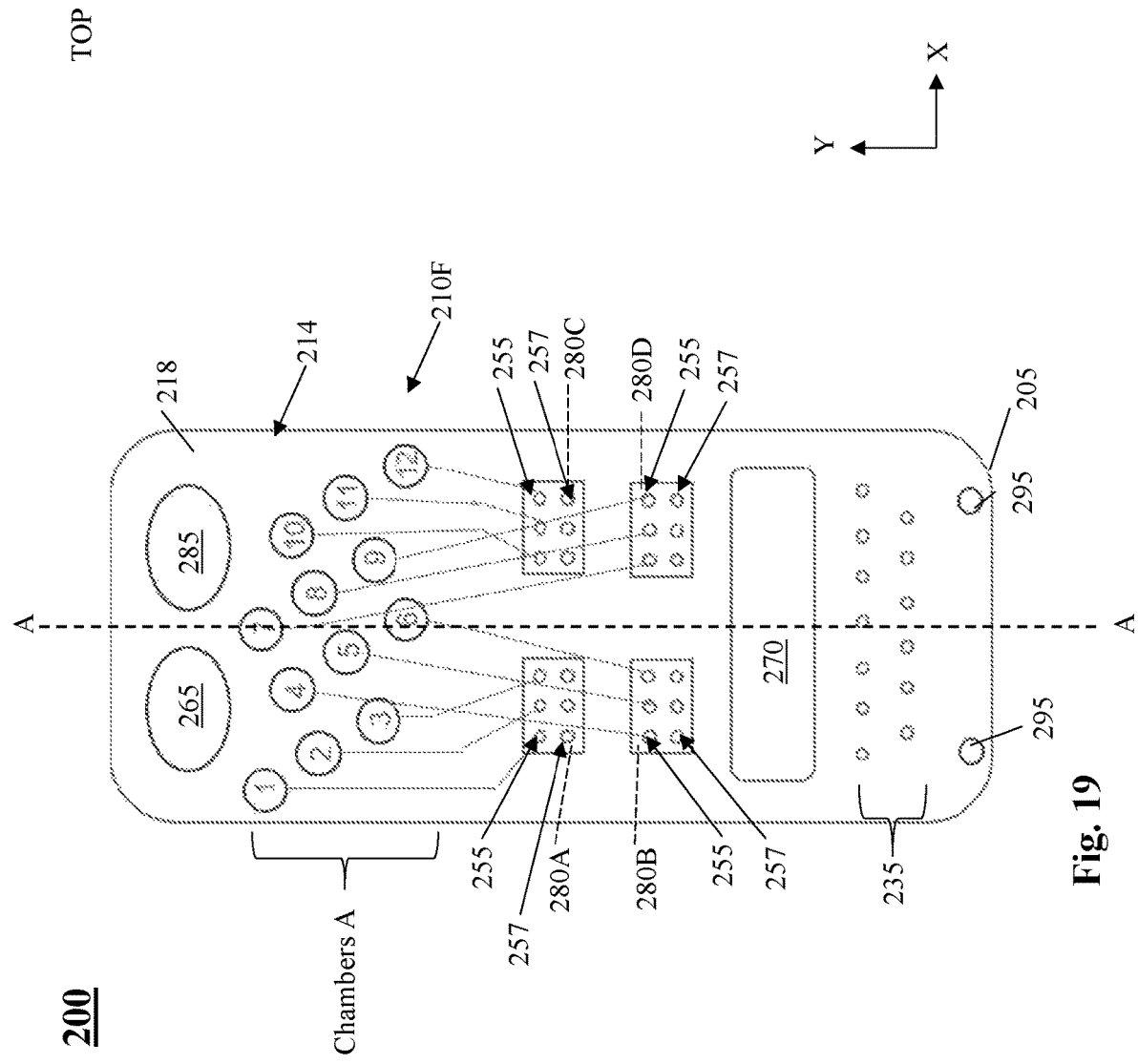

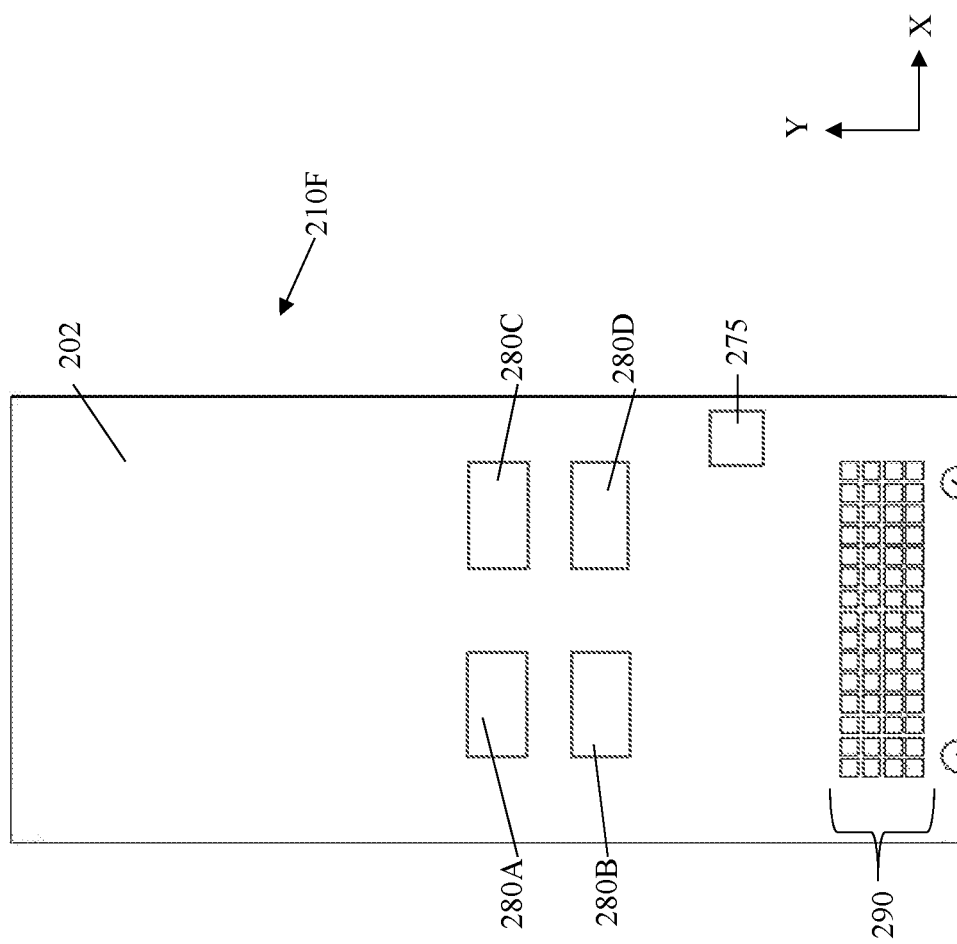

(Cartridge reader flowchart)

SYSTEM AND METHOD FOR SAMPLE PREPARATION IN GMR-BASED DETECTION OF BIOMARKERS

CROSS REFERENCE TO RELATED APPLICATIONS

This application a national stage application, filed under 35 U.S.C. § 371, of International Application No. PCT/US2019/043753, filed on Jul. 26, 2019, which claims priority to U.S. Provisional Patent Application No. 62/711,396, filed Jul. 27, 2018, both of which are incorporated herein by reference in their entireties.

BACKGROUND

Field

The present disclosure is generally related to a system for the detection of analytes. In particular, the present invention relates to a mobile system including a unit and a cartridge assembly that can be used for the detection of various analytes such as metal, biomarkers, and the like.

Description of Related Art

Generally, it is common to use a card to test for biomarker(s), metal, etc. in a blood sample. Adding a blood sample to known cards generally relies simply on lateral flow of the blood sample into the card before a reading is performed. Also, current assay systems in the medical market generally rely on capillary separation of a whole blood sample, which generally limits detection methodology to optical analysis or visual testing.

SUMMARY

Embodiments herein relate to devices for detection of analytes in a sample with magnetoresistive sensor technologies. For explanatory purposes, in accordance with embodiments, the devices, systems, and features are described with respect to utilizing a giant magnetoresistance (GMR) sensor platform.

It is an aspect of this disclosure to provide a cartridge assembly for preparing a test sample and sensing analytes therein using a sensor. The cartridge assembly includes: a sample processing card having: an injection port for receiving the test sample within a body of the card; at least one metering chamber for receiving the test sample; a mixing material source for introducing one or more mixing materials to the at least one metering chamber; fluid communication channels fluidly connecting the injection port and the mixing material source to the at least one metering chamber; and at least one output port fluidly connected to the at least one metering chamber for delivering the test sample and the one or more mixing materials to the sensor. The cartridge assembly also includes a substrate attached to the sample processing card. The substrate has associated therewith: the sensor for sensing analytes in the test sample, the sensor being configured to receive the test sample and the one or more mixing materials via the at least one output port; electrical contact portions configured to establish an electrical connection with the reader unit; and a memory chip for storing information related to processing of the test sample within the sample processing card. The cartridge assembly further includes a pneumatic interface comprising at least one pneumatic control port and corresponding communication channel fluidly connected to the at least one metering chamber, the pneumatic interface configured for connection to an off-board pneumatic system of a reader unit, the pneumatic interface configured to enable application of positive and negative pressurized fluid to the sample processing card to move the test sample and one or more mixing materials therein. The memory chip may store a pneumatic system protocol that includes steps and settings for selectively applying pressure to the pneumatic interface and thus delivering at least the test sample from the sample processing card to the sensor.

Another aspect provides a method of using the cartridge assembly described above, including injecting the test sample into the injection port; establishing the electrical connection with the reader unit; and selectively applying pressurized air to the pneumatic interface using the off-board pneumatic system to move the test sample and the one or more mixing materials within the communication channels and to the sensor.

Other aspects, features, and advantages of the present disclosure will become apparent from the following detailed description, the accompanying drawings, and the appended claims.

BRIEF DESCRIPTION OF THE DRAWINGS

Various embodiments of the present disclosure will be described herein below with reference to the Figures wherein:

FIG. 2F schematically illustrates a basic structure and principle of GMR sensors.

FIGS. 19 and 20 illustrate a top and a bottom, respectively, of another exemplary assay sample processing card configured for use in a cartridge assembly, that determines relative kinetics for antibodies, in accordance with yet another embodiment herein.

FIGS. 24H and 12I show an angled view and a top view, respectively, of an exemplary bottom layer of the card shown in FIGS. 23 and 24A.

DETAILED DESCRIPTION OF THE PREFERRED EMBODIMENT(S)

As evident by the drawings and below description, this disclosure relates to a sample handling system (or "system" as noted throughout this disclosure) which may be used for detecting presence of an analyte (or analytes) such as metal, biomarkers, and the like, in a sample. In an embodiment, this system, depicted as system 300 in FIG. 3, may include (1) a sample handling system or "cartridge assembly" that includes sample preparation microfluidic channel(s) and at least one sensing device (or sensor) for sensing biomarkers/analytes in a test sample, and (2) a data processing and display device or "cartridge reader unit" that includes a processor or controller for processing any sensed data of the sensing device of the cartridge assembly and a display for displaying a detection event. Together these two components make up the system. In an embodiment, these components may include variable features including, without limitation, one or more reagent cartridges, a cartridge for waste, and a flow control system which may be, for example, a pneumatic flow controller.

Generally, the process for preparing a sample in the cartridge assembly, in order for detection of analytes, biomarkers, etc. to happen by the assembly and output via the cartridge reader unit, is as-follows: A raw patient sample is loaded onto a card, optionally filtered via a filter membrane, after which a negative pressure generated by off-card pneumatics filters the sample into a separated test sample (e.g., plasma). This separated test sample is quantitated on-card through channel geometry. The sample is prepared on card by interaction with mixing materials (e.g., reagent(s) (which may be dry or wet), buffer and/or wash buffer, beads and/or beads solution, etc.) from a mixing material source (e.g., blister pack, storage chamber, cartridge, well, etc.) prior to flow over the sensor/sensing device. The sample preparation channels may be designed so that any number of channels may be stacked vertically in a card, allowing multiple patient samples to be used. The same goes for sensing microfluidic devices, which may also be stacked vertically. A sample preparation card, which is part of the cartridge assembly, includes one or more structures providing functionalities selected from filtering, heating, cooling, mixing, diluting, adding reagent, chromatographic separation and combinations thereof; and a means for moving a sample throughout the sample preparation card. Further description regarding these features is provided later below.

Figure 1:
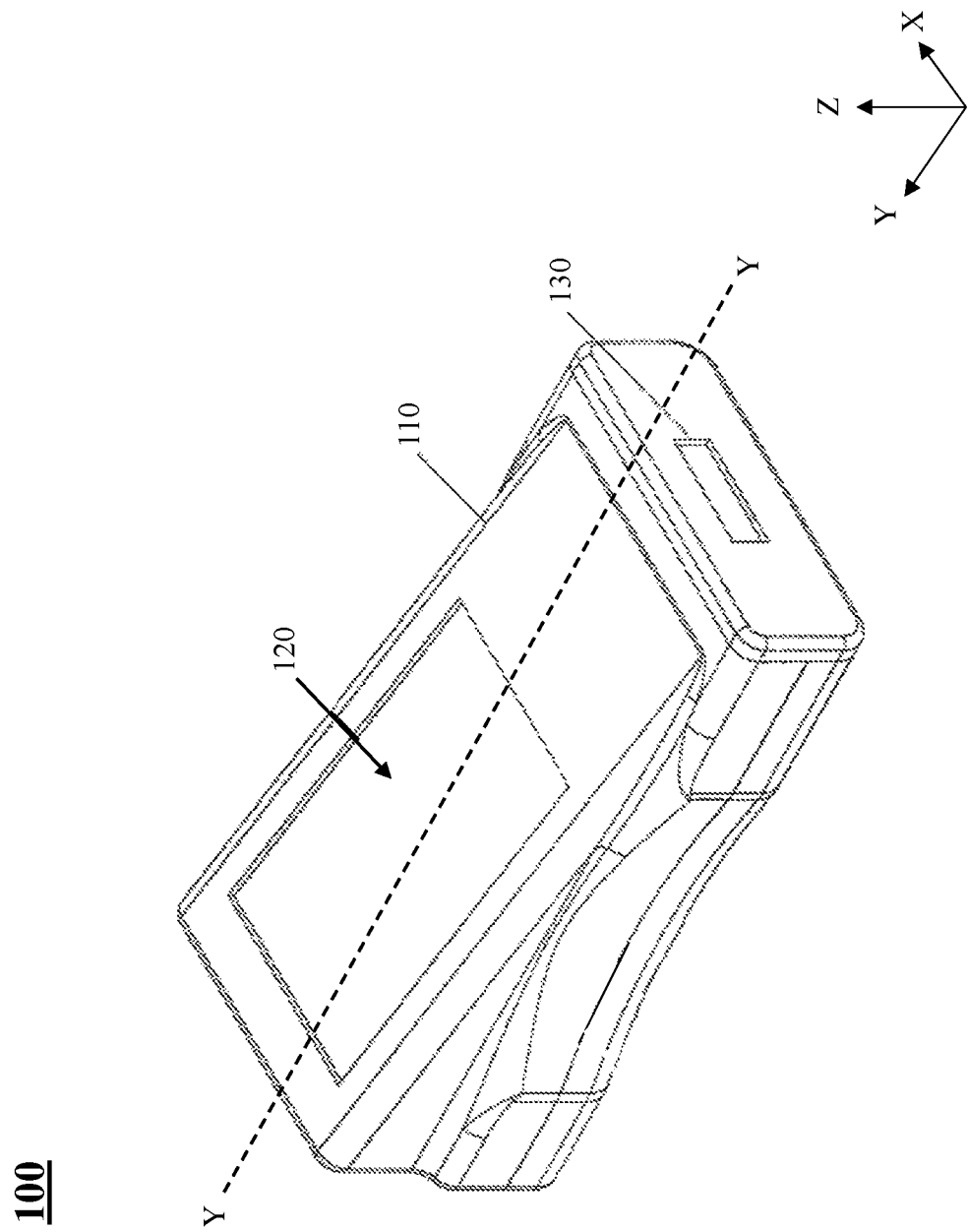
FIG. 1 is a perspective view of an exemplary cartridge reader unit used in a system in accordance with an embodiment of the present disclosure.

FIG. 1 shows an example of a cartridge reader unit 100, used in system 300 (see FIG. 3) in accordance with an embodiment. The cartridge reader unit 100 may be configured to be compact and/or small enough to be a hand-held, mobile instrument, for example. The cartridge reader unit 100 includes a body or housing 110 that has a display 120 and a cartridge receiver 130 for receiving a cartridge assembly. The housing 110 may have an ergonomic design to allow greater comfort if the reader unit 100 is held in an operator's hand. The shape and design of the housing 110 is not intended to be limited, however.

The cartridge reader unit 100 may include an interface 140 and a display 120 for prompting a user to input and/or connect the cartridge assembly 200 with the unit and/or sample, for example. In accordance with an embodiment, in combination with the disclosed cartridge assembly 200, the system 300 may process, detect, analyze, and generate a report of the results, e.g., regarding multiple detected biomarkers in a test sample, e.g., five cardiac biomarkers, using sensor (magnetoresistive) technology, and further display the biomarker results, as part of one process.

The display 120 may be configured to display information to an operator or a user, for example. The display 120 may be provided in the form of an integrated display screen or touch screen (e.g., with haptics or tactile feedback), e.g., an LCD screen or LED screen or any other flat panel display, provided on the housing 110, and (optionally) provides an input surface that may be designed for acting as end user interface (UI) 140 that an operator may use to input commands and/or settings to the unit 100, e.g., via touching a finger to the display 120 itself. The size of the display 120 may vary. More specifically, in one embodiment, the display 120 may be configured to display a control panel with keys, buttons, menus, and/or keyboard functions thereon for inputting commands and/or settings for the system 300 as part of the end user interface. In an embodiment, the control panel includes function keys, start and stop buttons, return or enter buttons, and settings buttons. Additionally and/or alternatively, although not shown in FIG. 1, the cartridge reader 100 may include, in an embodiment, any number of physical input devices, including, but not limited to, buttons and a keyboard. In another embodiment, the cartridge reader 100 may be configured to receive input via another device, e.g., via a direct or wired connection (e.g., using a plug and cord to connect to a computer (PC or CPU) or a processor) or via wireless connection. In yet another embodiment, display 120 may be to an integrated screen, or may be to an external display system, or may be to both. Via the display control unit 120, the test results (e.g., from a cartridge reader 310, described with reference to FIG. 3, for example) may be displayed on the integrated or external display. In still yet another embodiment, the user interface 140 may be provided separate from the display 120. For example, if a touch screen UI is not used for display 120, other input devices may be utilized as user interface 140 (e.g., remote, keyboard, mouse, buttons, joystick, etc.) and may be associated with the cartridge reader 100 and/or system 300. Accordingly, it should be understood that the devices and/or methods used for input into the cartridge reader 100 are not intended to be limiting. All functions of the cartridge reader 100 and/or system 300 may, in one embodiment, be managed via the display 120 and/or input device(s), including, but not limited to: starting a method of processing (e.g., via a start button), selecting and/or altering settings for an assay and/or cartridge assembly 200, selecting and/or settings related to pneumatics, confirming any prompts for input, viewing steps in a method of processing a test sample, and/or viewing (e.g., via display 120 and/or user interface 140) test results and values calculated by the GMR sensor and control unit/cartridge reader. The display 120 may visually show information related to analyte detection in a sample. The display 120 may be configured to display generated test results from the control unit/cartridge reader. In an embodiment, real-time feedback regarding test results that have been determined/processed by the cartridge reader unit/controller (by receiving measurements from the sensing device, the measurements being determined as a result of the detected analytes or biomarkers), may be displayed on the display 120.

Optionally, a speaker (not shown) may also be provided as part of the cartridge reader unit 100 for providing an audio output. Any number of sounds may be output, including, but not limited to speech and/or alarms. The cartridge reader unit 100 may also or alternatively optionally include any number of connectors, e.g., a LAN connector and USB connector, and/or other input/output devices associated therewith. The LAN connector and/or USB connector may be used to connect input devices and/or output devices to the cartridge reader unit 100, including removable storage or a drive or another system.

In accordance with an embodiment, the cartridge receiver 130 may be an opening (such as shown in FIG. 1) within the housing 110 in which a cartridge assembly (e.g., cartridge assembly 200 of FIG. 2) may be inserted. In another embodiment, the cartridge receiver 130 may include a tray that is configured to receive a cartridge assembly therein. Such a tray may move relative to the housing 110, e.g., out of and into an opening therein, and to thereby receive the cartridge assembly 200 and move the cartridge assembly into (and out of) the housing 110. In one embodiment, the tray may be a spring-loaded tray that is configured to releasably lock with respect to the housing 110. Additional details associated with the cartridge reader unit 100 are described later with respect to FIG. 3.

Figure 2A:
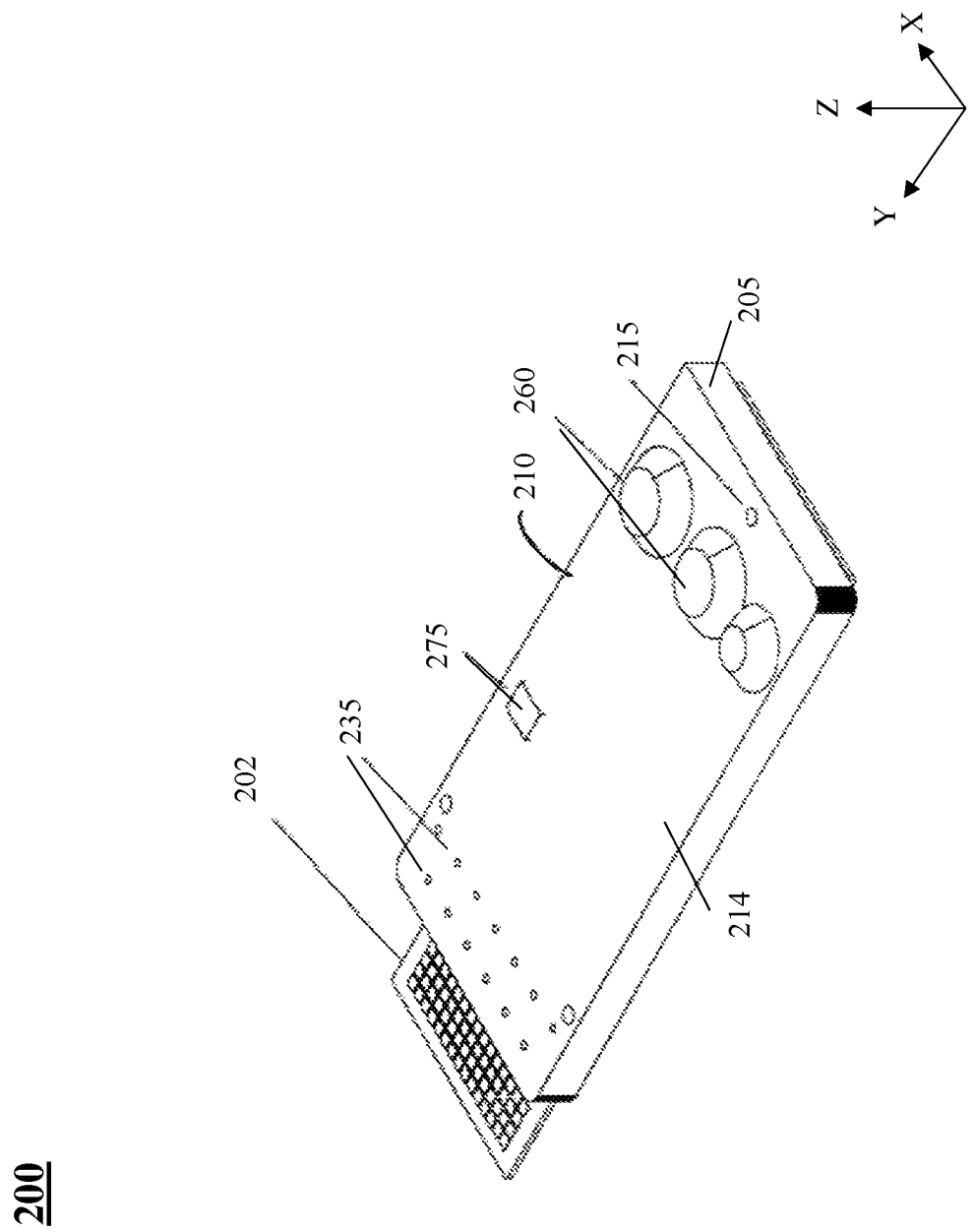
FIG. 2A is a perspective view of an exemplary cartridge assembly used in the system, in accordance with an embodiment of the present disclosure.
Figure 2B:
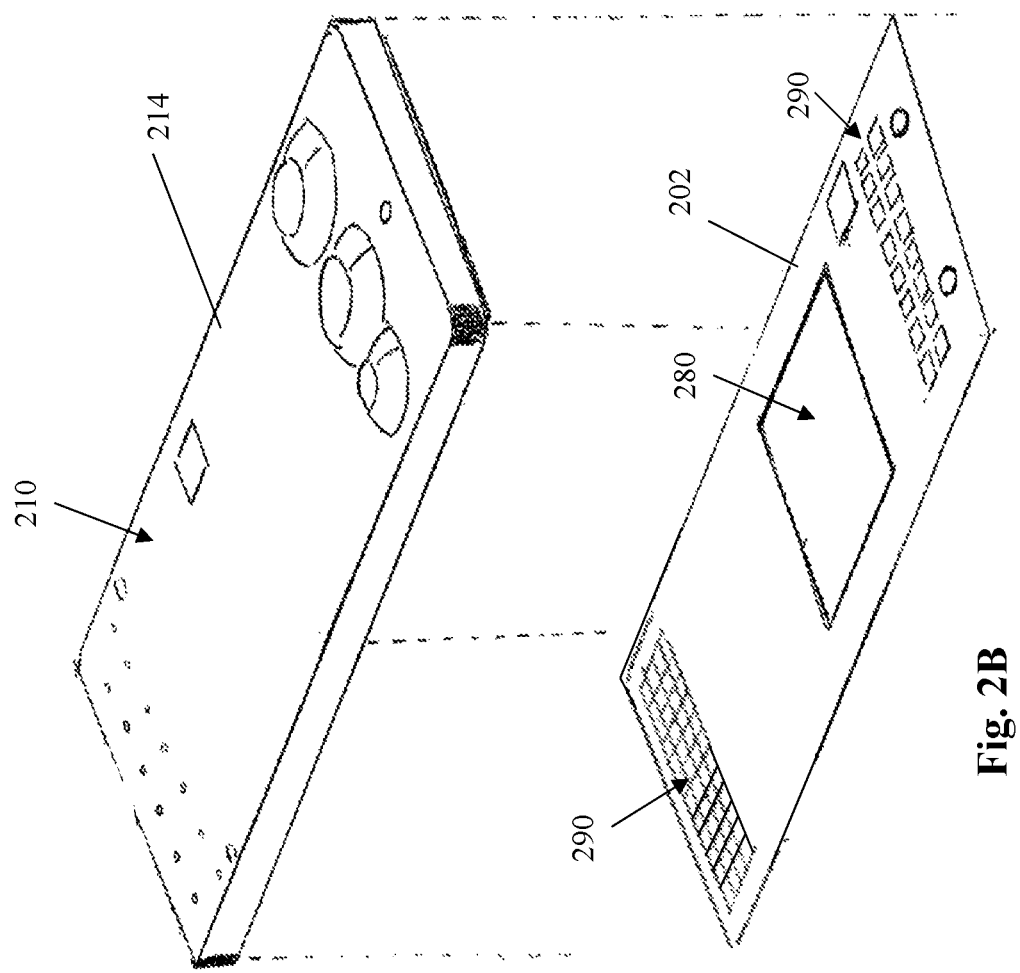
FIG. 2B is an exploded view of the cartridge assembly of FIG. 2A, in accordance with an embodiment herein.
Figure 2C:
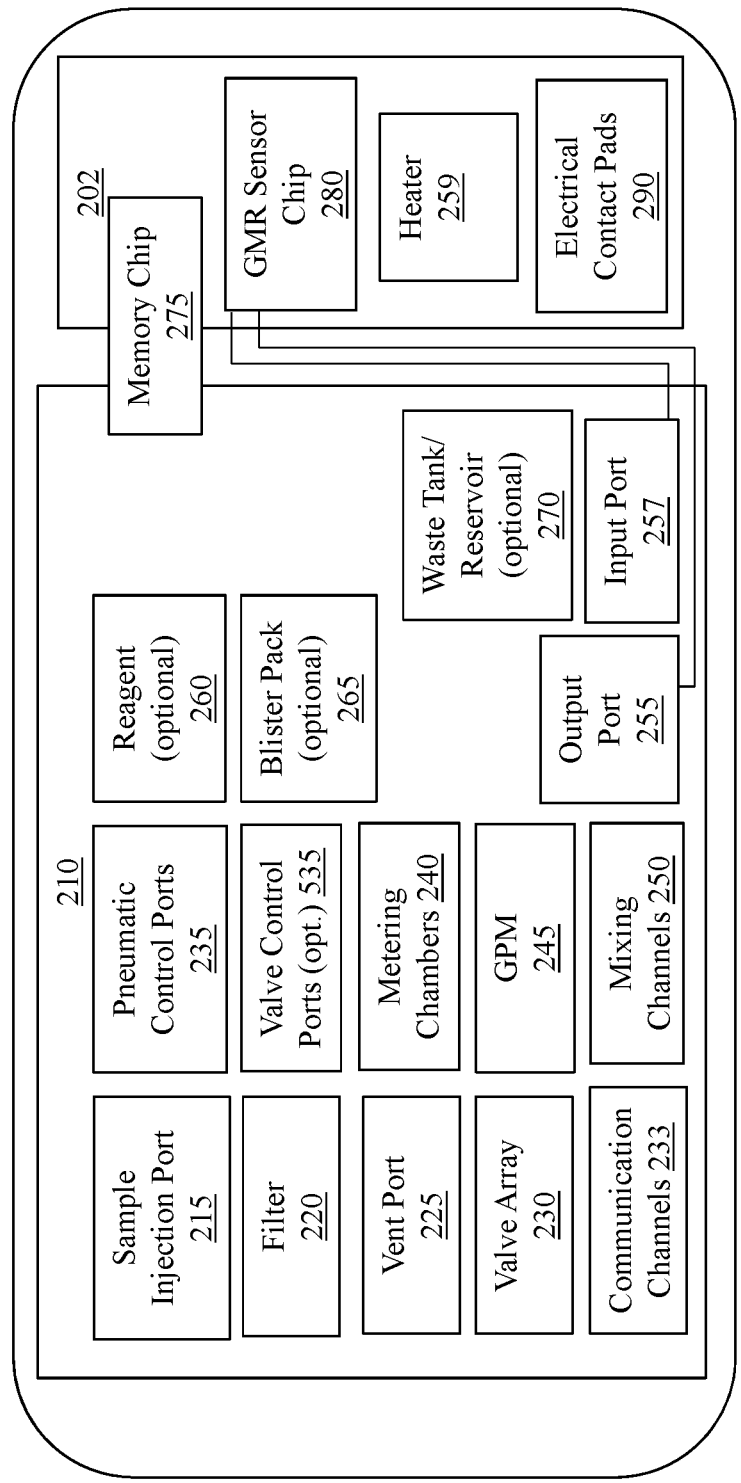
FIG. 2C is a schematic drawing of the cartridge assembly of FIG. 2A, in accordance with an embodiment herein.

As previously noted, cartridge assembly 200 may be designed for insertion into the cartridge reader unit 100, such that a sample (e.g., blood, urine) may be prepared, processed, and analyzed. FIGS. 2A-2C illustrate an exemplary embodiment of a cartridge assembly 200 in accordance with embodiments herein. Some general features associated with the disclosed cartridge assembly 200 are described with reference to these figures. However, as described in greater detail later, several different types of cartridge cards and thus cartridge assemblies may be utilized with the cartridge reader unit 100 and thus provided as part of system 300. In embodiments, the sampling handling system or cartridge assembly 200 may take the form of disposable assemblies for conducting individual tests. That is, as will be further understood by the description herein, depending on a type of sample and/or analytes being tested, a different cartridge card configuration(s) and/or cartridge assembly(ies) may be utilized. FIG. 2A shows a top, angled view of a cartridge assembly 200, in accordance with an embodiment herein. The cartridge assembly 200 includes a sample processing card 210 and a sensing and communication substrate 202 (see also FIG. 2B). Generally, the sample processing card 210 is configured to receive the sample (e.g., via a sample port such as injection port, also described below) and, once inserted into the cartridge reader unit 100, process the sample and direct flow of the sample to produce a prepared sample. Card 210 may also store waste from a sample and/or fluids used for preparing the test sample in an internal waste chamber(s) (not shown in FIG. 2A, but further described below). Memory chip 275 may be read and/or written to and is used to store information relative to the cartridge application, sensor calibration, and sample processing required, for example. In an embodiment, the memory chip 275 is configured to store a pneumatic system protocol that includes steps and settings for selectively applying pressure to the card 210 of the cartridge assembly 200, and thus implementing a method for preparation of sample for delivery to a magnetoresistive or magnetoresistance sensor (e.g., GMR sensor chip 280). The memory chip may be used to mistake-proof each cartridge assembly 200 inserted into the unit 100, as it includes the automation recipe for each assay. The memory chip 275 also contain traceability to the manufacturing of each card 210 and/or cartridge assembly 200. The sensing and communication substrate 202 may be configured to establish and maintain communication with the cartridge reader unit 100, as well as receive, process, and sense features of the prepared sample. The substrate 202 establishes communication with a controller in the cartridge reader unit 100 such that analyte(s) may be detected in a prepared sample. The sample processing card 210 and the sensing and communication substrate 202 (see, e.g., FIG. 2B) are assembled or combined together to form the cartridge assembly 200. In an embodiment, adhesive material (see, e.g., FIG. 2D) may optionally be used to adhere the card 210 and substrate 202 to one another. In an embodiment, the substrate 202 may be a laminated layer applied to the sample processing card 210. In one embodiment, the substrate 202 may be designed as a flexible circuit that is laminated to sample processing card 210. In another embodiment, the sample processing card 210 may be fabricated from a ceramic material, with the circuit, sensor (sensor chip 280) and fluid channels integrated thereon. Alternatively, the card 210 and substrate 202 may be mechanically aligned and connected together. In one embodiment, a portion of the substrate 202 may extend from an edge or an end of the card 210, such as shown in FIG. 2A. In another embodiment, such as shown in FIG. 2B, the substrate 202 may be aligned and/or sized such that it has similar or smaller edges than the card 210.

Figure 3:
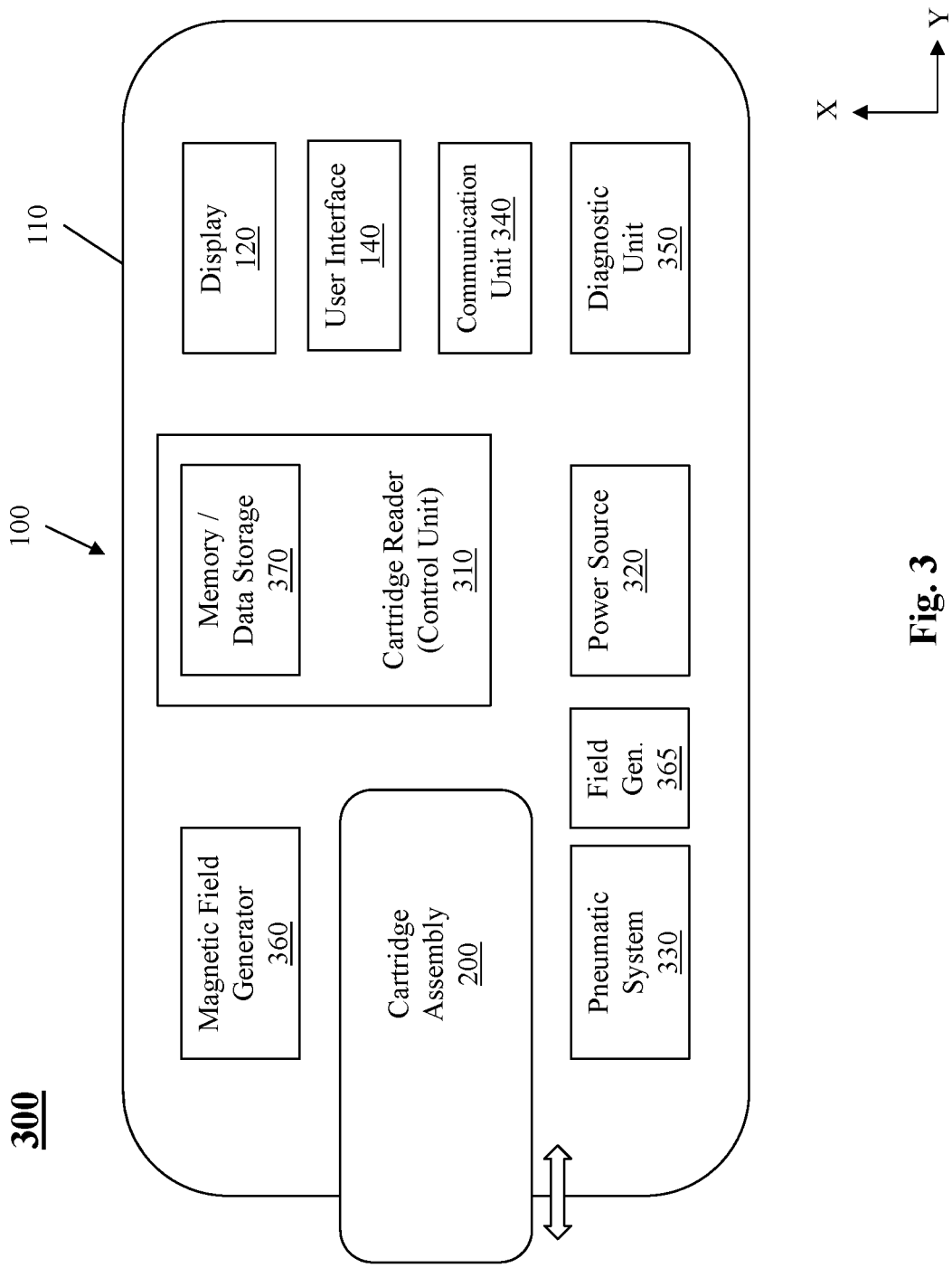
FIG. 3 is a schematic diagram of the system in accordance with an embodiment of the present disclosure.

FIG. 2C schematically illustrates features of the cartridge assembly 200, in accordance with an embodiment. As shown, some of the features may be provided on the sample processing card 210, while other may be associated with the substrate 202. Generally, to receive a test sample (e.g., blood, urine) (within a body of the card), the cartridge assembly 200 includes a sample injection port 215, which may be provided on a top of the card 210. Also optionally provided as part of the card 210 are filter 220 (also referred to herein as a filtration membrane), vent port 225, valve array 230 (or valve array zone 230), and pneumatic control ports 235. Communication channels 233 are provided within the card 210 to fluidly connect such features of the card 210. Pneumatic control ports 235 are part of a pneumatic interface on the cartridge assembly 200 for selectively applying pressurized fluid (air) to the communication channels 233 of the card, for directing flow of fluids (air, liquids, test sample, etc.) therein and/or valve array 230. Optionally, the card 210 may include distinct valve control ports 535 connected to designated communication channels 233 for controlling the valves in the valve array 230. The card 210 may also have one or more metering chambers 240, gas permeable membranes 245, and mixing channels 250 that are fluidly connected via communication channels 233. Metering chamber(s) are designed to receive at least the test sample (either directly or filtered) therein via communication channels 233. Such features are discussed in greater detail below with reference to FIGS. 14-27D, showing different exemplary embodiments of sample processing cards that may be used as part of a cartridge assembly 200. Generally, a sample may be injected into the cartridge assembly 200 through port 215 and processed by means of filtering with filter (e.g., filter 220), metering in metering chamber(s) 240, mixing in mixing channel(s) 250, heating and/or cooling (optional), and directing and changing the flow rate via communication channels 233, pneumatic control ports 235, and valve array 230. For example, flow of the fluid may be controlled using internal micro fluidic channels (also generally referred to as communication channels 233 throughout this disclosure) and valves via a connection of a pneumatic system (e.g., system 330 in the cartridge reader unit 100, as shown in FIG. 3) and a pneumatic interface e.g., on the card 210 that has pneumatic control ports 235 or a similar connection section. Optional heating of the test sample and/or mixing materials/fluids within the card 210 may be implemented, in accordance with an embodiment, via a heater 259 which may be in the form of a wire trace provided on a top side of a PCB/substrate 202 with a thermistor. Optional cooling of the test sample and/or mixing materials/fluids within the card 210 may be implemented, in accordance with an embodiment, via a TEC module integrated in the cartridge assembly 200 (e.g., on the substrate 202), or, in another embodiment, via a module integrated inside of the cartridge reader unit 100. For example, if the cooling module is provided in the unit 100, it may be pressed against the cartridge assembly 200 should cooling be required. Processing may also optionally include introduction of reagents via optional reagent sections 260 (and/or blister packs) on the card 210 and/or via reagent cartridges in the housing 110 the cartridge reader unit 100. Reagents may be released or mixed as required by the process for that sample and the cartridge assembly 200 being analyzed. Further, optional blister packs 265 may be provided on the card 210 to introduce materials such as reagents, eluants, wash buffers, magnetic nano particles, bead solution, or other buffers to the sample via communication channels 233 during processing. One or more internal waste chambers (also referred to herein as waste tanks for waste reservoirs) 270 may also be optionally provided on the card 210 to store waste from the sample and reagents. An output port 255—also referred to as a sensor delivery port, or input port to the sensor—is provided to output a prepared sample from the card 210 to a GMR sensor chip 280, as discussed below, for detecting analytes in the test sample. The output port 255 may be fluidly connected to a metering chamber for delivering the test sample and one or more mixing materials to the sensor. Accordingly, the sensor may be configured to receive the test sample and the one or more mixing materials via the at least one output port 255. In embodiments, an input port 257—also referred to as a waste delivery port, or output port from the sensor—is provided to output any fluid or sample from the GMR sensor chip 280 to a waste chamber 270. Waste chamber(s) 270 may be fluidly connected to other features of the card 210 (including, for example, metering chamber(s) 240, an input port 257, or both) via communication channels 233.

The cartridge assembly 200 has the ability to store, read, and/or write data on a memory chip 275, which may be associated with the card 210 or the substrate 202. As noted previously, the memory chip 275 may be used to store information related and/or relative to the cartridge application, sensor calibration, and required sample processing (within the sample processing card), as well as receive additional information based on a prepared and processed sample. The memory chip 275 may be positioned on the sample processing card 210 or on the substrate 200.

As previously noted, a magnetoresistive sensor may be utilized, in accordance with embodiments herein, to determine analytes (such as biomarkers) within a test sample using the herein disclosed system. While the description and Figures note use of a particular type of magnetoresistance sensor, i.e., a giant magnetoresistance (GMR) sensor, it should be understood that this disclosure is not limited to a GMR sensor platform. In accordance with some embodiments, the sensor may be an anisotropic magnetoresistive (AMR) sensor and/or magnetic tunnel junction (MTJ) sensors, for example. In embodiments, other types of magnetoresistive sensor technologies may be utilized. Nonetheless, for explanatory purposes only, the description and Figures reference use of a GMR sensor as a magnetoresistive sensor.

The substrate 202 of cartridge assembly 200 may be or include an electronic interface and/or a circuit interface such as a PCB (printed circuit board) that may have a giant magnetoresistance (GMR) sensor chip 280 and electrical contact pads 290 (or electrical contact portions) associated therewith. Other components may also be provided on the substrate 202. The GMR sensor chip 280 is attached at least to the substrate 202, in accordance with an embodiment. The GMR sensor chip 280 may be placed on and attached to the substrate 202 using adhesive, for example. In an embodiment, a liquid adhesive or a tape adhesive may be used between the GMR sensor 280 and the PCB substrate 202. Such a design may require a bond to the PCB at the bottom and a bond to the processing card at the top, for example. Alternatively, other approaches for attaching the GMR sensor chip 280 to the substrate 202 include, but are not limited to: friction fitting the GMR sensor to the PCB, and connecting a top of the GMR sensor chip 280 directly to the sample processing card 210 (e.g., in particular when the substrate 202 is provided in the form of a flexible circuit that is laminated (to the back) of sample processing card 210. The GMR sensor chip 280 may be designed to receive a prepared sample from the output port 255 of the sample processing card 210. Accordingly, placement of the GMR sensor chip 280 on the substrate may be changed or altered based on a position of the output port 255 on card 210 (thus, the illustration shown in FIG. 2B is not intended to be limiting)—or vice versa. In an embodiment, the GMR sensor chip 280 is positioned on a first side of the substrate 202 (e.g., a top side that faces an underside of the card 210, as shown in FIG. 2B), e.g., so as to receive the prepared sample from an output port that outputs on an underside of the card 210, and the contact pads 290 are positioned on an opposite, second side of the substrate (e.g., on a bottom side or underside of the substrate 202, such that the contact pads 290 are exposed on a bottom side of the cartridge assembly 200 when fully assembled for insertion into the cartridge reader unit 100). The GMR sensor chip 280 may include its own associated contact pads (e.g., metal strips or pins) that are electrically connected via electronic connections on the PCB/substrate 202 to the electrical contact pads 290 provided on the underside thereof. Accordingly, when the cartridge assembly 200 is inserted into the cartridge reader 100, the electrical contact pads 290 are configured to act as an electronic interface and establish an electrical connection and thus electrically connect with electronics (e.g., cartridge reader 310) in the cartridge reader unit 100. Thus, any sensors in the sensor chip 280 are connected to the electronics in the cartridge reader unit 100 through the electrical contact pads 290 and contact pads of the GMR sensor chip 280.

Figure 2D:
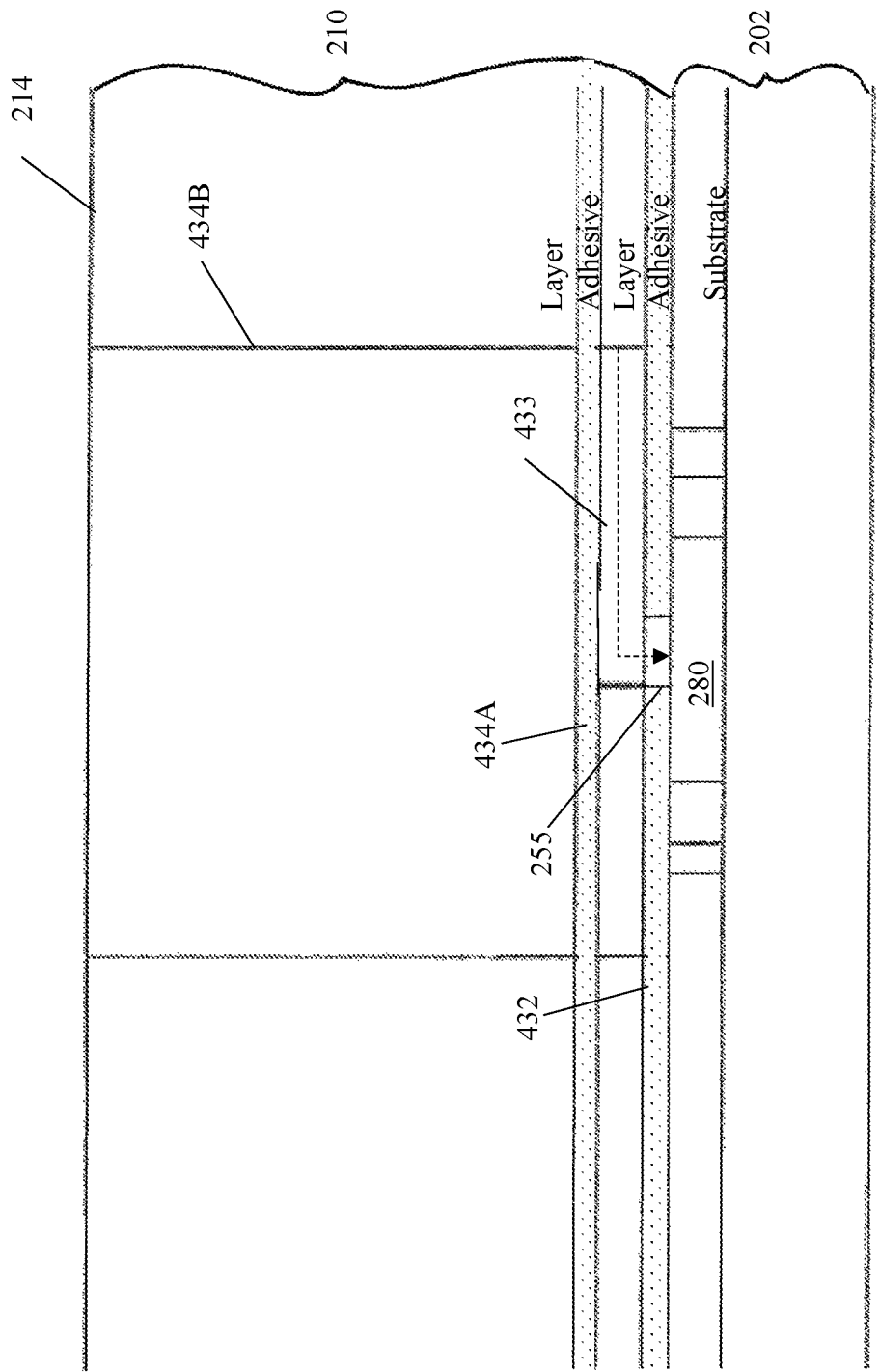
FIG. 2D shows a cross section of the cartridge assembly of FIG. 2A, illustrating a connection interface between a sample processing card and a sensing and communication substrate thereof.
Figure 2E:
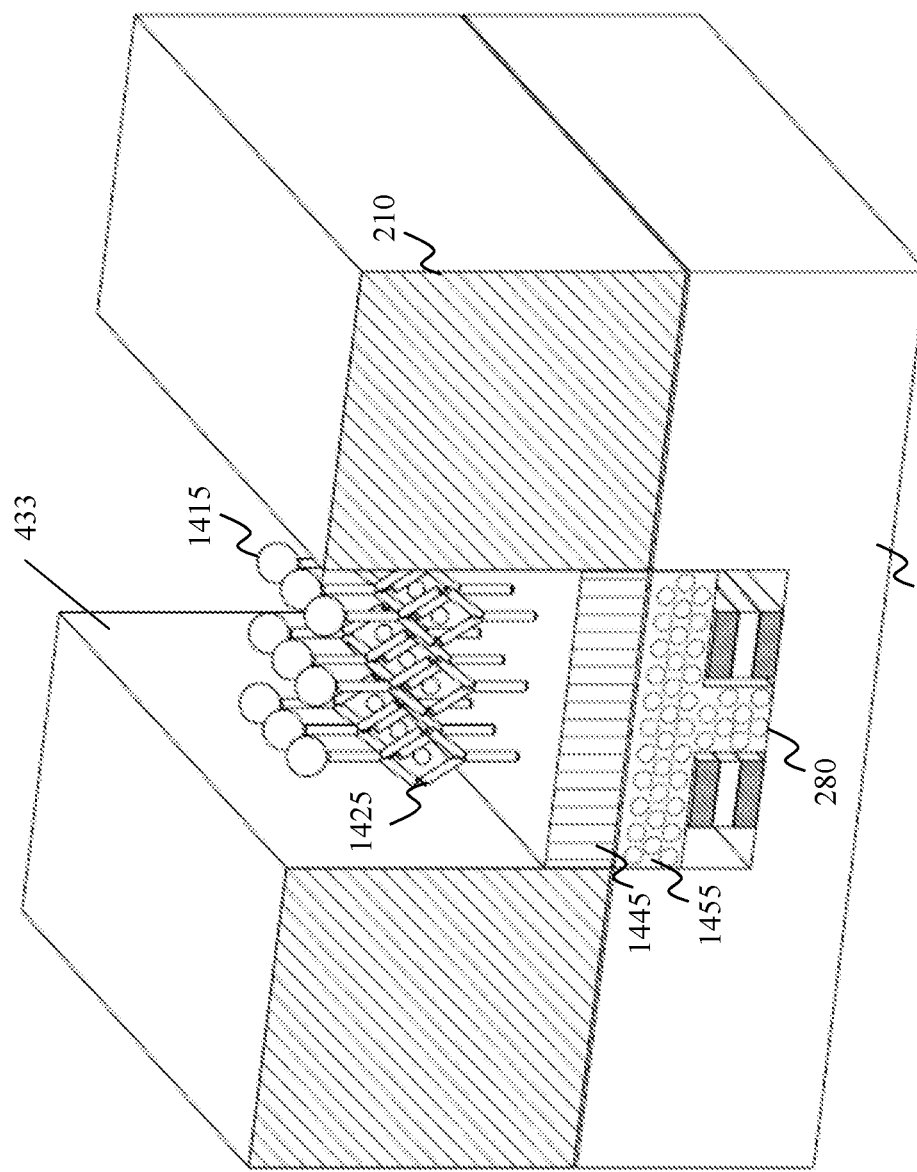
FIG. 2E shows a perspective of the cross section of FIG. 2D, showing more detail of a channel at the location of a GMR sensor, in accordance with an embodiment herein.

FIGS. 2D and 2E show views of an exemplary cross section of a mating or connection interface of card 210 and substrate 202. More specifically, FIG. 2D illustrates an interface, in accordance with one embodiment, between an output port 255 on the card 210 and GMR sensor chip 280 of the substrate 202. For example, shown is a PCB substrate 202 positioned below and adjacent to a card 210 according to any of the herein disclosed embodiments. The substrate 202 may be attached to bottom surface (222) of the card 210. The card 210 has a channel feature, labeled here as microfluidic channel 433 (which is one of many communication channels within the card 210), in at least one layer thereof, designed to direct a test sample that is processed within the card 210 to an output port 255 directed to GMR sensor 280. Optionally, adhesive material may be provided between layers of the card 210, e.g., adhesive 434A may be provided between a layer in the card that has reagent ports 434B and a layer with the channel 433. The substrate 202 includes a GMR sensor chip 280 that is positioned adjacent to the channel 433 and output port 255 of the card 210. FIG. 2E shows a schematic drawing related to analyte detection using a card 210 with said one or more microfluidic channels 433 and GMR sensor chip 280 associated with a silicon wafer of a PCB substrate 202. The analyte detection is made possible through micro fluidics, surface chemistry, sample targets, nano magnetic beads, magnetic field and giant magneto resistance (GMR) sensor chip 280. Micro fluidic channel(s) 433 (i.e., communication channels) in the card 210 may assist in directing flow of a separated test sample and nano magnetic beads from a magnetic bead-bound entity 1415 for processing, for example. Magnetic bead-bound entity 1415 may be configured to interact with biomolecule 1425 (also referred to as a target) or an analyte of interest, such as in a sandwich complex of antibody-analyte-magnetic bead-bound antibody. Sample targets are the items to be detected and measured. Nano magnetic beads 1415 bond to sample targets 1425. Optionally, an insulating material 1445, 1455 may be provided between over the sensor(s) 280. For example, in the embodiment shown in FIG. 2E, below biosurface 1445 is a further insulating layer 1455. Insulating layer 1455 may be in direct contact with GMR sensor(s) 280 and may comprise, for example, a metal oxide layer. Biosurface layer 1445 may be in direct contact with insulating layer 1455, in accordance with one embodiment. Substrate 202 may serve as a scaffold for each component above it, e.g., the GMR sensors 280, insulating layer 1455, and/or biosurface layer 1445. In some embodiments, substrate 202 may be made from a silicon wafer or a laminated flex layer.

Magnetic field (from a magnetic field generator 365 that is different than magnetic field generator 360, described below with reference to FIG. 3) may be used to excite the nano magnetic particles located near sensors. FIG. 2F shows a schematic example of antiparallel and parallel magnetization, for example. Similar principles may be applied here at the GMR sensor chip 280. Specifically, as shown in FIG. 2F, the GMR sensor may be designed to include of a metallic multi-layered structure with a non-magnetic conductive interlayer 890 sandwiched between two magnetic layers 880A and 880B. In an embodiment, the non-magnetic conductive interlayer 890 may be a thin copper film. In an embodiment, GMR sensor chip 280 is constructed using a metallic structure with several nanometers non-magnetic conducting thin film (e.g., copper) sandwiched between two ferromagnetic layers (880A and 880B in FIG. 2F) changes depending on the relative magnetization direction of the ferromagnetic layers. The electrical resistance of the metallic multi-layered structure changes depending on the relative magnetization direction of the magnetic layers 880A and 880B. Parallel magnetization (as shown in the right half of FIG. 2F) results in lower resistance, while anti-parallel magnetization (as shown in the left half of FIG. 2F) results in higher resistance. This phenomenon facilitates detection of stray fields from magnetic materials at nanometer scales. The magnetization direction may be controlled by a magnetic field applied externally. As a result, the metallic multi-layered structure displays a change in its electrical resistance as a function of the external magnetic field.

GMR sensors have sensitivities that exceed those of anisotropic magnetoresistance (AMR) or Hall sensors. This characteristic enables detection of stray fields from magnetic materials at nanometer scales. For example, stray fields from magnetic nanoparticles that bound on sensor surface will alter the magnetization in the magnetic layers, and thus change the resistance of the GMR sensor. Accordingly, changes in the number of magnetic nanoparticles bound to the GMR sensor per unit area can be reflected in changes of the resistance value of the GMR sensor.

For such reasons, the sensor utilized in cartridge assembly 200, in accordance with the embodiments described herein, is a GMR sensor chip 280.

Referring now to FIG. 3, additional features of the cartridge reader unit 100 are schematically shown to further describe how the cartridge reader unit 100 and cartridge assembly 200 are configured to work together to provide the system 300 for detecting analyte(s) in a sample. As depicted, the cartridge assembly 200 may be inserted into the housing 110 of the cartridge reader unit 100. Generally, the housing 110 of the cartridge reader unit 100 may further include or contain a processor or control unit 310, also called a "controller" and/or a "cartridge reader" 310 herethroughout, a power source 320, a pneumatic system 330, a communications unit 340, a (optional) diagnostic unit 350, a magnetic field generator 360, and a memory 370 (or data storage), along with its user interface 140 and/or display 120. Optionally, a reagent opener (not shown in FIG. 3), e.g., for opening a reagent source on an inserted cartridge assembly or for introducing reagent into the cartridge assembly (e.g., if the reagent is not contained in the assembly in a particular reagent section), may also be provided as part of the cartridge reader unit 100. Once a cartridge assembly 200 is inserted into the housing 110 of the cartridge reader unit 100, and the electrical and pneumatics system(s) are connected, and the cartridge memory chip 275 may be read from the cartridge assembly 200 (e.g., read by cartridge reader 310/ control unit, or PCB assembly, in the unit 100) to determine the pneumatic system protocol that includes steps and settings for selectively applying pressure to the card 210 of the cartridge assembly 200, and thus implementing a method for preparation of sample for delivery to a sensor (e.g., GMR sensor chip 280), and thus the sample placed in the assembly 200 may be prepped, processed, and analyzed. The control unit or cartridge reader 310 may control inputs and outputs required for automation of the process for detecting the analyte(s) in a sample. The cartridge reader 310 may be a real-time controller that is configured to control, among other things, the giant magnetic resistance (GMR) sensor chip 280 and/or memory chip 275 associated with the cartridge assembly 200 and the pneumatic system 330 within the housing 110, as well as the controls from user interface, driving the magnetic field generator 360, and receiving and/or sending signals from/to sensor chip and/or memory associated with the cartridge assembly 200, for example. In an embodiment, the cartridge reader 310 is provided in the form of a PCB (printed circuit board) which may include additional chips, memory, devices, therein. The cartridge reader 310 may be configured to communicate with and/or control an internal memory unit, a system operation initializer, a signal preparing unit, a signal preparing unit, a signal processing unit, and/or data storage (none of which are shown in the Figures), for example. The cartridge reader 310 may also be configured to send and receive signals with respect to the communications unit 340 such that network connectivity and telemetry (e.g., with a cloud server) may be established, and non-volatile recipes may be implemented, for example. Generally, the communications unit 340 allows the cartridge reader unit 100 to transmit and receive data using wireless or wired technology. Power can be supplied to the cartridge reader unit 100 via power source 320 in the form of an internal battery or in the form of a connector that receives power via an external source that is connected thereto (e.g., via a cord and a plug). Power source 320 is configured to supply power to parts of the cartridge reader unit 100, when activated and/or when a cartridge assembly 200 is mated with the unit 100. For example, power source 320 may supply power to the control unit and PCB assembly 560 of cartridge reader 310, magnetic field generator 360, display 120 and/or user interface 140, and pneumatic system 330 (including, for example, any motors, valves, and/or pumps associated therewith). Power source 320 may be at least one internally mounted battery pack 320, in accordance with an embodiment herein. The pneumatic system 330 is used to process and prepare a sample (e.g., blood, urine) placed into the cartridge assembly 200 by means of moving and directing fluids inside and along the sample processing card 210 (e.g., via pneumatic connection 235, through its channels and connecting to direct elastomeric valves). The pneumatic system 330 may be a system and/or device for moving fluid, which could use, for example, plungers and/or pistons in contact with fluids. The magnetic field generator 360 may be an external magnetic coil or other field generating device that is mounted in the unit 100 or integrated in some fashion with one or more of the chips (e.g., sensor chip 280) provided on the cartridge assembly 200 or provided on the circuit board of the cartridge reader unit 100. The magnetic field generator 360 is used to stimulate magnetic nanoparticles near the GMR sensor chip 280 while reading the signal. In accordance with embodiments, a second magnetic field generator 365, which may be a coil or other field generating device, may be provided as part of the cartridge reader unit 100 and in the housing 110. For example, in accordance with an embodiment, the second magnetic field generator 365 may be separate and distinct from magnetic field generator 360. This second magnetic field generator 365 may be configured to generate a non uniform magnetic field such that it may apply such a magnetic field to a part (e.g., top, bottom, sides) of the sample processing card 210 of an assembly 200 during preparation and processing of a sample, e.g., when moving mixing material(s), such as a buffer and/or magnetic beads from a mixing material source, and test sample within the card. In an embodiment, the second magnetic field generator 365 is provided on an opposite end or side of the cartridge reader unit (e.g., located in a top of the housing 110 of unit 100), i.e. away from the magnetic field generator 360, which is used for GMR sensing. In one embodiment, the second magnetic field generator 365 is provided on an opposite end of the cartridge reader unit as compared to the magnetic field generator 360 (e.g., second magnetic field generator is located in a top of the housing 110 of unit 100 and magnetic field generator 360 is provided at a bottom end of the unit 100 (e.g., near cartridge receiver 130)). In an embodiment, the total magnetic field for sensing biomarkers/analytes includes an applied field from magnetic field generator 360 (either external or integrated with the sensor chip) along with any disturbance from magnetic nanoparticles near the GMR sensor chip 280. The reagent opener is optionally used to introduce reagents during the sample processing and reading of the GMR sensor chip 280 (e.g., if the reagent is not contained in the card in a particular reagent section). As described previously, the user interface/display 120 allows an operator to input information, control the process, provide system feedback, and display (via an output display screen, which may be a touch screen) the test results.

Figure 4:
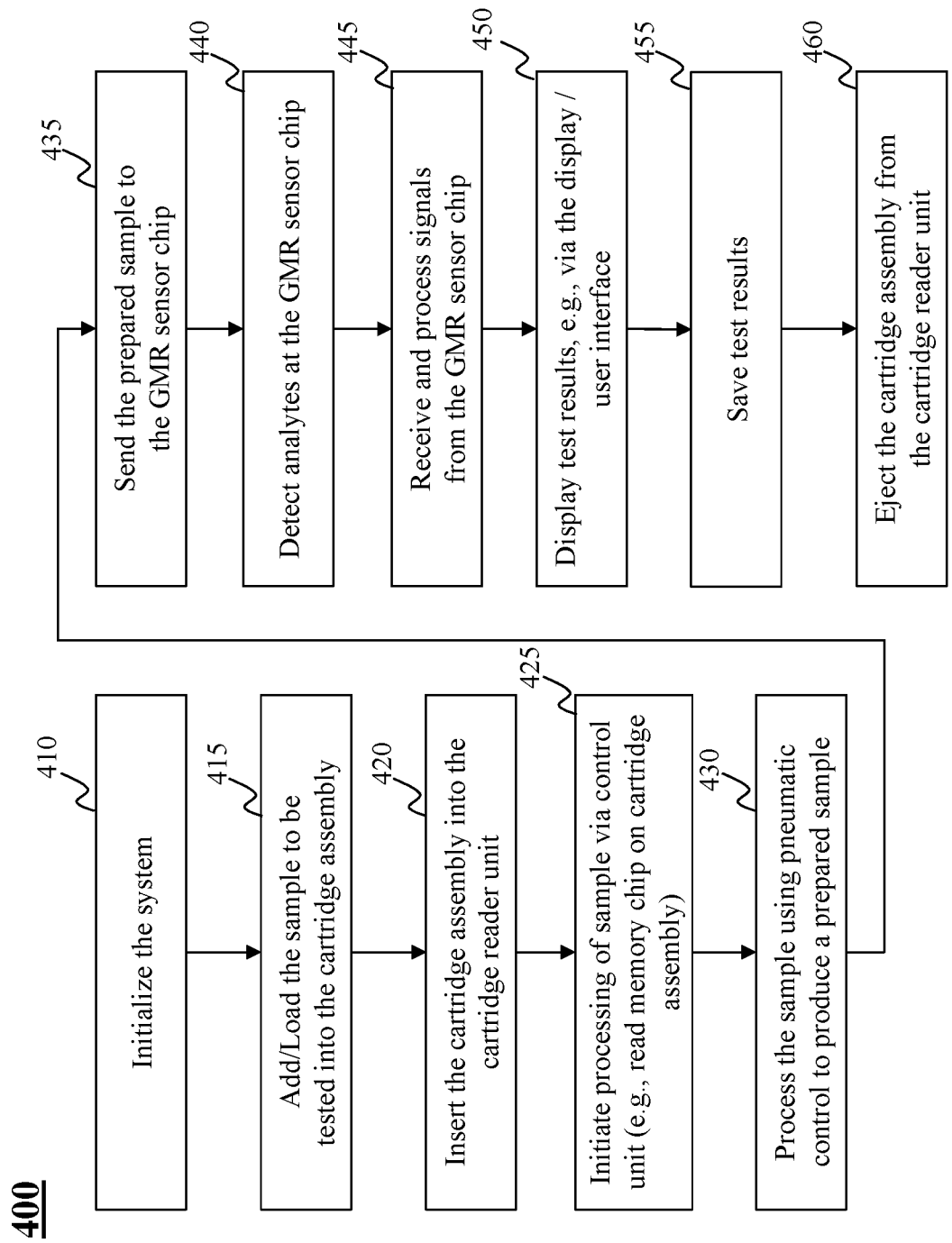
FIG. 4 shows steps of a method for performing analyte detection in a sample when using features of the herein disclosed system of FIG. 3, in accordance with an embodiment.

FIG. 4 shows general steps of a method 400 for performing analyte detection in a sample using the herein disclosed system 300. At step 410, the system is initialized. For example, initialization of the system may include: applying power to the system 300 (including cartridge reader unit 100), determining configuration information for the system, reading computations, determining that features (e.g., magnetic field generator and carrier signals) are online and ready, etc. At step 415, a whole test sample is added or loaded into the cartridge assembly 200 (e.g., sample is injected into the injection port 215, as shown in FIG. 2C). The order of steps 410 and 415 may be changed; i.e., the addition of the whole test sample to the assembly 200 may be before or after the system is initialized. At step 420, the cartridge assembly 200 is inserted into the cartridge reader unit 100. Optionally, as part of method 400, user instruction may be input to the cartridge reader unit 100 and/or system 300 via the user interface/display 120. Then, at step 425, the processing of sample is initiated via the control unit 310. This initiation may include, for example, receiving input via an operator or user through the user interface/display 120 and/or a system that is connected to the reader unit 100. In another embodiment, processing may be initiated automatically via insertion of the cartridge assembly 200 into the cartridge reader unit 100 and detecting presence of the cartridge assembly 200 therein (e.g., via electrical connection between electrical contact pads 290 on the assembly 200 with the control unit 310, and automatically reading instructions from memory chip 275). The sample is processed at step 425 using pneumatic control instructions (e.g., obtained from memory chip 275) in order to produce a prepared sample. As generally described above (and further later below), the processing of the sample may be dependent upon the type of sample and/or the type of cartridge assembly 200 inserted into the reader unit 100. In some cases, the processing may include a number of steps, including mixing, introduction of buffers or reagents, etc., before the sample is prepared. Once the sample is prepared, the prepared sample is sent (e.g., through channels in the card 210 and to output port 255, via pneumatic control through pneumatic system 330 and control unit 310) to the GMR sensor chip 280. At step 440, analytes in the prepared sample are detected at the GMR sensor chip 280. Then, at step 445, signals from the GMR sensor chip 280 are received and processed, e.g., via cartridge reader 310 (control unit; which may include one or more processors, for example). Once the signals are processed, test results may be displayed at 450, e.g., via the display 120/user interface. At 455, test results are saved. For example, test results may be saved in a cloud server and/or memory chip 275 on board the cartridge assembly 200. In embodiments, any fluids or sample may be directed from the GMR sensor chip 280 through an input port 257 to waste chamber 270. Thereafter, once all tests are preformed and read by the sensing device/GMR sensor chip 280, the cartridge assembly 200 may be ejected from the cartridge reader unit 100. In accordance with an embodiment, this may be automatically performed, e.g., mechanics within the housing 110 of the cartridge reader unit 100 may push the assembly 200 out of the housing 110, or performed manually (by way of a button or force) by the operator, for example.

In an embodiment, the system 300 described herein may utilize a pneumatic control system as disclosed in International Patent App. No. PCT/US2019/043720, entitled "SYSTEM AND METHOD FOR GMR-BASED DETECTION OF BIOMARKERS" and filed on the same day, which is hereby incorporated by reference herein in its entirety.

In an embodiment, the system 300 described herein may sense analytes as disclosed in International Patent App. No. PCT/US2019/043766, entitled "SYSTEM AND METHOD FOR SENSING ANALYTES IN GMR-BASED DETECTION OF BIOMARKERS" and filed on the same day, which is hereby incorporated by reference herein in its entirety. For example, in an embodiment, the sensing device, or GMR sensor chip 280, may include one or more microfluidic channels and a plurality of sensor pads disposed within the one or more microfluidic channels as disclosed in the PCT/US2019/043766 application. In an embodiment, such a channel may optionally include a plurality of GMR sensors disposed within a channel. GMR sensors may be all identically configured to detect a single analyte, the redundancy allowing for enhanced detection. GMR sensors may also be all configured differently to detect a myriad of analytes or a combination of differently configured sensors with some redundancies. The configuration of the channel is not limiting. Collectively, the GMR sensors in the channel may be designed to provide the output (test results) from the GMR sensor chip 280.

FIGS. 28-31 generally illustrate functional blocks of the cartridge reader 310 (control unit) and a signal processor within the cartridge reader unit 100, and processes associated therewith, that may be utilized and implemented by the cartridge reader unit 100 with regards to an inserted cartridge assembly 200. In an embodiment, the system 300 described herein may process signals at the GMR sensor as disclosed in International Patent App. No. PCT/US2019/043791, entitled "SYSTEM AND METHOD FOR PROCESSING ANALYTE SIGNALS IN GMR-BASED DETECTION OF BIOMARKERS and filed on the same day, which is hereby incorporated by reference herein in its entirety. For example, as noted above, at step 445, signals from the GMR sensor chip 280 are received and processed, e.g., via cartridge reader 310. In an embodiment, cartridge reader 310 is configured to perform the function of processing results from the GMR sensor chip 280 using a sample preparation control part having a memory reader unit and a sample preparation control unit (e.g., used to receive signals indicating that a cartridge assembly 200 has been inserted into the cartridge reader unit 100, read information stored in the memory chip 275, and generate pneumatic control signals and send them to the pneumatic system 330) and a signal processing part adapted to control electrical elements, prepare and collect signals, and process, display, store, and/or relay detection results to external systems, including processing measurements signals to obtain test results of the analyte detection, as described in detail in the PCT/US2019/043791 application. Additional features relating to the cartridge reader 310 and signal processor of the unit 100 are provided in greater detail later in this disclosure.

It should be understood that, with regards to FIGS. 1 and 2A-2F, the features shown are representative schematics of a cartridge reader unit 100 and cartridge assembly 200 that are part of the herein disclosed system 300 for detecting the analyte(s) in a sample. Accordingly, the illustrations are explanatory only and not intended to be limiting.

Turning back to the features of the sample processing card 210 and cartridge assembly 200 as previously discussed with reference to FIG. 2C, the arrangement, placement, inclusion, and number of features provided on a sample processing card 210 in the cartridge assembly 200 may be based on the test sample being analyzed and/or the test being performed (e.g., detection of biomarkers, detection of metal, etc.), for example. Further, the card 210 may be arranged, in some embodiments, such that there are zones on the card, and/or such that features are provided in different layers (however, such layers do not need to be distinct layers with a body thereof; rather, layered relative to one another at a depth or height (in the Z-direction)). In accordance with embodiments herein, the sample processing card 210 may be formed using parts that are laser cut to form inlets, channels, valve areas, etc. and sandwiched and connected/sealed together. In other embodiments, one or more layers of the sample processing card may be laser cut, laminated, molded, etc. or formed from a combination of processes. The method of forming the sample processing card 210 is not intended to be limiting. For illustrative purposes herein, some of the Figures include a depiction of layers to show positioning of parts of the sample processing card 210 relative to one another (e.g., positioning within the card relative to other features that are placed above and/or below). Such illustrations are provided to show exemplary depths or placement of the features (channels, valves, etc.) within a body of the sample processing card 210, without being limiting.

Generally, each card 210 has body 214 extending in a longitudinal direction along a longitudinal centerline A-A (provided in the Y-direction) when viewed overhead or from the top. In an embodiment, each card 210 may have dimensions defined by a length extending in the longitudinal direction (i.e., along or relative to centerline A-A), a width extend laterally to the length (e.g., in the X-direction), and a height (or depth or thickness) in the Z-direction, or vertical direction. In a non-limiting embodiment, the body 214 of the card 210 may be of a substantially rectangular configuration. In one embodiment, the cartridge receiver 130 (and/or any related tray) in the cartridge reader unit 100 is sized to accommodate the dimensions of the sample processing card 210, such that the card 210 may be inserted into the housing of the unit 100. The features noted with respect to FIG. 2C are now further described herein.

Figure 5:
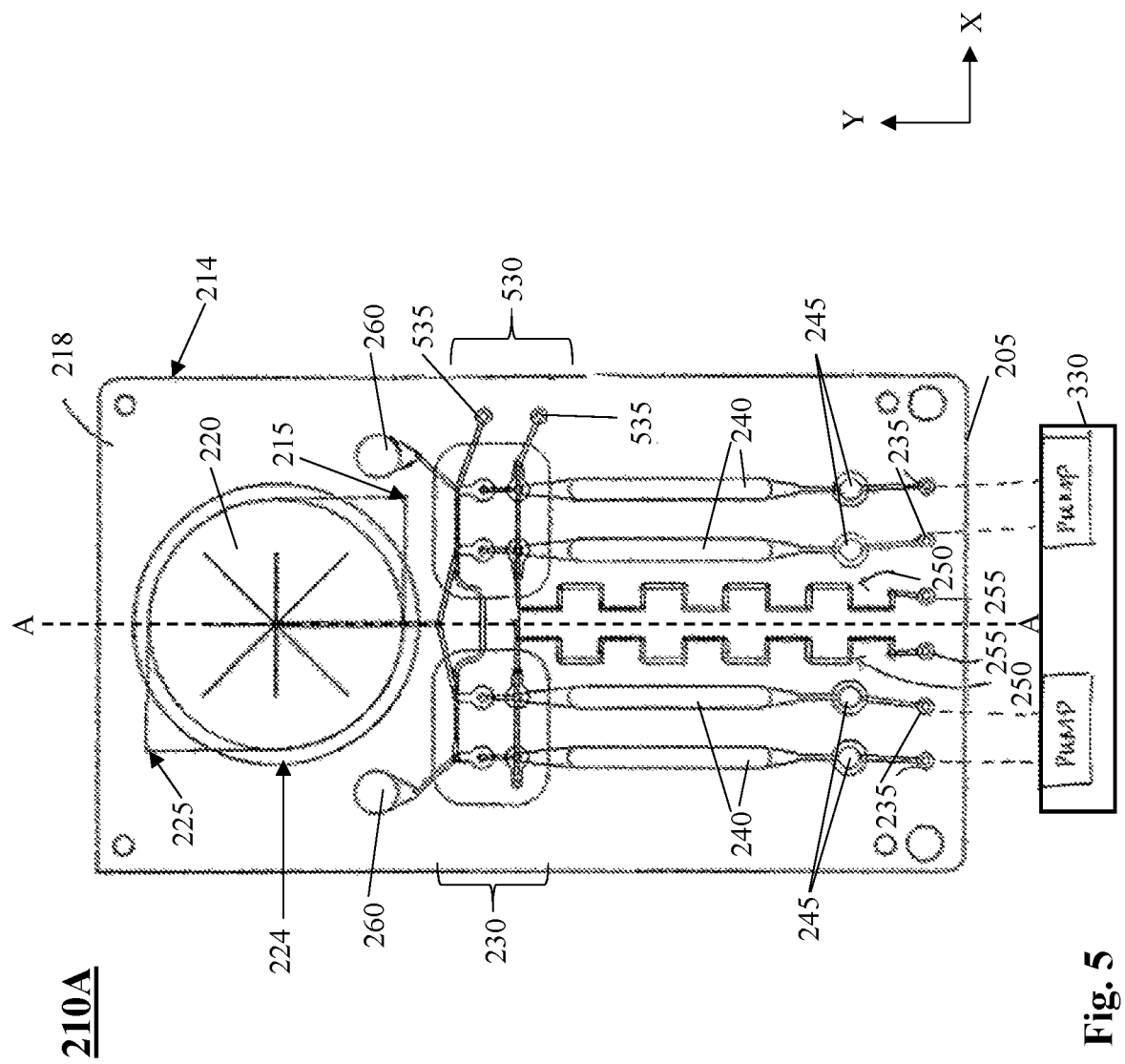
FIG. 5 is a top or overhead view of a sample processing card, configured for use as part of a cartridge assembly, in accordance with an embodiment therein.

In the description below, FIGS. 5-13 may be referenced to help illustrate features of an exemplary sample processing card 210. However, it should be understood that FIG. 5 is an example of a sample processing card 210A configured for use as a sample processing card in the cartridge assembly 200, in accordance with an embodiment therein, and that FIGS. 6-13 are illustrative only, and none of these embodiments are intended to be limiting.

Generally, a sample processing card 210 may include a sample injection area, a valve array zone 230, a mixing zone, a pneumatic control interface (also referred to herein as a pump interface or pneumatic interface) and a control and delivery zone (to sensor chip 280). Any of these areas and/or zones may be positioned relative to one another and/or overlap one another (e.g., in different layers of the card). The sample injection area is an area on the card for injecting the whole test sample. Valve array zone 230 includes a number and/or a series of valves therein that are controlled by the pneumatic system 330 in the cartridge reader unit 100 for directing and/or mixing fluids within the card 210. The valves in this zone 230 may be connected to communication channels within the sample processing card 210. Mixing zone refers to areas used to mix the separated test sample with and/or move other fluids (e.g., reagents, wash buffers, magnetic beads). The valves (e.g., with elastomeric deflection portions) in the valve array zone 230 may be selectively controlled between open and closed positions to allow for selective delivery through communication channels, e.g., delivery of the test sample to fluid metering chamber(s) 240 that may be provided in the mixing zone, for mixing with reagents, buffers, etc., for example. Control and delivery zone may be an area on the card 210 that communicates with the cartridge reader 310 of the unit 100 as well as the pneumatic system 330 thereof. In an embodiment, a number of ports 235 (at least one pneumatic control port 235) for controlling movement of the fluids within channels of the card 210 are provided in the pneumatic control interface. In some embodiments, the control and delivery zone may also optionally include ports for controlling the positions of the valves in the valve array zone 230. Each pneumatic control port 235 has a corresponding communication channel fluidly connected thereto for connection with other features (e.g., metering chamber) within the card 210. These zones and the description thereof are exemplary only and not intended to be limiting.

As previously noted, in accordance with an embodiment, a sample processing card 210 may include a sample injection port 215, which may be provided on the card 210, for receiving the test sample within a body of the card. The injection port 215 is configured to receive a whole test sample, e.g., whole blood, urine, etc., in accordance with some embodiments herein. In other embodiments, the test sample may be pre-separated (e.g., serum from blood) before injecting into the injection port 215. The injection port 215 may include a small opening with a receiving hole provided in the top surface 218 of the card 210 that extends vertically (downwardly, in the Z-direction) at a depth into the card 210 and optionally through to the filtration membrane, e.g., filter 220.

The filtration membrane 220 may be provided between or sandwiched at a depth between the top surface 218 and bottom surface 222 of the sample processing card 210, in accordance with embodiments. In the illustrated embodiment of FIG. 5, for example (as well as other Figures), the filtration membrane 220 of sample processing card 210A is depicted as being generally circular; however, the area or shape of the membrane 220 is not intended to be limited. As generally understood by one of skill in the art, the filtration membrane 220 is formed from a material configured to receive an injected whole test sample and separate a test sample (for further preparation, e.g., with reagents, buffers, magnetic beads) from that sample. In embodiments, the filter membrane 220 may be a blood filtration membrane, e.g., to separate a plasma sample from whole blood. The filtration membrane 220 may be formed from an asymmetric filter material, for example. Such a material may have an increasing smaller pore size on its underside. In the case of a whole blood test sample, for example, the membrane 220 may be used to remove red blood cells and other large biological materials from the patient test sample injected into the injection port 215, and provide plasma for further processing in the sample processing card 210. In other embodiments, the filter may be provided in the form of a glass fiber membrane 220A. For example, glass fiber membrane 220A may be used for nucleic acid extraction (whereas filter membrane 220 is used to filter plasma from whole blood), in accordance with an embodiment. While generally filter 220 may be used throughout the description, it should be understood that reference to filter or filter membrane 220 and its features may also refer and apply to glass fiber membrane 220A, in this disclosure.

As previously noted, filter 220 (or 220A) may be optional within the card 210 and cartridge assembly 200. In an embodiment, for example, the test sample may be separated by a user or operator outside of the cartridge assembly 200. As an example, in the instance of utilizing whole blood as a test sample, a user may first separate serum or plasma therefrom, i.e., outside of the assembly 200. Accordingly, use of a filter in the assembly 200 may not be required.

In use, the test sample (e.g., whole blood) may be loaded, introduced, or injected (e.g., using a pipette or needle) into the small opening of injection port 215. The sample may then be configured to spread laterally through and across the filtration membrane 220 to purify and/or separate components of the sample (e.g., in the case of an injected whole blood sample, the filter 220 will filter the blood to yield plasma). The separated test sample (e.g., plasma) may settle into a bottom portion or receiving area 224, also referred to herein as a sample chamber 224, in the sample processing card 210. This receiving area 224 may be provided adjacent to or below (in the vertical direction, i.e., direction of depth or height; in the Z-direction) the filtration membrane 220, for example. In an embodiment, the loaded or injected sample will wick across the filtration membrane 220—as represented in some Figures by the lines therein—e.g., up and/or diagonally to a side opposite the injection port 215, where the vent port 225 may be positioned or provided.

Vent port 225 is an opening in the sample processing card 210 that extends vertically at a depth between the area of the filtration membrane 220 and the top surface 218 of the sample processing card 210. In an embodiment, the depth of the vent port 225 extends from the receiving area 224 (e.g., top or bottom of the area 224, or sample chamber) to the top surface 218. Vent port 225 is open to the atmosphere and configured to vent air from the card. Vent port 225 may be similar in size to the opening of injection port 215, in accordance with an embodiment. The vent port 225 extends down into same plane as the membrane 220, in one embodiment. This vent port 225 allows pressure to be vented or released from inside the sample processing card (e.g., from the membrane 220 and/or receiving area 224, or other connected channels therein) and out to the atmosphere; e.g., as a blood test sample is injected and wicked in the membrane 220, it separates the plasma and any air in this area is pushed out through vent port 225. In accordance with an embodiment, vent port 225 may be positioned relatively opposite (i.e., 180 degrees) to the injection port 215. In the exemplary illustrated embodiment of FIG. 5, for example, the vent port 26 is shown on an upper, left side near the membrane 220. In another embodiment, the vent port 225 and injection port 215 may be positioned closer together, or on a same side of the sample processing card. In an embodiment, a channel, guide, or other portion may be provided in a layer of the sample processing card that routes the channels around the membrane 220, for example. In one embodiment, the location of the injection port 215 and vent port 225 may be switched or rotated to another location around or relative to the filtration membrane 220. For example, referring to the embodiment of FIG. 5, the injection port 215 and vent port 225 locations may be switched. In another embodiment, the ports 215, 225 may be positioned along another line, e.g., a vertical line, a horizontal line, or angled line, across/through and relative to the membrane 220. Accordingly, the illustrated locations of the ports 215, 225 is not meant to be limiting.

According to some embodiments, sample processing card 210 may include one or more air vents (or air ports) therein that may be used to vent and/or pull air therethrough. In some cases, vent port 225 may act as the air vent, while in other embodiments, air vent may be a separate port. In an embodiment, the air vent and/or vent port 225 may be configured to allow air flow to dry the contained fiber membrane (e.g., a glass fiber membrane). In one embodiment, the air vent may be normally closed via a valve, whose position (open or closed) may be controlled by the pneumatic system 330 (e.g., via connection to a designated port 235 and communication channel(s)).

From this sample injection area, the separated test sample within receiving area 224/sample chamber is designed for use and, optionally, mixing with a reagent, buffer, magnetic beads, etc. More specifically, the separated test sample is configured to be moved within the card 210 to prepare the test sample and then direct it to a GMR sensor chip 280 for sensing and outputting results to a user/operator. Fluid communication channels may fluidly connect the injection port 215 and receiving area 224 to a mixing material source and/or metering chamber(s), and/or other features within the card 210, as described in greater detail below.

In the illustrated sample processing card 210A of FIG. 5, for example, in accordance with an embodiment, the card 210A may be configured to have features that are similar on either side (left and right) of a longitudinal centerline A-A (provided in the Y-direction) when viewed overhead (see FIG. 5), and thus are mirror images of each other. Accordingly, the sample processing card 210A of FIG. 5 provides assay areas that are split and arranged in a parallel manner, allowing multiple assays at one time. In FIG. 5, similar reference numbers are used to represent features provided on both sides (i.e., left and right) of the sample processing card 210. As will be further evident based on the description below, such a structural arrangement on the sample processing card 210A of FIG. 5 allows for better mixing of the test sample (e.g., plasma) and reagent, buffer, magnetic beads, etc., along with use of control mechanisms (from unit 100), thereby resulting in better functioning of the card and thus higher assay specificity.

In accordance with an embodiment, some of the mechanisms used to control fluid mobility and mixing of the separated test sample in the sample processing card 210 are a series of valves provided in the valve array zone 230 as well as pneumatic control ports 235 in the pneumatic control interface. For example, plasma that is separated from a blood sample using the filtration membrane 220 in the receiving area 224 may travel through a sample delivery channel that extends from the receiving area 224 (in this case, from a center, bottom portion thereof) via controlling such valves and ports using a controller and/or pump(s) of pneumatic system 300 that may be connected to the sample processing card 210 and cartridge assembly 200, in accordance with one embodiment.

In accordance with embodiments herein, any of the embodiments of the sample processing card 210 may be configured to be positioned as part of the cartridge assembly 200 such that pneumatic control ports 235 of the pneumatic control interface are provided at an end of the card 210 that is first placed into the cartridge receiver 130 of the cartridge receiver unit 100. More specifically, while the Figures may generally depict ports 235 (or their interface) a bottom end or area of the card 210 when viewed longitudinally (e.g., with injection port 215 near a top of the card and ports 235 near a bottom), this bottom end of the card 210 with the pneumatic control ports 235 may actually be referred to herein as a "front end" or an "insertion end", when referring to insertion of the cartridge assembly 200 into unit 100.

It should be noted that although a single sample delivery channel may be shown in some of the embodiments in the Figures, it is envisioned that two or more sample delivery channels may be provided in the sample processing card 210. For example, in an embodiment, two or more sample delivery channels may extend from the receiving area 224 to another features within the card (e.g., metering chambers 240).

A series of valves may be provided in the valve array zone 230, in accordance with an embodiment. In an embodiment, a first set of valves is provided in the housing and includes a first valve and a second valve that are each configured for movement between an open position and a closed position. In one embodiment, a second set of valves is also provided in the housing, each valve being configured for movement between an open position and a closed position. Valves may be separated and may be provided on either side of the longitudinal centerline A-A of the card, in an embodiment. In another embodiment, the valves may be separated into rows, e.g., a row of first valves extending parallel to a row of second valves. The row of first valves may be positioned longitudinally above the row of second valves, for example. In an embodiment, the valves and valve array zone 230 may be provided adjacent to or relatively longitudinally below the filtration membrane 220 (relative to and along the centerline) within the card 210. In accordance with an embodiment, a series of valves may be provided in the valve array zone 230 relatively below the filtration membrane 220 in the vertical (Z) direction. In another embodiment, the valves may be provided on the same side of a longitudinal axis or centerline A-A of the housing. In yet another embodiment, valves may be provided in the valve array zone 230 relatively above the filtration membrane 220 in the vertical (Z) direction. As such, it should be understood that a location of the valve array 230 with respect to the filter 220 along the card (longitudinally) and/or within the layers of the card is not critical for the micro fluidic communication channels, as the fluid may be routed any number of places (vertically and/or longitudinally) on the card 210 via the channels therein.

Figure 6:
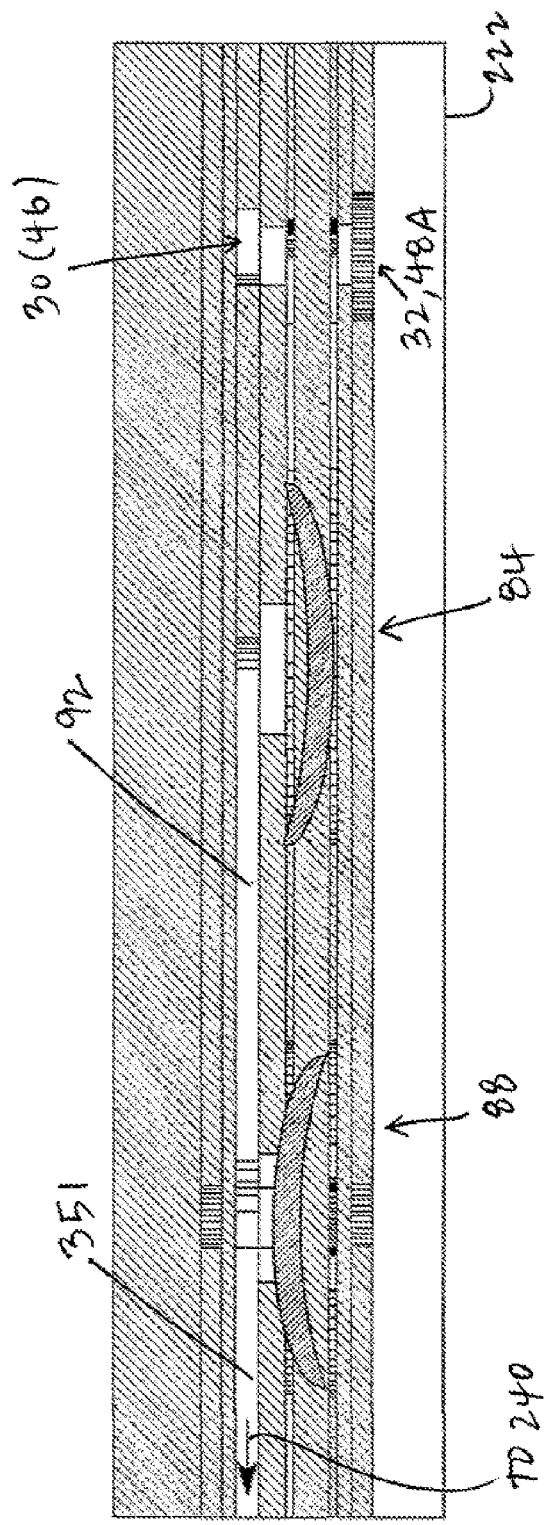
FIG. 6 is a schematic of a cross-section of the sample processing card of FIG. 5 and/or any of the sample processing cards according to any of the illustrated embodiments herein, illustrating an example of positioning of the valves in a first state.
Figure 7:
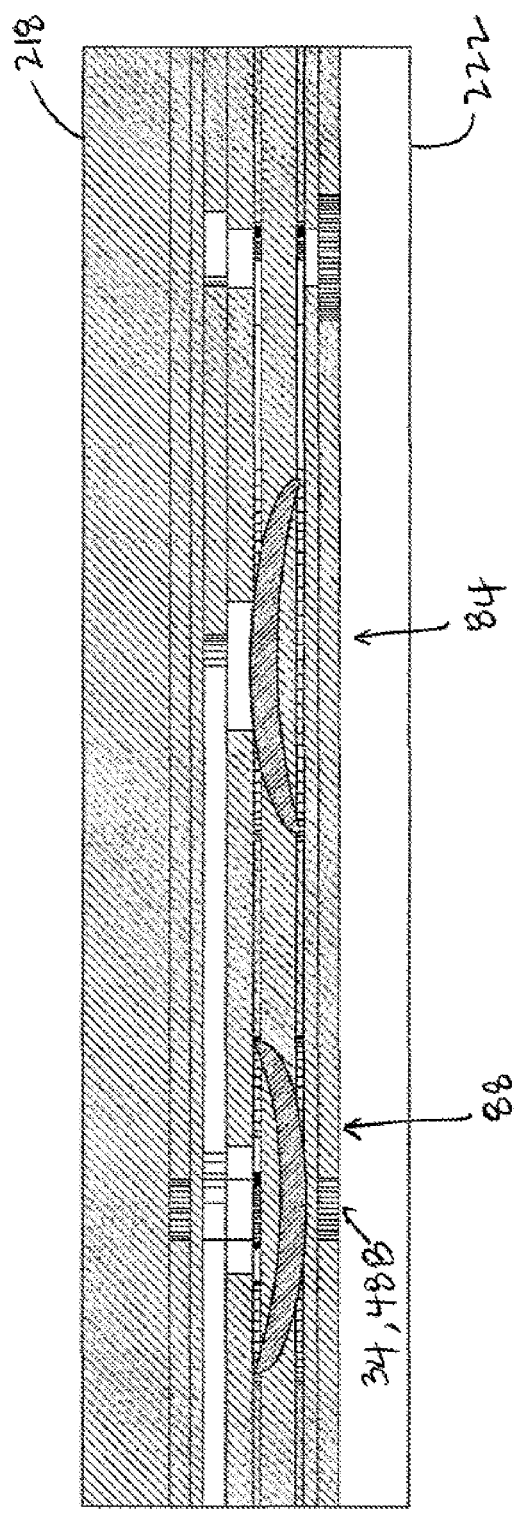
FIG. 7 is a schematic of a cross-section of the sample processing card of FIG. 5 and/or any of the sample processing cards according to any of the illustrated embodiments herein, illustrating positioning of the valves in a second state.

In one embodiment, each valve array zone 230 may include, or be formed from, an elastomeric material 212. As illustrated in the exemplary illustrated embodiment of FIG. 5, the location of the elastomeric material 212 is represented by generally rounded rectangle section, which may be provided below the top surface 218 and at a depth within the sample processing card 210, for example. An example of the positioning of the elastomeric material 212 at a depth or in an intermediate layer of the card 210 is shown in greater detail in FIG. 6 and FIG. 7. The elastomeric material 212 may be placed within a body of the sample processing card 210 such that valves that are formed in layers or within the body of the card. The elastomeric material 212 may include pockets and/or elastomeric deflection portions (as shown in FIGS. 6-7) that are/act as the valves, which are aligned with interior channels within the card. Movement of the deflection portions via positive pressure (e.g., pressurized air or vacuum from pneumatic system 330) between open and closed positions allows fluid (plasma, reagent) to move within the channels and housing parts, as described below.

The valves (i.e., elastomeric deflection portions) in the valve array zone 230 may be selectively controlled to allow for selective delivery of the separated test sample from the whole sample and/or a reagent, wash buffer, beads, etc. for mixing with the plasma to fluid metering chamber(s) 240, for example. As detailed later, controller(s) and/or pump(s) of pneumatic system 300 that are connected to the cartridge assembly 200 (and thus sample processing card 210) may be activated to control a position of the valves in the elastomeric materials 212/zone 230 and/or to apply positive and/or negative pressure (suction or vacuum) to the sample processing card 210 such that, depending on the positioning of the valves, the fluids (plasma and/or reagent) move within and throughout channels provided in the sample processing card 210.

In an embodiment, to move and deliver a separated test sample into the metering chambers 240, the sample delivery channel (from receiving area 224) may connect to any number of branch portions, which may channels that branch to a particular metering chamber 240. In one embodiment, two or more branch portions are provided. In an embodiment, such as shown in FIG. 5, branch portions may extend to one or more of the valve array zones 230 (on either side of the centerline A-A), for example. Also connected to valve array zones 230 in FIG. 5, via delivery channels, are reagent sections 260. The reagent sections 260 may be designed to receive a reagent therein. In one embodiment, these sections 260 are provided in the housing of the sample processing card 210 in the form of substantially rounded or circular well that receives and contains a volume of reagent therein. The reagent may be in the form of a liquid, fluid, or solution, that is metered from each of the sections 260 through delivery channels via activating valves/controllers, such that it is combined with the separated plasma from the blood sample, described later below. A volume of reagent may be injected into (via a user or the cartridge reader unit 100), pre-loaded, or stored in the reagent sections 260 in the sample processing card 210. In one embodiment, the reagent may be stored in the sections 260 of the sample processing card 210 using a blister pack configuration, i.e., the reagent is contained in the card and a seal is broken when testing of a sample takes place. In another embodiment, the reagent may be injected into the sections 260 and temporarily stored in the well/section until the valves/controllers are activated. Similarly, optional blister packs 265, wells, and/or storage chambers 285 (see, e.g., FIGS. 15, 17A, and 18A) may be provided on the card 210 to introduce materials such as reagents, wash buffers, magnetic nano particles, bead solution, or other buffers to the separated test sample during processing. Such blister packs 265 and/or storage chambers 285 may be designed to store and/or hold any number of items used in a preparing a sample, including, for example, enzymes, beads, etc. Storage chamber 285 may also or alternatively be designed to store or capture a portion of a sample, including, for example, capturing beads.

In addition to selectively moving the test sample, then, the valves in valve array zone 230 (along with pneumatic system 330 connected to ports 235 and/or valve control ports 535) may further control delivery and mobility of the reagent, buffer, beads, etc. in the sample processing card 210, i.e., into the fluid metering chambers 240.

The reagent or reagent solution may be one including magnetic nanoparticles to label target proteins. Generally, the reagent or reagent solution is configured to include an antibody that causes a mechanical reaction. In some embodiments, a sample is contacted with one or more suitable cell lysis reagents. Lysis reagents are often configured to lyse whole cells, and/or separate nucleic acids from contaminants (e.g., proteins, carbohydrates and fatty acids). Non-limiting examples of cell lysis reagents include detergents, hypotonic solutions, high salt solutions, alkaline solutions, organic solvents (e.g., phenol, chloroform), chaotropic salts, enzymes, the like, or combination thereof. Any suitable lysis procedure can be utilized for a method described herein. One or more wash buffers may be utilized to immobilize antibodies on a sensor surface and/or block ions, amplification, etc. on the sensor. Such types of reagents and buffers are known by one of ordinary skill in the art and thus all are not listed in detail here. The term "nucleic acid" refers deoxyribonucleic acid (DNA, e.g., complementary DNA (cDNA), genomic DNA (gDNA) and the like) and/or ribonucleic acid (RNA, e.g., mRNA, short inhibitory RNA (siRNA)), DNA or RNA analogs (e.g., containing base analogs, sugar analogs and/or a non-native backbone and the like), RNA/DNA hybrids and polyamide nucleic acids (PNAs), the like and combinations thereof. Nucleic acids can be single- or double-stranded. In some embodiments, a nucleic acid is a primer.

The fluid metering chambers 240 may be positioned beneath (in the Y-direction) the sample injection zone 10 in the card 210. In an embodiment, the fluid metering chambers 240 may be connected to channels (e.g., branch channels) that extend from receiving area 224, valve array zone 230, and/or any number of reagent, blister packs, and storage chambers, 260, 265, and 285, respectively. For example, in accordance with embodiments herein, each fluid metering chamber 240 may be configured to extend between the valve array zone 230 and a corresponding gas permeable membrane 245 in the longitudinal direction. Each of the chambers 240 (four are shown in FIG. 5) may be positioned at a depth within the housing, between the top and bottom surfaces 218 and 222, and in a manner such that they are parallel to one another in a lateral direction of the housing and extend a length in the longitudinal direction relative to the centerline A-A. Each chamber 240 is sized to receive metered fluids—e.g., a volume of separated test sample (plasma) and a volume of a mixing material (e.g., reagent, buffer, beads from a mixing material source, such as a blister pack, storage chamber, etc.)—therein, such that they may be mixed and used for testing (e.g., biomarker sensing, analyte sensing) via GMR sensor chip 280. As described in greater detail below, an open state for some of the valves allows for both the patient (plasma) sample and mixing materials(s) to separately be pulled into the fluid metering chambers 240 until the fluid(s) reach the gas permeable membranes 245. In accordance with an embodiment, the structural design of the channels in the sample processing card 210 and mixing material(s) may be mixed from dry powder, liquid mixture, gel, or other mixture. Each chamber 240 may be further configured to output the received fluids through connected channels, e.g., based on the output of the pneumatic system 330.

Figure 11:
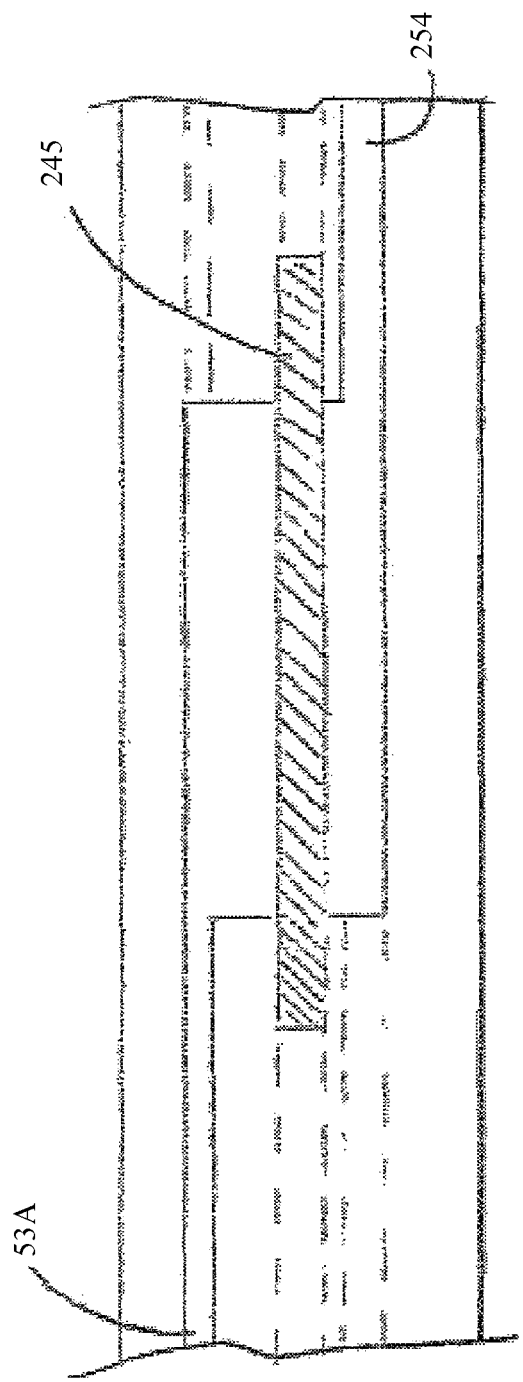
FIG. 11 shows a cross-sectional view of the sample processing card of FIG. 5 and/or any of the sample processing card according to any of the illustrated embodiments herein, in accordance with an embodiment.
Figure 12:
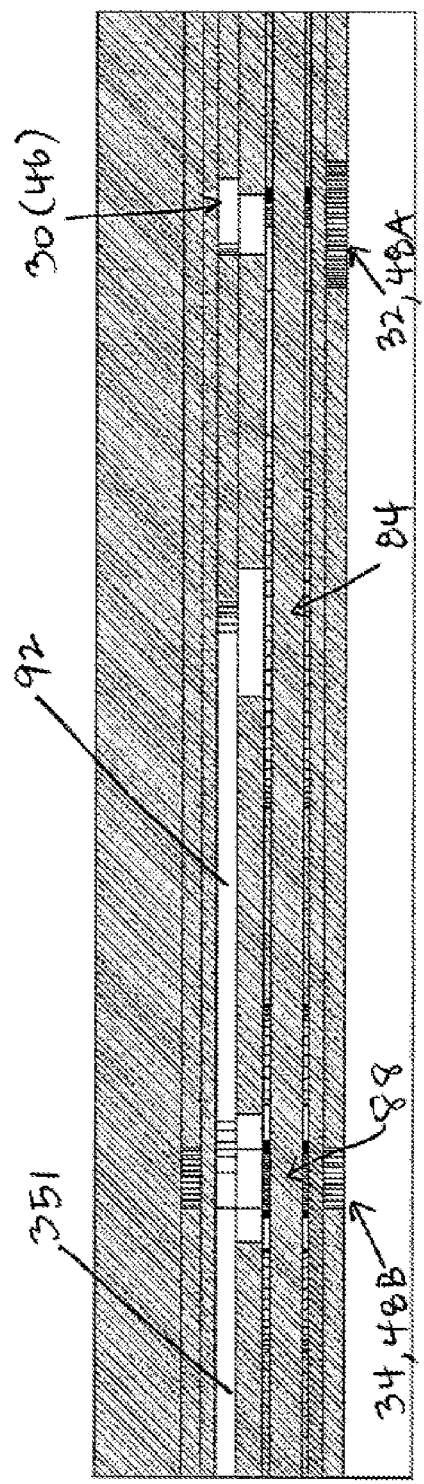
FIG. 12 shows a cross-sectional view of the valve array in the sample processing card of FIG. 5 and/or any of the sample processing cards according to any of the illustrated embodiments herein, in accordance with an embodiment.

The gas permeable membranes 245 are provided at a depth within the housing, such as shown in the cross section of FIG. 11. The gas permeable membranes 245 may be provided adjacent to and below the depth of the metering chambers 240 (e.g., in a layer below) in accordance with an embodiment. The gas permeable membranes may be fluidly connected to metering chamber(s). Each gas permeable membrane 245 may receive and deliver atmospheric air into the housing. The gas permeable membranes 245 may be formed from a membrane or material that is configured to receive, pull, or deliver atmospheric air into the housing of the sample processing card 210 while also being configured to prevent fluid(s) from entering into communication channels that are connected to pneumatic control ports 235. In an embodiment, the membranes 245 are used to pull air to a certain pressure through and into chambers 240. More specifically, a pump (fluidly connected to cartridge assembly 200) may be configured to generate negative pressure (vacuum) to pull fluids through a card 210, e.g., from metering chamber(s) 240 towards and to the gas permeable membrane(s) 245, which may also include pulling air through said membranes 245 (in addition to pulling through a communication channel connecting the metering chamber 240 and the gas permeable membrane 245). In an embodiment, the pump may be configured to stop application of negative pressure once the test sample/fluids/solution hits a gas permeable membrane(s) 245. In an embodiment, when the fluids reach the gas-permeable membranes 245, it may be determined in any number of ways, e.g., it may be sensed using a detector, determined based on a known volume of the chambers 240, and/or based on a predetermined amount of time for applying negative pressure (suction or vacuum) to the fluid chambers 240 (e.g., through a connected and corresponding communication channel) for metering the fluids. The gas-permeable membrane 245 may be provided in the form of a piece of adhesive film that is sandwiched between layers and provided in a pocket, for example. Fluid may be pulled to the top surface until it is whetted, providing the hard stop for the fluids pulled into the chambers 240.

Extending from the gas-permeable membrane 245 may be communication channels 254 that are connected to a pump interface, i.e., pneumatic control ports 235. In accordance with an embodiment, the communication channels 254 may be provided at a depth within the housing that is below the GPMs 245 and metering chambers 240 (see, e.g., FIG. 11).

As schematically depicted in FIG. 3, the pneumatic control (pump) interface includes a number of pneumatic control ports 235 that connect to one or more pumps or valves in a pneumatic system 330 (provided offline of the cartridge assembly 200, and thus the card 210, and within the cartridge reader unit 100). In the general context, each of the pneumatic control ports 235 are associated with a pressure switch. The supply to each of the pneumatic control ports 235 may be controlled or switched to apply positive pressure or negative pressure (suction or vacuum) to the ports 235, or no pressure at all, and thus apply such pressure the fluid metering chambers 240 and communication channels (e.g., like channel 433) in the card 210. In embodiments, the pneumatic control ports 235 and/or separate valve control ports 535 may be provided to control a position of valves in the valve array zone 230. Based the position and switching of the pump(s) and valves therein, then, fluids may be moved throughout the sample processing card 210, and mixed and delivered to the sensing device (GMR sensor chip 280). Such details are explained throughout and later.

Turning back to the valve array zones 230, in accordance with an embodiment, each valve array zone 230 may comprise a first set 80 of valves and a second set 82 of valves. As shown in greater detail in FIG. 8, the first set 80 of valves may be provided in first (e.g., upper) row and the second set 82 of valves may be provided in a second (lower) row in the valve array zone 230. The valves in both sets 80, 82 may be controlled using a valve actuation interface 530 (or controller interface). The sets 80 and 82 may be formed in the elastomeric material 212, e.g., via laser cutting or molding, for example, in the form of elastomeric deflection portions (see, e.g., FIGS. 6 and 7 and description later, for examples of such deflection portions). Although the sets 80 and 82 are shown in the embodiment of FIG. 5 to include two valves each that are positioned as part of an array 230 on either side of a longitudinal axis or centerline A-A (e.g., four valves for each set, i.e., a total of eight valves), it should be noted that, in other embodiments, the valve array zone 230 may include a series of valves, wherein the sets 80, 82 arranged in rows laterally across the card 210 (see, e.g., FIGS. 14, 17A, 18A, etc.). In one embodiment, a single valve for each set may be provided (i.e., a total of four valves). Additionally, the use of the term "set" is not intended to be limiting to the same type of valve. In an embodiment, a first valve 80 and a second valve 82 may be referred to as a "set."

Figure 8:
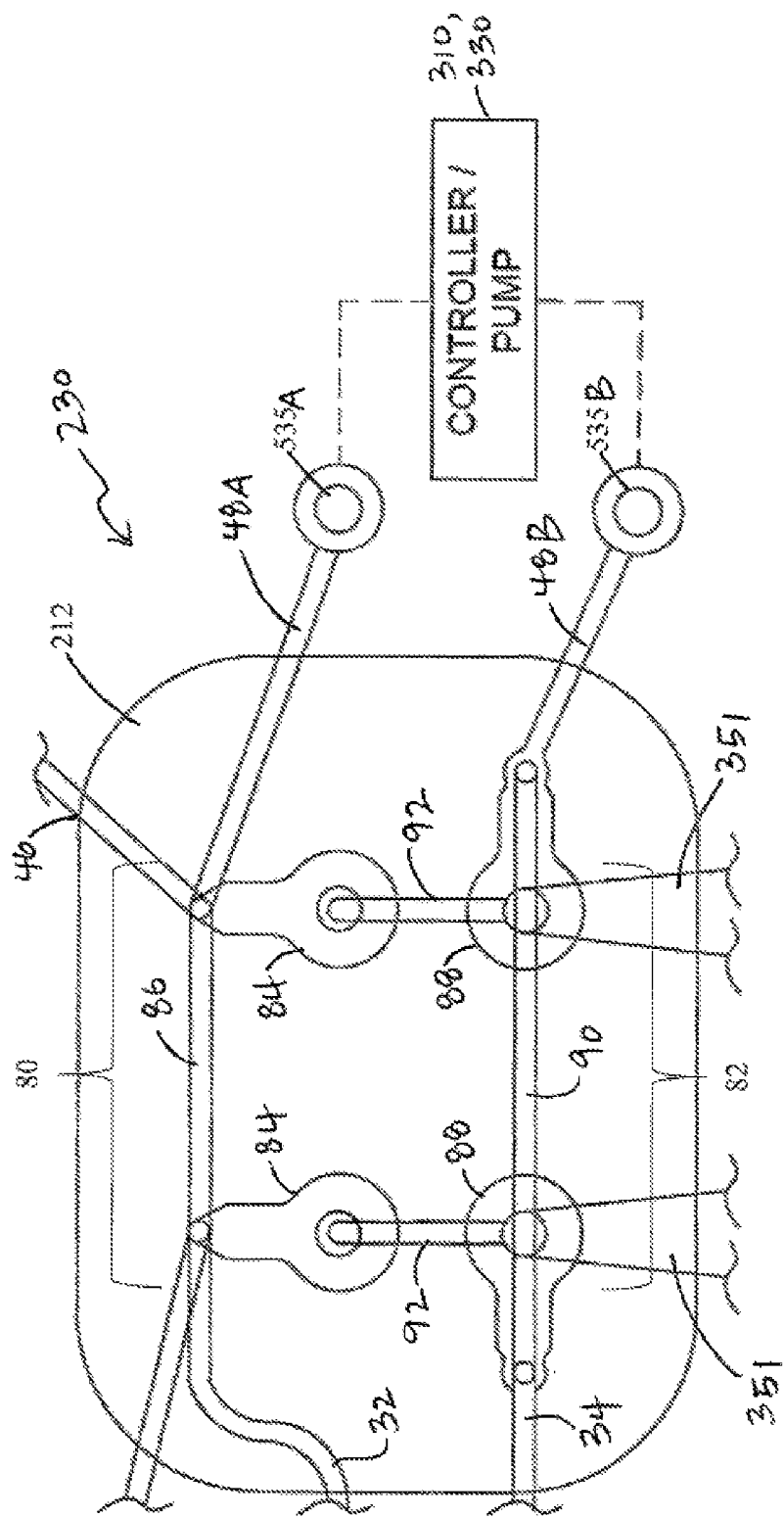
FIG. 8 is a detailed view of an exemplary valve array provided in the sample processing card of FIG. 5 and/or any of the sample processing cards herein, in accordance with an embodiment.
Figure 18A:
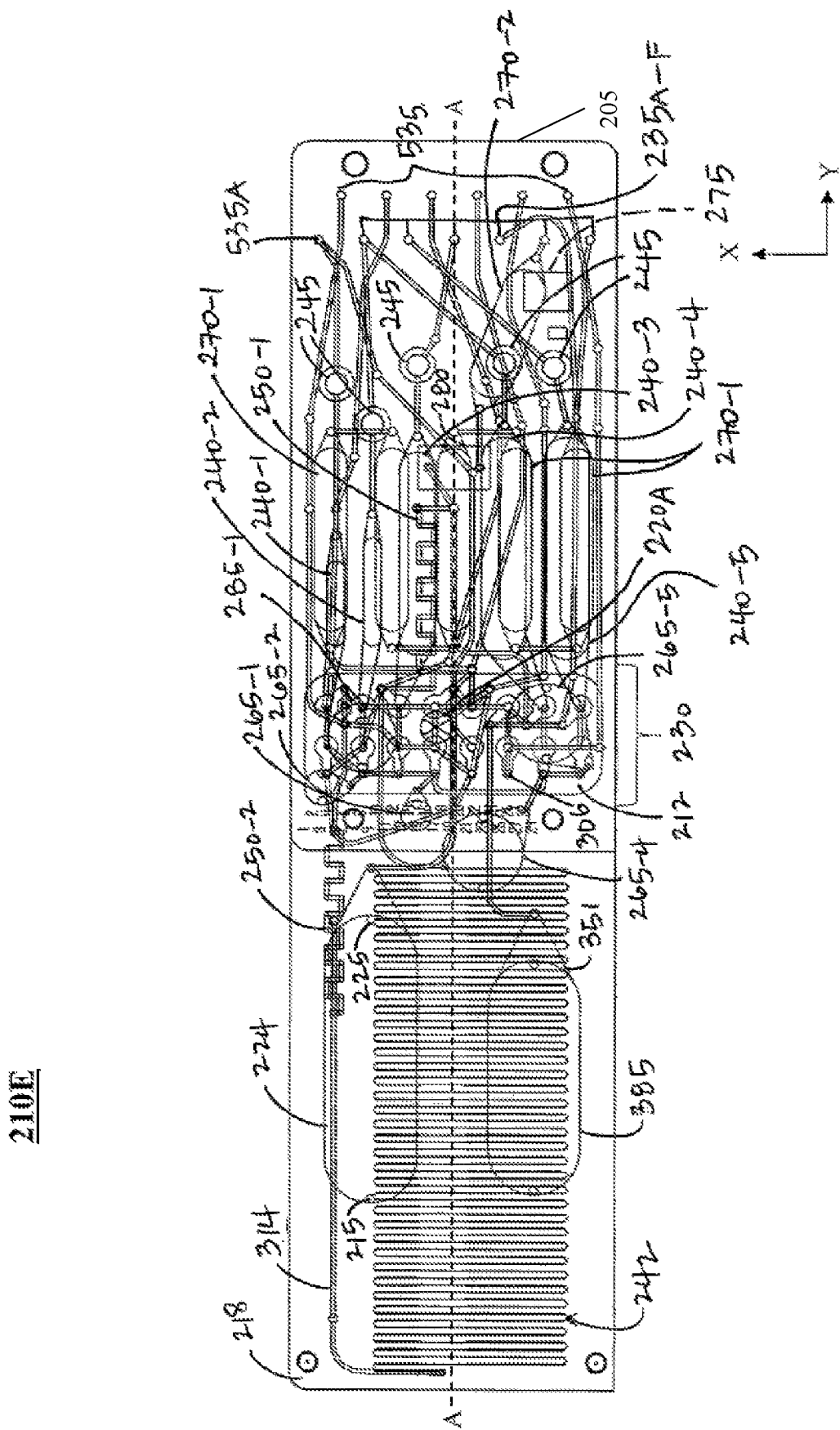
FIG. 18A shows a top view of a sample processing card configured for use in a cartridge assembly that uses a high-salt solution with a swab sample, in accordance with an embodiment herein.

The valve actuation interface 530 includes ports and control channels for selectively opening and closing the sets of valves in the valve array zone 230. Specifically, FIG. 8 shows a detailed view of one embodiment of the valve array zone 230 provided on the right side of the sample processing card 210A in FIG. 5, with valve actuation interface 530 connected thereto. However, it should be understood that the valve array zone 230 on the left side of the sample processing card 210A in FIG. 5 is substantially a mirror image of the valves on the right side, as depicted by the use of similar reference numerals in the drawings. Additionally, the location of the valve actuation interface 530 is not limited to what is illustrated in the drawings. In one embodiment, the valve actuation interface 530 may be provided on an opposite (left) side of the sample processing card 210A. In another embodiment, the valve actuation interface 530 may be provided on both sides of the sample processing card 210. In yet another embodiment, as shown in FIG. 18A, for example, the valve actuation interface 530 may be provided at a front end of the card 210, on either the top surface 218 and/or the bottom surface 222 of the housing, and adjacent to pneumatic control ports 235. Of course in still yet another embodiment, pneumatic control ports 235 may be utilized (along with connected channels) as the valve actuation interface 530.

The first set 80 of valves may include a series, a row, or a number of valves 84 (e.g., two or more) that may be fluidly connected together via first channel 86, in accordance with an embodiment. This first channel 86 may also be connected to one of the branch portions for fluid communication therewith (i.e., to receive separated plasma). In another embodiment, a branch portion may be directly connected to a pocket associated with the valve 84. The second set 82 of valves may include a series, a row, or a number of valves 88 (e.g., two or more) that are fluidly connected together via second channel 90, in accordance with an embodiment. Additionally, as seen in FIG. 8, for example, a connecting channel 32 may extend (laterally) between valves of the first set 80 (e.g., on either side of the centerline A-A) to communicatively and fluidly connect the valves 84 on the two sides. Connecting channel 32 may deliver pressurized air to each valve 84 provided in the sample processing card 210, for example. Similarly, a connecting channel 34 may extend (laterally) between the second sets 82 of valves for communicatively and fluidly connecting the valves 88 of the second set 82 (e.g., on either side of the centerline A-A). Connecting channel(s) 34 may also allow communication between metering chambers 240 and mixing channels 250, when valves 88 are in an open state. Connecting channel(s) 34 may be in fluid communication with second channel 90 and metering chamber 240 via transition sections 351, as noted below. Further, mixing channels 250 may be provided laterally between valves and fluid metering channels 240, in accordance with one embodiment. As shown in the exemplary views of FIGS. 5 and 14, for example, the metering channels 240 connect to the valves in valve array zone 230 via transition sections 351 that are connected to or part of the metering channels 240. Of course, transition sections 351 may be used on the other side of the metering channels 240, as shown, or with any other feature in the card 210 (as described below).

As seen in FIG. 8, in accordance with an embodiment, also connected to first channel 86 may be a control channel 48A. Control channel 48A is connected to a control port 535A of the valve actuation interface 530. Connected to second channel 90 may be a control channel 48B that is connected to a control port 535B in the valve actuation interface 530. The control ports 42A, 42B of the valve actuation interface 530 are connected to one or more offline pumps or controllers (of pneumatic system 330, schematically depicted in FIG. 3) that are designed to open and close each of the valves 84 and/or 88, as needed, during processing of a test sample.

In accordance with an embodiment, the opening and closing of each of these valves 84, 88 is mediated by use of positive and negative pressure gradients generated offline using the controller(s) and a connection to the ports (ports 235 or ports 535 of the valve actuation interface 530). Again, in one embodiment, each of the valves 84 and 88 may be formed from a flexible elastomer or deflection portion that, based on an amount of force or pressure applied thereto, moves a state of each valve between its open and closed positions, shown in FIGS. 6 and 7. In accordance with an embodiment, each valve 84 and 88 may be configured to be in a normally open state or open position, at rest. Upon application of an amount of pressure (e.g., pressurized air), the noted valve may be moved to a closed position.

Figure 9:
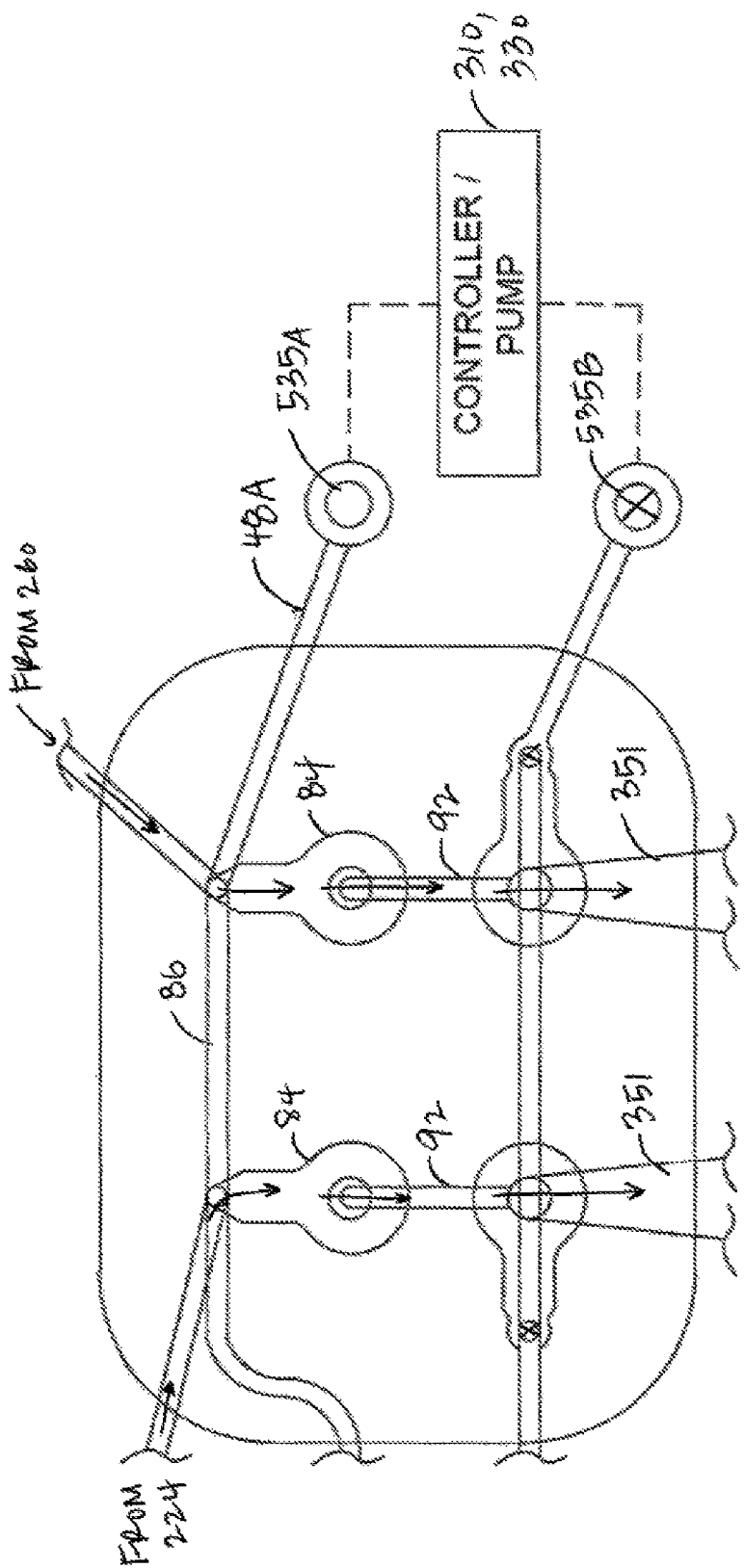
FIG. 9 is a detailed view of the valve array showing flow within channels in the first state, in accordance with an embodiment.
Figure 10:
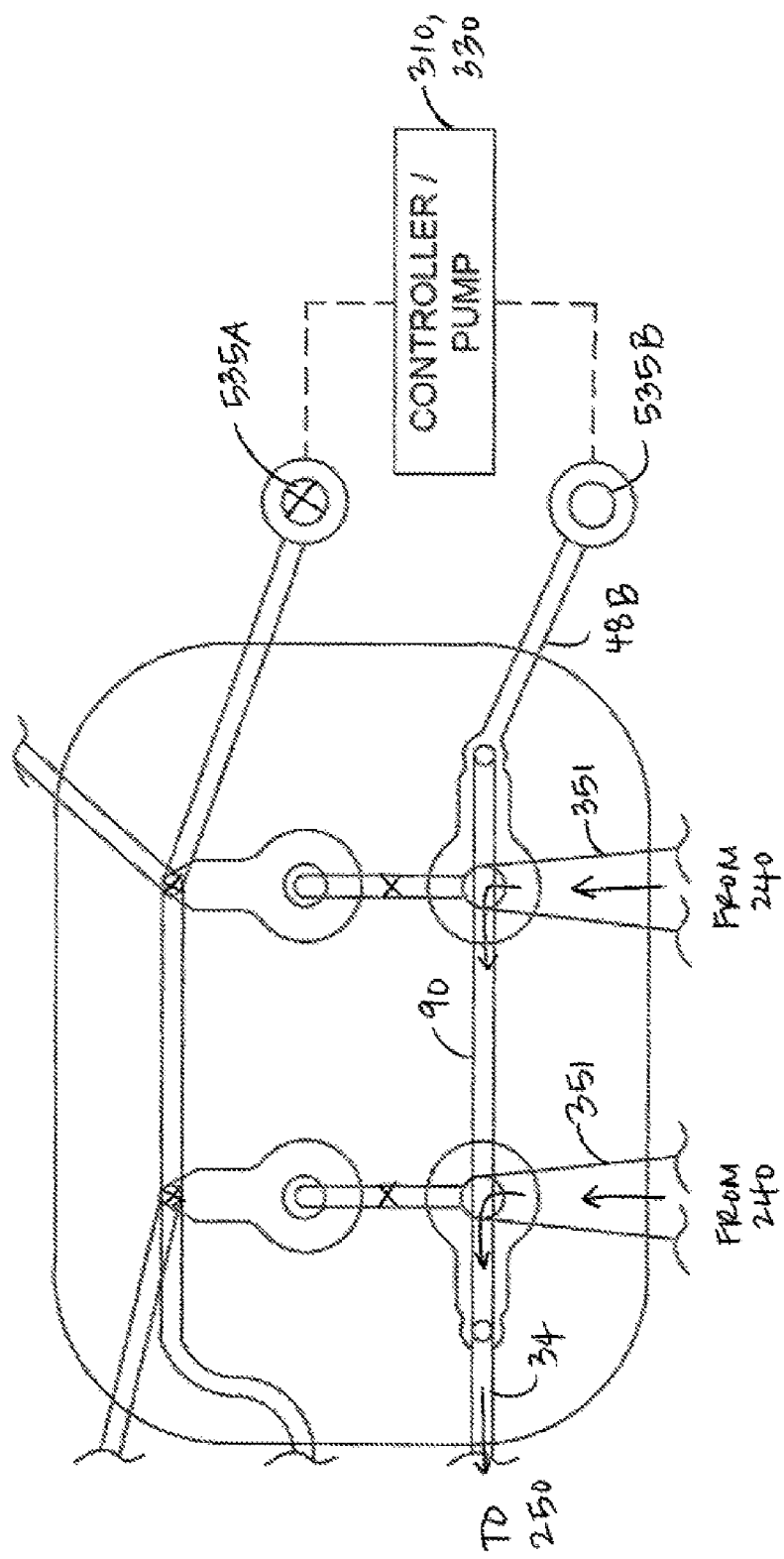
FIG. 10 is a detailed view of the valve array showing flow within channels in the second state, in accordance with an embodiment.

As shown in FIGS. 6 and 7, each of the channels connecting to the valves 84, 88 is positioned at a depth within the body or housing of the sample processing card 210. In an embodiment, the channels are formed within layers of the housing as it is manufactured. The positioning of the channels at different depths allows fluid to flow therethrough without interfering with other parts of the housing. For example, FIGS. 6 and 7 show a cross section taken in the valve array zone 230, showing the connection and positioning of the aforementioned channels (e.g., 92, 48A, 48B), and valves 84, 88 and their positioning within the housing (some of the lines illustrate exemplary layers that may be used to form the housing). The depths at which channels and valves are illustrated are exemplary only. Based on the state of the valves, the channels may be connected or blocked. That is, flow through the channels may be controlled based on movement of the elastomeric deflection portions relative to the channels, as activated by application of pressure via interface 530. For example, as shown in FIG. 6, in a first state, each valve 84 may be open, while valve 88 is closed (e.g., via pressurized air being applied to control channel 48B). Such features are represented here by arcs, to illustrate that the open valve 84 allows for fluid communication from and in communication channels, through valve 84 and channel 92, and into fluid metering chamber 240 via transition section 351. Fluid flow is blocked from delivery through valve 88 and into mixing channel 250. FIG. 9 schematically illustrates, for example, the movement of fluid in the first state of FIG. 6. In a second state, shown in FIG. 7, each valve 88 may be open, while valve 84 is closed (e.g., via pressurized air being applied to control channel 48A). Again, the positioning of the arcs illustrates that the open valve 88 allows for fluid communication from metering chamber 240 via transition section 351, through valve 88 and channel 90, and into mixing channel 250 (e.g., channel having a stepped configuration and connected to output ports 255). Fluid flow is blocked from delivery through valve 84 and through other communication channels. FIG. 10 schematically illustrates, for example, the movement of fluid in the second state of FIG. 7. As such, in accordance with an embodiment such as the one depicted in FIGS. 5 and 8, when each valve 88 is closed, fluid(s) may be directed towards fluid metering chambers 240. When each valve 88 is open, fluid may be directed towards mixing channels 250.

Alternatively, in accordance with another embodiment, the individual valves 84, 88 in each set 80, 82 may be individually controlled such that movement of fluid and/or materials may be directed through a specific area and one or more microfluidic communication channels, e.g., to a particular metering chamber 240. That is, fluid/materials may move through only certain channels and areas in the card, and do not necessarily need to move through all valves in a set or array zone. Such features shall be understood by the description with reference to embodiments shown in FIGS. 17A and 18A, for example.

In one embodiment, the amount of pressure/pressurized air applied to the interface 530 to move valve(s) 84, 88 between their open and closed positions may be within a range of approximately 2.0 psi to approximately 10.0 psi. In one embodiment, approximately 5.0 psi may be applied to the interface 42 to move the valve(s) between positions, i.e., from an open state to a closed state. Generally, the required amount of pressure for setting the state of the valves is small.

Figure 14:
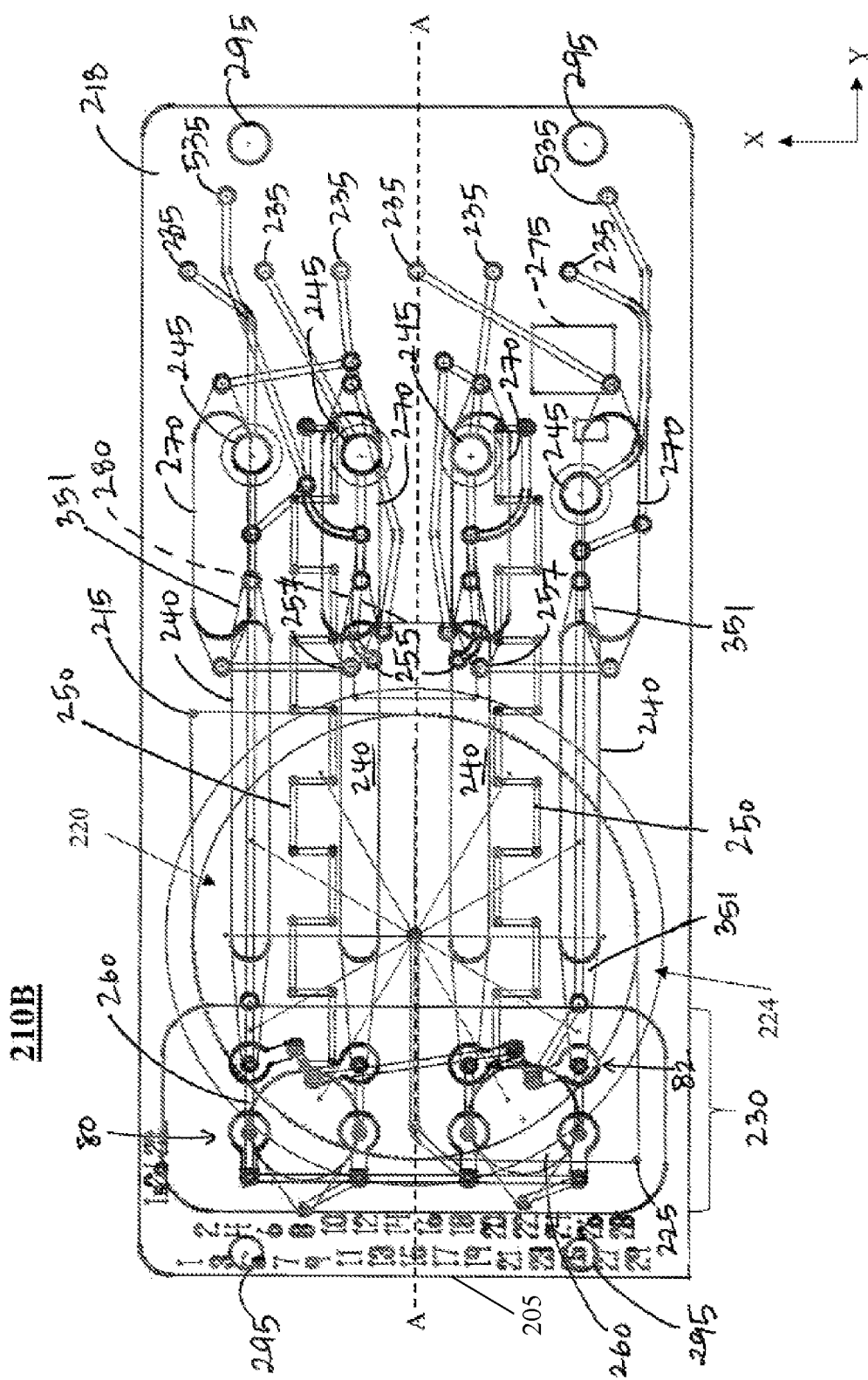
FIG. 14 is a top or overhead view of an exemplary assay or sample processing card for use as part of the cartridge assembly, in accordance with an embodiment herein.

Referring now to the other pneumatic features of the card 210, in an embodiment, connected to each metering chamber 240, e.g., via a connected, microfluid communication channel, may be one of the pneumatic control ports 235 that are configured to selectively draw and deliver pressurized fluid to (into) and from the housing. In another embodiment, each pneumatic control port 235 may connect (via connecting channels) to more than one metering chamber 240. The pneumatic control ports 235 may be a part of a pump interface that is provided in a lower portion (front end 205) of the body/housing, for example, such as shown in FIGS. 5, 14, and 17A. The pneumatic control ports 235 may be positioned relative to and accessed via the top surface 218, the bottom surface 222, or a combination thereof. In another embodiment, the ports 235 may be positioned on a side of the card 210. Generally, in the illustrated embodiments of FIGS. 14-27D, the pneumatic control ports 235 and the pneumatic control interface are shown as being provided in a top surface 218 of the respective cards 210, but such is for explanatory purposes only and not intended to be limiting.

The pneumatic system 330 of cartridge reader unit 100 is configured to be connected to the ports 235 at this interface, when the card 210 is inserted therein. In an embodiment, the pneumatic system 330 includes a pump that may be a different pump or a similar pump connected at the valve actuation interface 530. The pneumatic control ports 235 may be used to move and mix fluids throughout the channels in the housing of card 210. Depending on the state (open or closed) of the valves and the pump(s) connected at pneumatic control ports 235, the mixing channels 250 may allow for either or both of the test sample (plasma) and mixing materials(s) from a mixing material source to be pulled into fluid metering chambers 240 and/or pushed from said metering chambers 240 into mixing channels 250. Negative (suction or vacuum) pressure may be applied by pump to the pneumatic control ports 235, and/or to the valve control ports 535, may be configured to draw fluids (plasma, reagent) through the valves in valve array zone(s) 230, for example. Positive pressure (e.g., in the form of a pressurized fluid such as pressurized air) may be applied to pneumatic control ports 235, and/or to the valve control ports 535, to deliver fluids from the metering chamber(s) 240 to mixing channels 250, for example.

In accordance with an embodiment, as described above, in some embodiments, the fluid metering chambers 240 may also be fluidly connected to the second channel 90 via a transition section 351 provided at its top end, for example. In accordance with an embodiment, a corresponding transition section 351, may also be provided at a bottom end of each fluid metering chamber 240 near each gas permeable membrane 245. Transition sections 351 may be formed such that its width expands from a reduced width (near the valve array zone 230) to a width similar to that of the top/entrance of the chamber 240, and reduces in its width from the bottom/exit of the chamber 240 to a reduced width at its relative fluid line. The size and shape of the transition sections 351 are formed in this manner in order to reduce and/or prevent air bubbles from forming in the chambers 240. They further assist in providing smoother fluid flow when fluid is moved through the chamber 240.

Moreover, as shown throughout the Figures, transition sections 351 may be associated with other features in a sample processing card 210, including blister packs 265 and/or storage chambers 285, for example. Again, these transition sections 351 assist in directing materials (wet or dry) from a first feature to a second feature, thereby assisting in providing a smoother flow as material is moved within channels/areas of the card 210.

FIG. 5 shows the above-mentioned mixing channels 250 in greater detail, in accordance with an embodiment. Each of these mixing channels 250 may be used, in accordance with an embodiment, to mix, or, more specifically, further mix the metered test (plasma) sample and mixing material(s) that may be drawn into the chambers 240, which will be further explained below. The mixing channels 250 may be designed to mix or further mix the test sample and mixing material(s) into a substantially homogeneous or homogeneous mixture, for output and use in testing via GMR sensor chip 280. The mixing channels 250 may be provided such that they extend longitudinally (along Y-Y) within the body of the card 210, in accordance with an embodiment. Each of the mixing channels 250 may be connected at a first (input) end to a connecting channel and to another part in the card 210, e.g., a sensor delivery output port 255, at a second (output end), in accordance with an embodiment. The mixing channels 250 may be selectively connected to metering chambers, for example, and configured to deliver (by way of connected communication channels) a homogeneous mixture and/or a test sample and other mixing materials to the GMR sensor chip 280 via output port 255.

In accordance with the embodiments shown in FIGS. 5 and 14, two mixing channels 250 are provided in the cards 210A and 210B at a depth (or layer) below the metering chambers 240. The positioning of each mixing channel 250 may be such that it is provided adjacent to or near a middle or centerline A-A thereof, in accordance with one embodiment. For example, as shown in FIGS. 5 and 14, when two mixing channels 250 are provided, each channel may be provided on an opposite side of the longitudinal axis or centerline A-A, in accordance with an embodiment. In one embodiment, the mixing channels 250 may run generally parallel to one another on either side of the centerline A-A. In another embodiment, such as shown in FIG. 17A, the mixing channels 250 may be offset from one another on either side of the centerline A-A. In yet another embodiment, such as shown in FIG. 18A, mixing channels 250 may be provided on the same side of a centerline A-A (e.g., on a right side) of a sample processing card 210. In yet another embodiment, the one or more mixing channel(s) 250 in a sample processing card 210 may extend diagonally, laterally, or at an angle relative to the centerline A-A. One mixing channel 250 may be associated with more than one metering chamber 240, e.g., two chambers, in accordance with an embodiment.

In accordance with an embodiment, each of the mixing channels 250 may have a stepped configuration between its ends that includes portions that extend longitudinally (or vertically, or in the Y-direction) and portions that extend laterally (or horizontally, or in the X-direction) in the housing of the sample processing card 210. This stepped configuration enables the fluids to be moved through planes and induce turbulence in the fluids via its bends, to thereby blend and/or mix the fluids thoroughly into a substantially homogeneous or homogeneous mixture. In another embodiment, the mixing channel(s) 250 may include a zig-zag type configuration.

One or more output ports 255—also referred to as a sensor delivery port—is provided to output a prepared sample (e.g., a test sample mixed with mixing material in metering chamber 240) from the card 210 to a GMR sensor chip 280, as discussed below. Each of the ports 255 may be positioned at a depth within the card 210 and connected via a channel to another feature of the card, e.g., such that a test sample is directed from a metering chamber 240 and/or mixing channel 250, and towards bottom surface 222, where the GMR sensor chip 280 is located, in accordance with an embodiment. In an embodiment, the port(s) 255 may be provided in a lower portion of the card 210, e.g., at a front area (205) as shown in FIG. 5, for example. In another embodiment, the port(s) 255 may be provided in a center of a card 210. The ports 255 may be positioned relative to and accessed via the top surface 218, the bottom surface 222, or a combination thereof. In another embodiment, the ports 255 may be positioned on a side of the housing. In one embodiment, the sensor delivery ports 255 may be configured to output the fluid mixture through the bottom surface 222 of the card, and thus the ports 255 may be associated with or positioned adjacent to a sensor provided underneath the card 210. The ports 255 may be positioned on a location of the sample processing card 210 that cooperates and meets an inlet(s) of sensor(s) on such a device, so that the sensor(s) can detect and produce an output reading from the substantially homogeneous mixture that is output from the housing. The location of the ports 255 is not intended to be limiting. Generally, as previously described, the location of the port(s) 255 may depend upon the location of the GMR sensor chip(s) 280 provided as part of the cartridge assembly 200. For example, if multiple GMR sensor chips 280 are provided, multiple ports 255 may be positioned adjacent the chips 280. Output delivery via ports 255 is controlled using the valves 84, 88, pneumatic control ports 235, optional valve control ports 535, controller(s)/cartridge reader 310, and/or pump(s) and valve(s) of the pneumatic system 330.

In another embodiment, the sensor delivery ports 255 may be configured to output the fluid mixture through the top surface 218 of the card, and thus the ports 255 may be associated with or positioned adjacent to a sensor provided above the sample processing card 210. For example, the sensor(s) may be provided on a handheld mechanism or system.

One or more internal waste chambers (also referred to herein as waste tanks or waste reservoirs) 270 may also be optionally provided on the card 210 to store waste from the test sample. For example, after a test sample is mixed with mixing material(s) in the metering chambers and directed to GMR sensor chip 280 (e.g., to flow over the chip 280 and/or through output ports 255 to the chip 280), it may be directed to and deposited into one or more of the waste chambers 270 provided in the card 210 (e.g., by directing the test sample through an input port 257 and/or channel(s) connected to the waste chamber(s) 270). Each of the waste chambers 270 may be positioned at a depth within the housing, between the top and bottom surfaces 218 and 222. In an embodiment, the waste chambers 270 may be positioned in a manner such that they are parallel to one another in a lateral direction of the housing and extend a length in the longitudinal direction relative to the centerline A-A. In another embodiment, the waste chambers 270 may be positioned at an angle relative to centerline A-A. In an embodiment, the waste chambers 270 are positioned in a layer or at a depth that is below the metering chambers 240 within the sample processing card 210. Channels may connect the metering chambers 240 to the output ports 255 to the GMR sensor chip 280, as well as connect input port 257 from GMR sensor chip 280 to the waste chambers 270. The fluid of the test sample may be removed to waste reservoirs 270 by applying negative pressure through pneumatic control ports 235 (through a connected (to pneumatic system 330) and corresponding communication channel), for example.

In some embodiments, a serpentine channel 242 may be provided in the sample processing card 210 of the cartridge assembly 200. The serpentine channel 242 may be used as part of a thermocycling and/or an amplification process of the test sample within the card 210.

The sample processing card 210 and/or cartridge assembly 200 may further include one or more alignment devices 295 therein, in accordance with an embodiment. In one embodiment, such as illustrated throughout the Figures, the alignment devices are provided in the form of alignment holes 295. In another embodiment, the alignment devices 295 may be provided in the form of protrusions or pins extending from the card 210 and/or assembly 200. The alignment devices 295 may be used to align the cartridge components during assembly of the card 210 (e.g., during assembly of its layers) and/or for seating and aligning the cartridge assembly 200 into and within the cartridge receiver 130 (e.g., into the receiving tray) of the cartridge reader unit 100. Alternatively, other structural features, such as cut-out portions or divots, for example, may be provided as alignment devices on the cartridge assembly 200. In another embodiment, a structural alignment device, such as a card stop wall or protrusion, may be provided inside of the cartridge reader unit 100 to act as an alignment device.

In accordance with an embodiment, the disclosed sample processing card 210 is configured for use as part of the cartridge assembly 200 which is provided for use in cartridge reader unit 100 and designed to provide technicians with convenient and fast analyte detection in a single process. The device may detect a level of analyte within an input blood sample, for example. In one embodiment, the system or device may be a handheld or mobile device or system configured to connect with or receive the cartridge assembly 200. For example, the card 210 may interface with a handheld system via a face seal using o-rings that are clamped down to the top of the card. This seal permits a negative pressure to be achieved that facilitates fluid movement throughout the card, as described with reference to FIG. 13 and method 600, in accordance with one embodiment. The mixture from sample processing card 210 may be output (or input) into the GMR sensor chip(s) 280 of cartridge assembly 200, and the presence of multiple biomarkers may be detected by capturing proteins from the mixture and quantifying their presence based on magnetic field detection. In an embodiment, the cartridge assembly 200 may employ one or more sensors configured to detect analytes in a mixture/sample by displacing competing analytes labeled with magnetic nanoparticles and sensing a change in the magnetic field created by the magnetic nanoparticles via a magnetic (field) sensor, e.g., a giant magnetoresistance (GMR) sensor chip 280 or other magnetic sensors (e.g., AMR, TMR, etc.). One or more sensors or an array of magnetic sensors may be formed on a chip, for example, so that multiple antigenic analytes are detected with specificity within the sample.

In an embodiment, the sample processing card 210 (in any of the embodiments disclosed herein) of a cartridge assembly 200 may be fabricated by stacking and laminating different types and layers of laser cut, polymer materials, to produce the described channel geometries and shapes shown in the Figures. In addition to these layers, the gas-permeable membrane 245, filtration membrane 220, and/or elastomer material 212 over zones 230 may also be laser cut and placed in designated regions of the sample processing card 210 to provide the required functionality. However, as noted throughout this disclosure, any number of manufacturing methods and/or materials may be used to manufacture the sample processing card 210.

Figure 13:
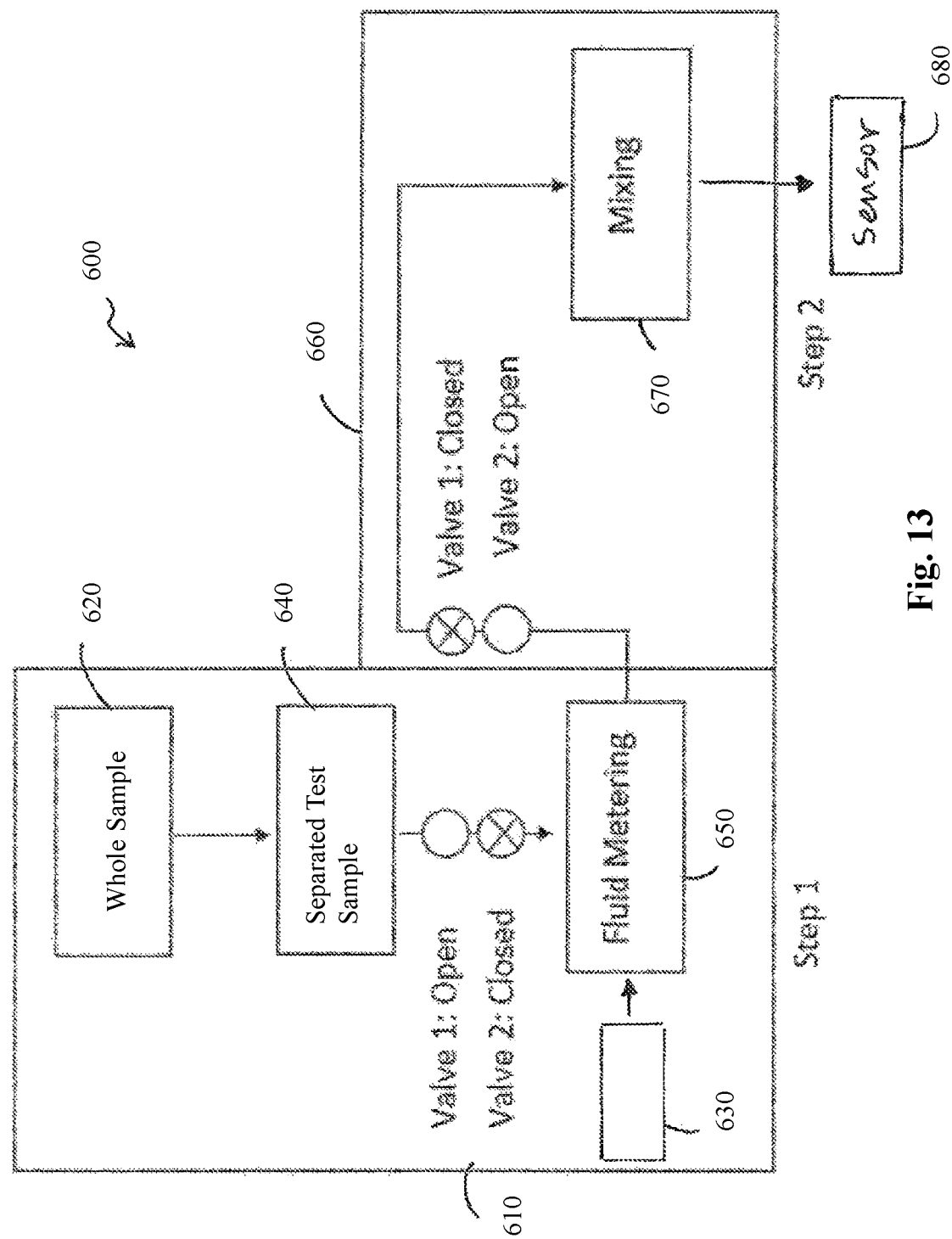
FIG. 13 is a flow chart of a method of using the sample processing card of FIG. 5 and/or any of the sample processing cards in a cartridge assembly along with the cartridge reader unit, in accordance with embodiments herein.

FIG. 13 is a flow chart of a method 600 of using the cartridge assembly 200, e.g., with a handheld system or cartridge reader unit 100, or another offline device or system, that is configured to connect to the cartridge interfaces (e.g., including pump interface and pneumatic control ports 235, any valve control ports 535, and sensor output interface) and substrate 202. For explanatory purposes only, reference to a single controller and pump (as part of the pneumatic system 330) is noted here, but is not meant to be limiting. In an embodiment, in a first state, a first set 80 of valves, valves 84, are in an open position, while the second set 82 of valves, valves 88, are in a closed position. In a second state, the first set of valves (84) are in a closed position, while the second set of valves (88) are in an open position.

In accordance with an embodiment, the method 600 of using the herein disclosed cartridge assembly 200 to mix a test sample follows steps of method 200. The valve states of the valves 84 and 88 are initially set as follows, as shown at 610: pump is attached to the valve interface (530, if provided, or pneumatic interface) and controlled and configured to apply positive pressure through valve interface via ports 42B and 48B to second channel 90, including through any connecting channels that may connect to valves on opposite side of the centerline A-A, such that valves 88 (Valve 2) are moved to a closed position. In an embodiment, no pressure is applied to first channel 86 and channel 32, and thus valves 84 (Valve 1) remain in an at rest/default state, i.e., an open position. In another embodiment, the pump may be controlled to position the valves 84 in an open state. A sample (which may be a whole sample) is input or injected at 620, e.g., into the injection port 215 of the sample processing card 210 of the cartridge assembly 200. Reagent(s), wash buffer(s), beads, etc.—i.e., mixing material(s)—may be optionally stored in or provided to the sample processing card 210, as shown at 630, and ready for mixing with the separated test sample, in accordance with one embodiment. As described in greater detail above, the mixing material(s) may be stored or added to the sample processing card 210, prior to the injection of the sample and/or after insertion of the cartridge assembly 200 into the unit 100. The test sample is (optionally) separated at 640 from the input whole sample, e.g., using filtration membrane 220. At the pump interface, a pump/pneumatic system 330 is also attached to the ports 235. Negative (suction or vacuum) pressure may be applied by pneumatic system 330 to the ports 235, thereby pulling the separated test sample and any mixing material(s) through the communication channels and/or into the fluid metering chambers 240, as shown at 650. For example, the vacuum pressure pulls the separated test sample and mixing material(s) from 260, 285 through branches or channels into metering chambers 240. This action may allow the two fluids to be forced into the mixing region in a 1:1 ratio. Alternatively, the fluids may be pushed and/or pulled at different times and at different ratios, depending upon the test being performed. Both fluids are metered or pulled until they reach the gas permeable membranes 245, for example.

After the metering at 650, the valve states in the valve array zone(s) 230 are switched, as shown at 660. The pressure from pump/pneumatic system 330 is reversed and controlled to apply positive pressure through valve actuation interface (530) (if provided, or alternatively, the pneumatic interface) via port 42A and control channel 48A to first channel 86, including through communication channels to other valves, e.g., on an opposite side of the centerline A-A, such that valves 84 (Valve 1) are moved to a closed position. In an embodiment, no pressure is applied to second channel 90 and connecting channel, and thus valves 88 (Valve 2) remain in an at rest/default state, i.e., an open position. In another embodiment, the pump may be controlled to position the valves 88 in an open state. The pump may also be controlled to apply positive pressure at the pump interface through ports 235, channels and gas permeable membranes 245, such that it moves or pushes the metered fluids (e.g., plasma and reagent) to and through second channels 90, and then into mixing channels 250. The continuous application of pressure through ports allows for mixing, as indicated at 670, of the fluids as they move through (e.g., the stepped configuration of) the mixing channels 250, to form a substantially homogenous or homogeneous mixture, e.g., of the test sample and any mixing materials (reagent). The mixed fluids exit or are output from the sample processing card 210, e.g., via output ports 255, to one or more GMR sensor chips 280 that is/are part of the cartridge assembly 200, as represented at 680. The sensor chip(s) 280 uses the mixed, homogeneous fluid to sense or detect a designated item, e.g., biomarkers, in the sample provided thereto.

At the end of the method, although not depicted in FIG. 13, the mixed fluid/sample may be directed to one or more waste chambers 270 provided in the sample processing card 210.

In an embodiment, the multiple biomarker reading from the GMR sensor chip(s) 280 may be performed and output (e.g., via the display 120) to the user.

Of course, while the description of method 600 may refer to valves 84 and 88 as being open or closed, this refers to one exemplary embodiment. That is, as previously described with reference to the valves, in some embodiments, individual valves may be controlled, e.g., in different stages, for moving fluid and/or materials through the card 210. Accordingly, reference to Valve 1 and Valve 2 in the method 600 is exemplary only, and not intended to limit the description of valves 84, 88 to mean that all valves in a set 80, 82 must be moved or changed at the same time.

In accordance with an embodiment, the total processing time from injection to output (out to sensor) of the method 200 may take approximately ten to twenty minutes, depending on the pump design and settings. However, the processing time may be altered and is not meant to be limiting.

In an embodiment, a test sample of approximately 500 mL or less of blood is configured to be injected into the injection port 215. In an embodiment, a test sample of approximately 300 mL of blood is configured to be injected into the injection port 215. In an embodiment, the filtration membrane 220 is configured to yield approximately 50 mL to approximately 250 mL of plasma. In an embodiment, the filtration membrane 220 is configured to yield approximately 100 mL of plasma.

In accordance with an embodiment, approximately 50-100 ml of reagent may be provided in the reagent injection sections and/or used in the sample processing card 210.

The herein disclosed sample processing card 210 uses interfaces, valves, and channels to allow for autonomous metering and mixture of (optionally stored on-board or provided thereto from unit 100) reagents with a patient blood sample that is input therein as part of a single application or process. The method 600 of using the disclosed microfluidics card 210 allows for a user to perform mixing of a sample as part of a single process, and analysis when used in conjunction with a device (sensor chip 280), so that multiple biomarkers features in the sample may be detected. The metering of the fluids and subsequent mixing operations are controlled entirely by off-cartridge pump(s) and controller(s) (pneumatic system 330 and cartridge reader 310, respectively) that are connected to the card 210 when the card 210 is inserted and connected to the cartridge reader unit 100, which allows for a complete automation of the assay process that previously required human technicians. The standardization of geometries and fluid movement also allows for a more stable platform, as more elements of the system are controlled.

Also, using this optionally disposable point of care cartridge assembly 200, a wider range of detection is possible while using a smaller amount of patient blood sample, without sacrificing speed in the production of results. For example, the disclosed assay cartridge assembly design permits the detection of multiple biomarkers from a single sample, and thus facilitates multiplex analysis of target biomarkers from a single patient sample. In a particular embodiment, the disclosed cartridge assembly 200 utilizes the patient blood sample for targeting multiple (e.g., five) biomarkers associated with cardiac distress.

Further, the structural features of the disclosed cartridge assembly 200 may permit multiple assays to run in parallel. Examples of such multiple assays are described below.

Further examples of sample processing cards used in cartridge assemblies in accordance with embodiments of this disclosure are described below. Although the description of FIGS. 14-27D below may not explicitly reference the description and illustrations and features shown in FIGS. 2A-2E and 5-13, it should be understood that each of the cartridge assemblies and/or sample processing cards illustrated and described with reference to FIGS. 14-27D may include and/or incorporate any number of similar functional aspects and features described with reference to the aforementioned Figures (or vice versa).

For purposes of clarity and brevity, like elements and components throughout the Figures are labeled with same designations and numbering as discussed with reference to FIGS. 1-13. Thus, although not discussed entirely in detail herein, one of ordinary skill in the art should understand that various features associated with the sample processing cards 210 and/or cartridge assemblies 200 of FIGS. 14-27D are similar to those features previously discussed. Additionally, it should be understood that the features shown in each of the individual figures is not meant to be limited solely to the illustrated embodiments. That is, the features described throughout this disclosure may be interchanged and/or used with other embodiments than those they are shown and/or described with reference to.

FIG. 14 illustrates one embodiment of a microfluidic chamber card or sample processing card 210B configured for use as part of a cartridge assembly 200. In an embodiment, this type of card 210B is configured for use with a blood-based sample. The sample processing card 210B may include features as previously described above with reference to FIGS. 5-12, and thus such details are not necessarily repeated here. One or more cut-out sections may be provided, e.g., on the bottom surface 222 in the card 210B, to accommodate receipt of a portion of the GMR sensor chip 280 and/or on-board memory chip 275 of the substrate 202. Exemplary locations of the chip 280 and memory card 275 relative to the additional features in the card 210B are generally shown. The filtration membrane 220 is provided or sandwiched at a depth between the top surface 218 and bottom surface 222. A patient test sample is configured to be loaded, introduced, or injected into the injection port 215. The sample is filtered via filtration membrane 220, i.e., to yield a separated test sample. The separated test sample may settle into a bottom portion of the sample chamber or receiving area 224 in the sample processing card 210B, e.g., provided adjacent to or below (in the vertical direction, i.e., direction of depth or height, in a Z-direction). Specifically, the illustrated lines in the filtration membrane 220 as shown in FIG. 5, for example, represent a structural, directional feature, such as channels, that are used to direct an injected whole blood sample to spread across membrane 220. In an embodiment, the depth of the vent port 225 extends from the (bottom of the) receiving area 224 to the top surface 218. Vent port 225 is open to the atmosphere and configured to vent air from the housing.

The sample processing card 210B as shown in FIG. 14 provides assay areas that are split and arranged in a parallel manner, allowing multiple assays at one time.

In accordance with this embodiment, a series of valves are provided in the valve array zone 230 relatively below the filtration membrane 220 in the vertical (Z) direction. For example, the elastomeric material in valve array zone 230 may be between a bottom 222 of the card 210B and a layer that holds filtration membrane 220. For example, plasma that is separated from a blood sample using the filtration membrane 220 in the receiving zone 224 may travel through a sample delivery channel that extends downward from the receiving zone 224 (in this case, from a center, bottom portion thereof) via controlling such valves and ports 235, 535 using a controller and/or pump(s) connected to the sample processing card 210B and cartridge assembly 200, in accordance with one embodiment. Also connected to valve array zone 230 via delivery channels are reagent sections 260, e.g., on either side of centerline A-A in FIG. 14. Reagent(s) may be metered from each of the sections 44 through delivery channels via activating valves/controllers, such that it is combined with the separated plasma from the blood sample, in any manner as described herein.

The separated test sample (e.g., plasma) may be directed through the first set 80 of valves and to metering chambers 240. The fluid metering chambers 240 may be positioned beneath (in the Y-direction) and connected to channels in the valve array zone 230. Also in the embodiment of FIG. 14, metering chambers 240 may be positioned in a layer (vertically, in the Z-direction, or at a depth) below the filtration membrane 220. As shown in FIG. 14, each fluid metering chamber 240 extends longitudinally between the valve array zone 230 and a gas permeable membrane 245 which is generally located near a front end of the card 210B. Each of the chambers 240 (four are shown here) may be positioned at a depth within the housing (in the Z-direction), between the top and bottom surfaces 218 and 222, and in a manner such that they are parallel to one another in a lateral direction of the housing and extend a length in the longitudinal direction relative to the centerline A-A. Each chamber 240 is sized to receive metered fluids—i.e., a volume of separated plasma (blood) sample and a volume of reagent—therein, such that they may be mixed and used for analyte/biomarker sensing. Extending from the gas-permeable membranes 245 are communication channels that are connected to a pump interface including control ports 235 and/or 535 (ports being provided, for example, on a top 218 of the card). In accordance with an embodiment, the channels are provided at a depth within the housing that is below the membranes 245 and chambers 240. The control ports 235 and/or 535 may be connected to pneumatic control system 330 (provided offline of the cartridge assembly 200 and thus the card 210B). The pneumatic control system 330 is configured to be controlled to apply positive pressure or negative pressure (suction or vacuum) to the ports 235 and/or 535, or no pressure at all, and thus apply such pressure the fluid metering chambers 240 and channels in the card 210B. Accordingly, fluids may be moved throughout the sample processing card 210B and mixed. In accordance with an embodiment, the fluid metering chambers 240 may also include transition sections 351, as previously described.

Once the mixed fluid reaches GPMs 245, the pressure into ports 235 and/or 535 may be adjusted (e.g., stopped, reversed) such that the fluid test sample may be pushed to mixing channels 250. Each of these mixing channels 250 may be used to mix or further mix the metered patient (plasma) sample and reagent that is drawn into the chambers 240. In accordance with an embodiment, two mixing channels 250 having a stepped configuration are provided in the housing of card 210B at a depth (e.g., layer) below the metering chambers 240. The positioning of each mixing channel 250 may be such that it is provided adjacent to or near a middle or centerline A-A thereof, in accordance with one embodiment. From the mixing channels 250, the test sample is directed to output ports 255 and to the GMR sensor chip 280 provided in the cartridge assembly 200. Output delivery via ports 255 is controlled using the valves 84, 88, ports 235, 535, and pneumatic control system 330 as described throughout this disclosure. Further provided in the illustrated embodiment of the card 210B of FIG. 14 are waste reservoirs 270. After the sample may flows towards and/or over the GMR sensor chip 280, it may further flow, e.g., via input ports 257 and connected channels, into waste reservoirs 270.

Figure 15:
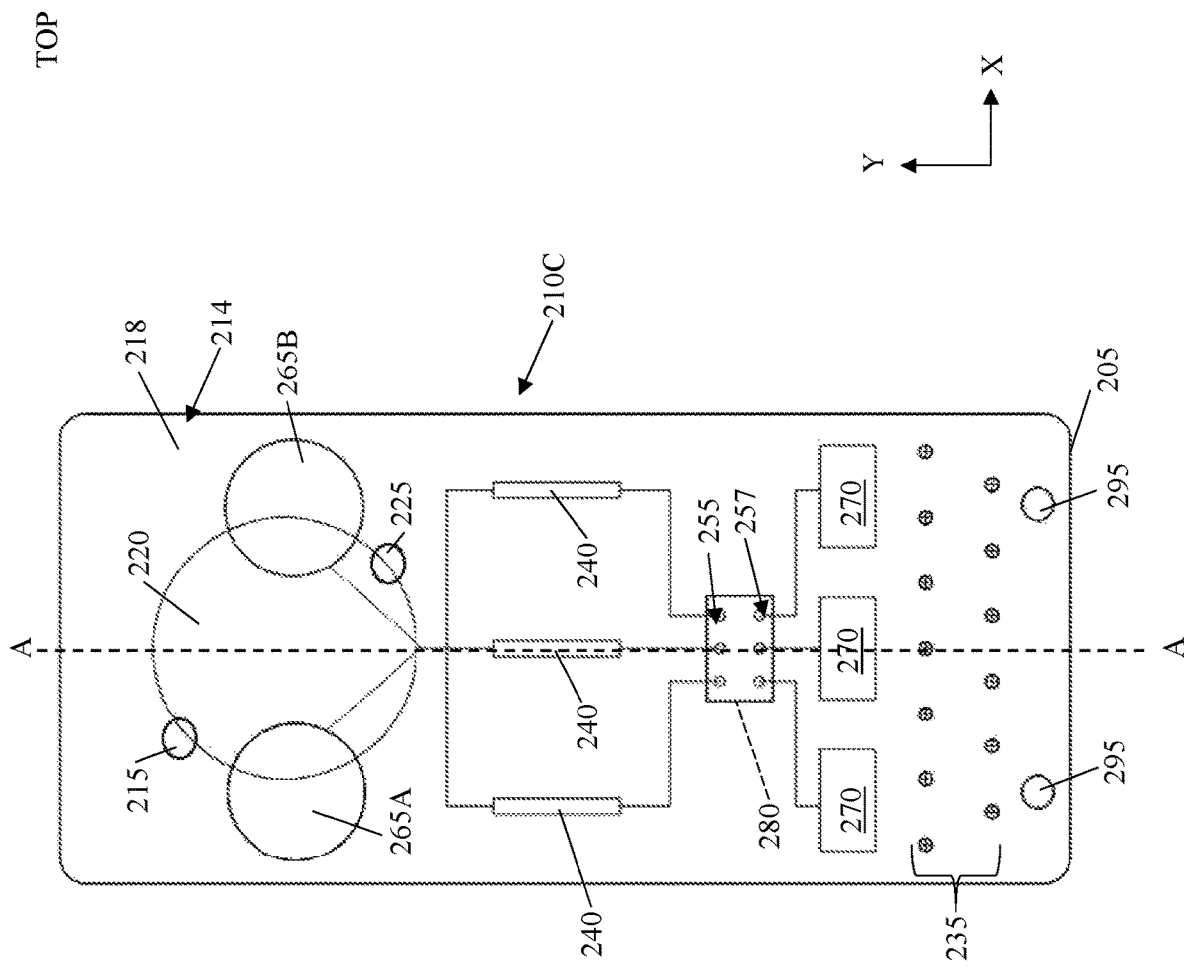
FIGS. 15 and 16 illustrate a top and a bottom, respectively, of an exemplary assay or sample processing card for use as part of the cartridge assembly, in accordance with an embodiment herein.
Figure 16:
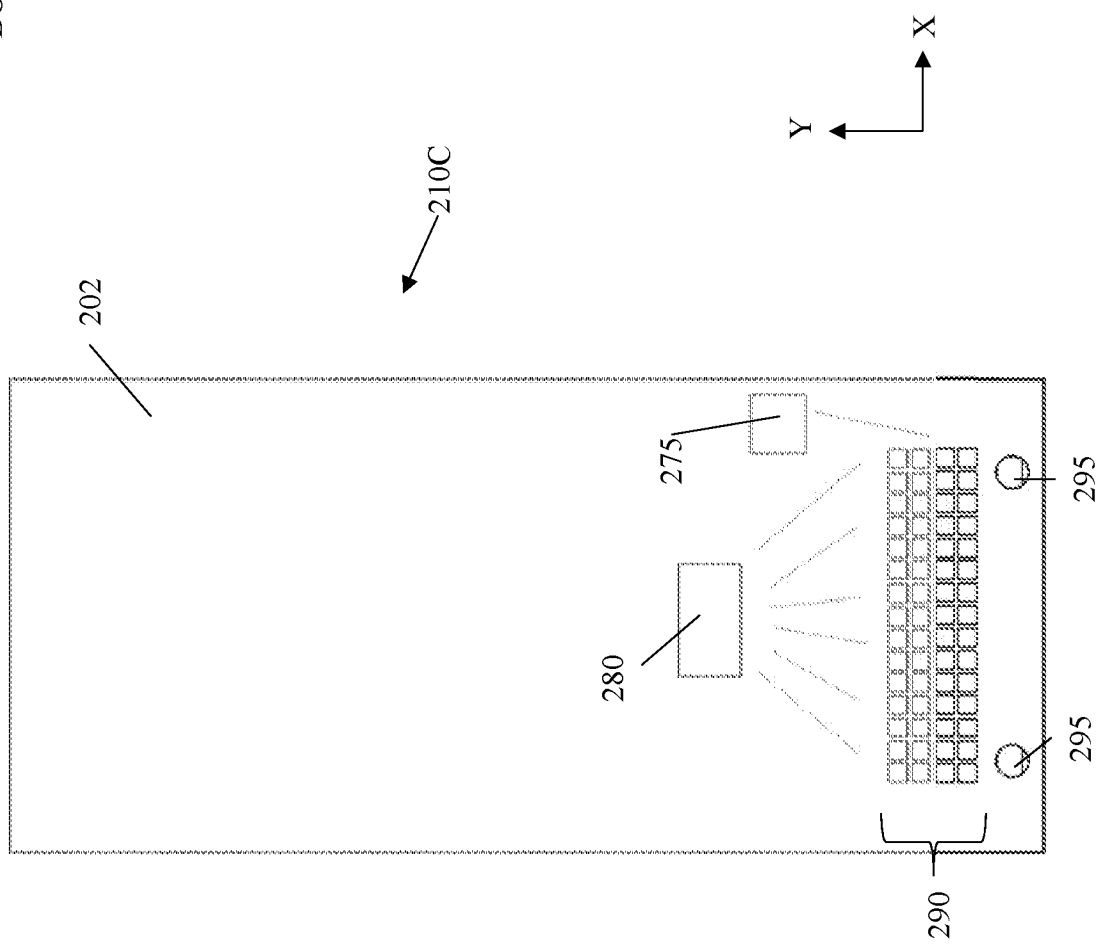
Figure 17A:
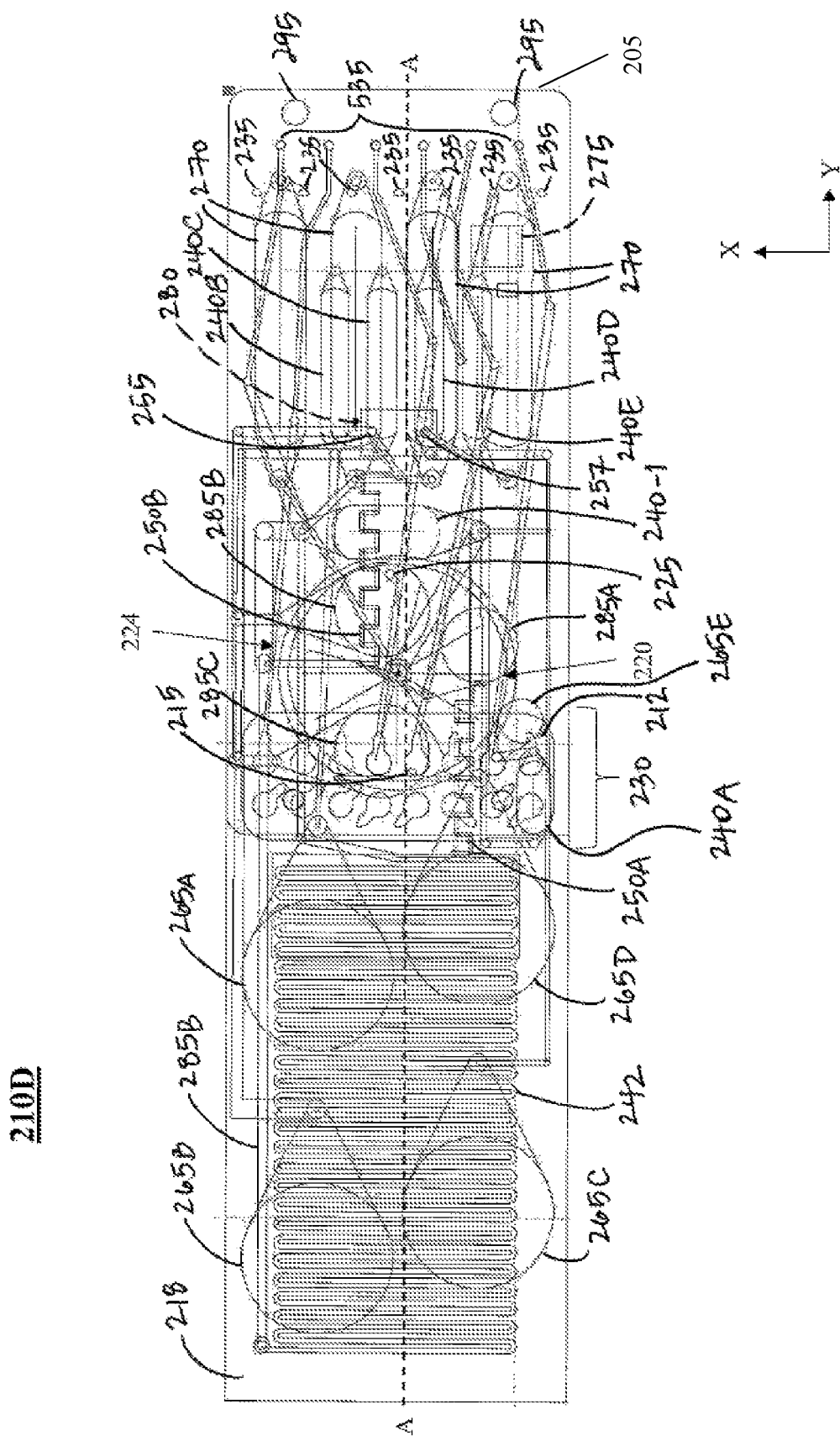
FIG. 17A shows a top view of a sample processing card configured for use in a cartridge assembly that uses a blood-based sample for a PCR test, in accordance with an embodiment herein.

FIGS. 15 and 16 illustrate a top 218 and a bottom (or a back), respectively, of another exemplary cartridge assembly 200 including an exemplary assay card 210C, in accordance with another embodiment herein. Although not expressly shown, it should be understood that the bottom (222) of card 210C may positioned against the top of the substrate 202, and optionally adhered to the substrate 202, as previously described. Substrate 202 may include a PCB, GMR sensor chip 280, electrical contact points 290, memory chip 275, optional heaters, and/or alignment devices 295, in accordance with an embodiment. Card 210C includes an injection port 215 and a vent port 225, which may be similar to and have similar functions as the ports described above with reference to FIGS. 5-13, for example. Filtration membrane 220 or filter, and reagent sections, and/or blister packs 265A and 265B may also be provided, which may be similar to those previously described. Filter 220 may be present if needed as for example in the case of filtering a sample of (whole) blood into plasma (the plasma being the part of the sample that is prepared). Valves in a valve array zone (not shown) may be provided in any number of areas in the card 210C of this cartridge assembly 200. Metering channels 240 are also provided in this assay cartridge, extending longitudinally between the filtration membrane 220 and output ports 255 to the GMR sensor chip 280 (provided on the substrate 202). Each of the chambers 240 (three are shown here) may be positioned at a depth within the housing (in the Z-direction), between the top and bottom surfaces of the card 210C, and in a manner such that they are parallel to one another in a lateral direction of the housing and extend a length in the longitudinal direction relative to the centerline A-A. Waste reservoirs 270 may also be provided in the card 210C. Pneumatic control ports 235 (shown in FIG. 15 as two parallel rows of ports (e.g., ports 235) near a front end 205 of the card 210C, connected to communication channels within the card) (which may be part of a pneumatic/pump interface) and alignment devices 295 (e.g., holes) may be provided on a top surface 218, as shown in FIG. 15, and electrical contact pads 290 and/or alignment devices 295 may be provided on a bottom surface (e.g., bottom of substrate 202) of the cartridge assembly 200, as shown in FIG. 16.

One or more cut-out sections may also be provided, e.g., on the bottom surface 222, in the card 210C to accommodate receipt of a portion of the GMR sensor chip 280 and/or on-board memory chip 275 of the substrate 202.

In use, functionalization for the specific application is printed (i.e. capture antibodies, DNA fragments, etc.) on GMR sensor chip 280 during assembly or manufacturing of the cartridge assembly 200. A sample (e.g., blood) is injected to port 215 while air is vented at opposite port 225. The cartridge assembly 200 is inserted into the biosensor base station such that alignment devices 295, pneumatic control ports 235, and electrical contact pads 290 connect to the cartridge reader unit 100. Parameters may be read by cartridge reader 310 from on-cartridge memory 275, to instruct the cartridge reader unit 100 how to reproduce the assay. For example, the cartridge reader 310 may perform and complete the following steps below, in sequence: A blood sample may be injected into the card via port 215 to separate blood into plasma. The filtered sample volume may then be metered via metering channels 240, if required by the assay. The filtered sample may then be mixed with detection reagent+blocker, if required by the assay. The mixture from previous step flows over sensor chip 280 and into waste reservoirs 270 (e.g., via input ports and channels). Next, Sandwich assay: antigens+biotinylated detection antibodies bind to printed capture antibodies I. Then, blister pack 265A may be punctured to release a quantity of wash buffer, e.g., 150 uL wash buffer. Wash buffer from 265A flows over sensor chip 280 and into waste reservoirs 270. Blister pack 265B may be punctured to release a quantity of beads solution, e.g., 150 uL Beads solution. Magnetic beads from 265B flows over sensor chip 280 and into waste reservoirs 270. GMR sensor signals from the sensor chip 280 are recorded while magnetic beads bind to sensor surface: e.g., Streptavadin on beads bind to biotin on detection antibodies. The captured antibody print map and standard curve data (both from memory 275) may be used along with recorded GMR sensor signals to calculate concentration of each antigen.

Figure 17B:
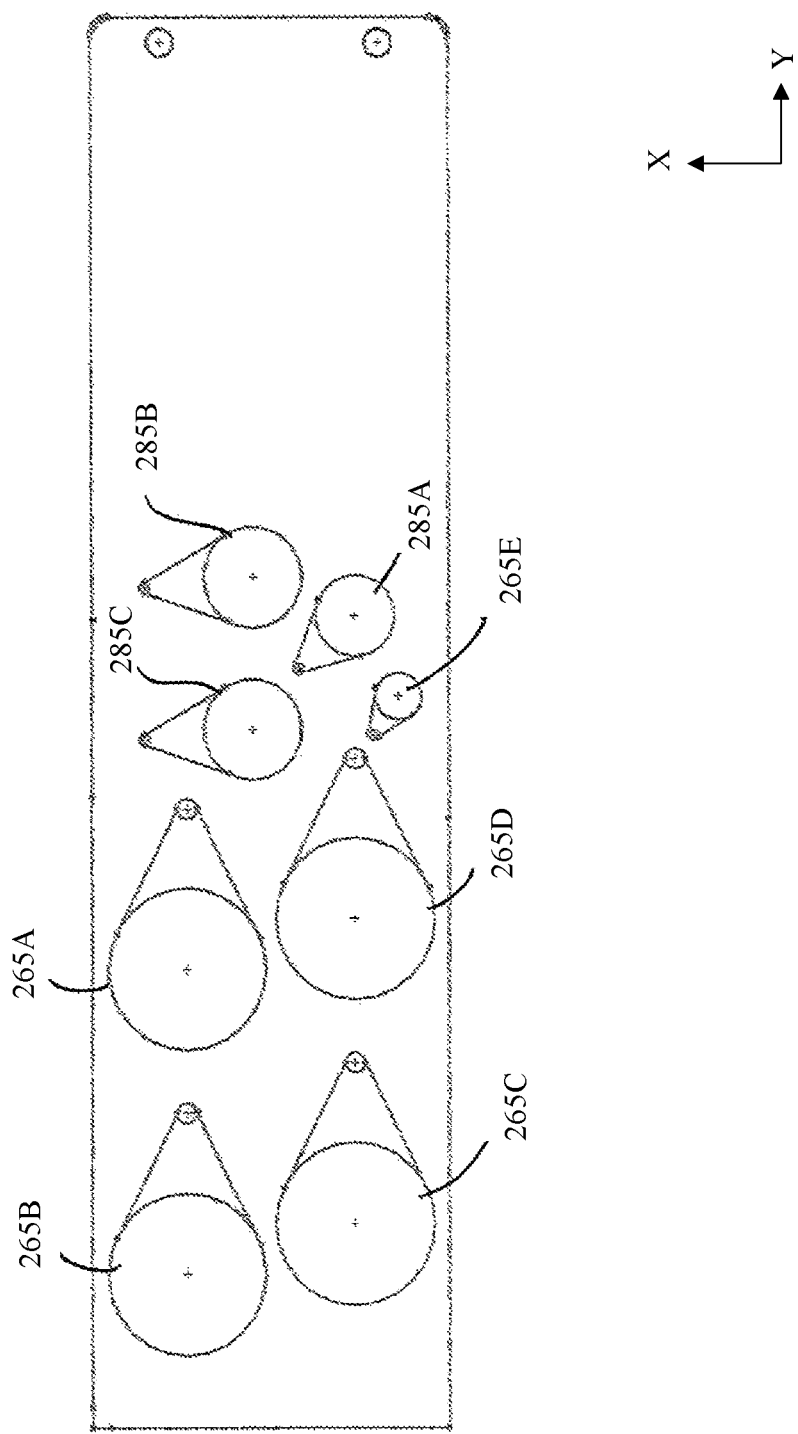
FIG. 17B shows a top view of an exemplary first layer of the sample processing card shown in FIG. 17A.
Figure 17C:
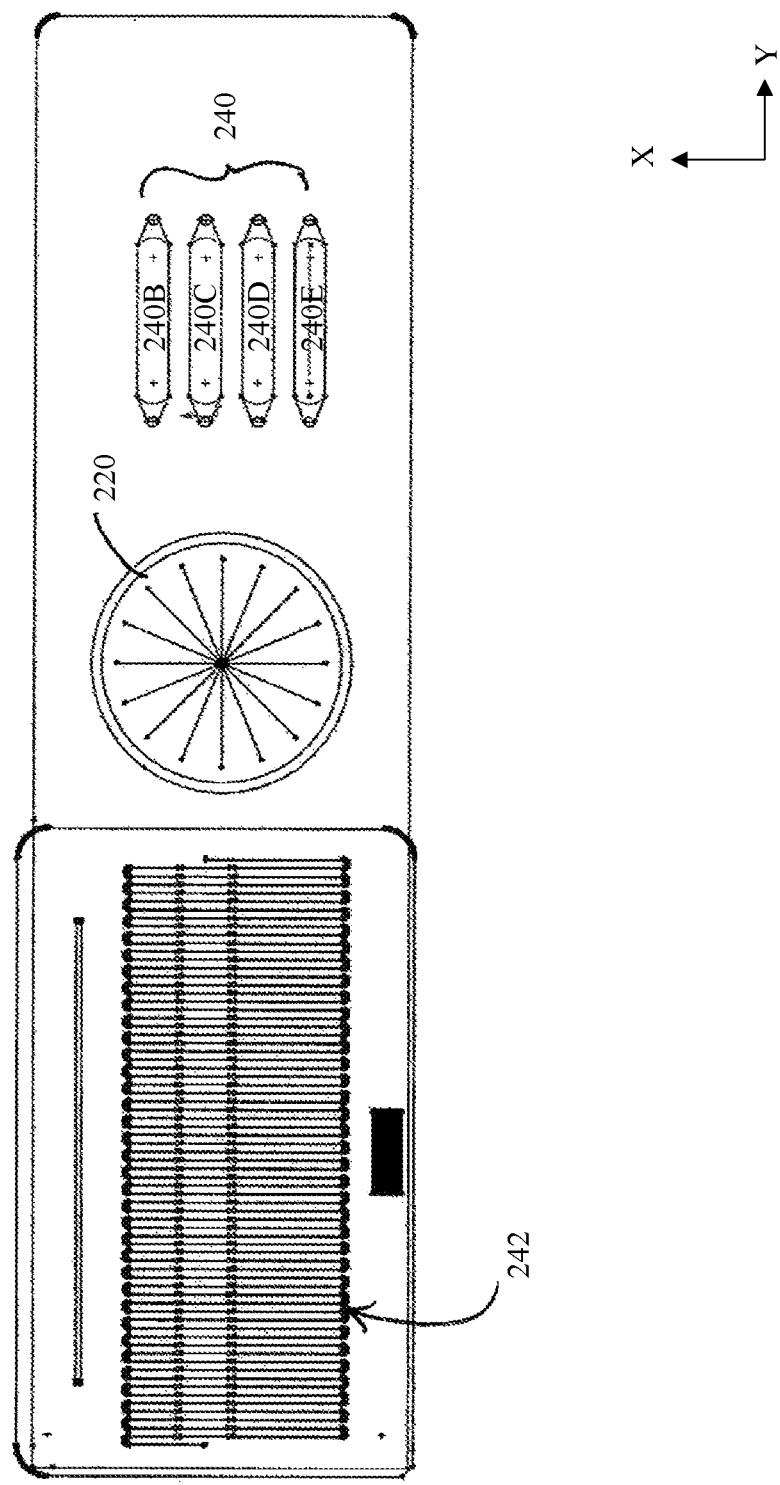
FIG. 17C shows a top view of an exemplary second layer of the sample processing card shown in FIG. 17A.
Figure 17D:
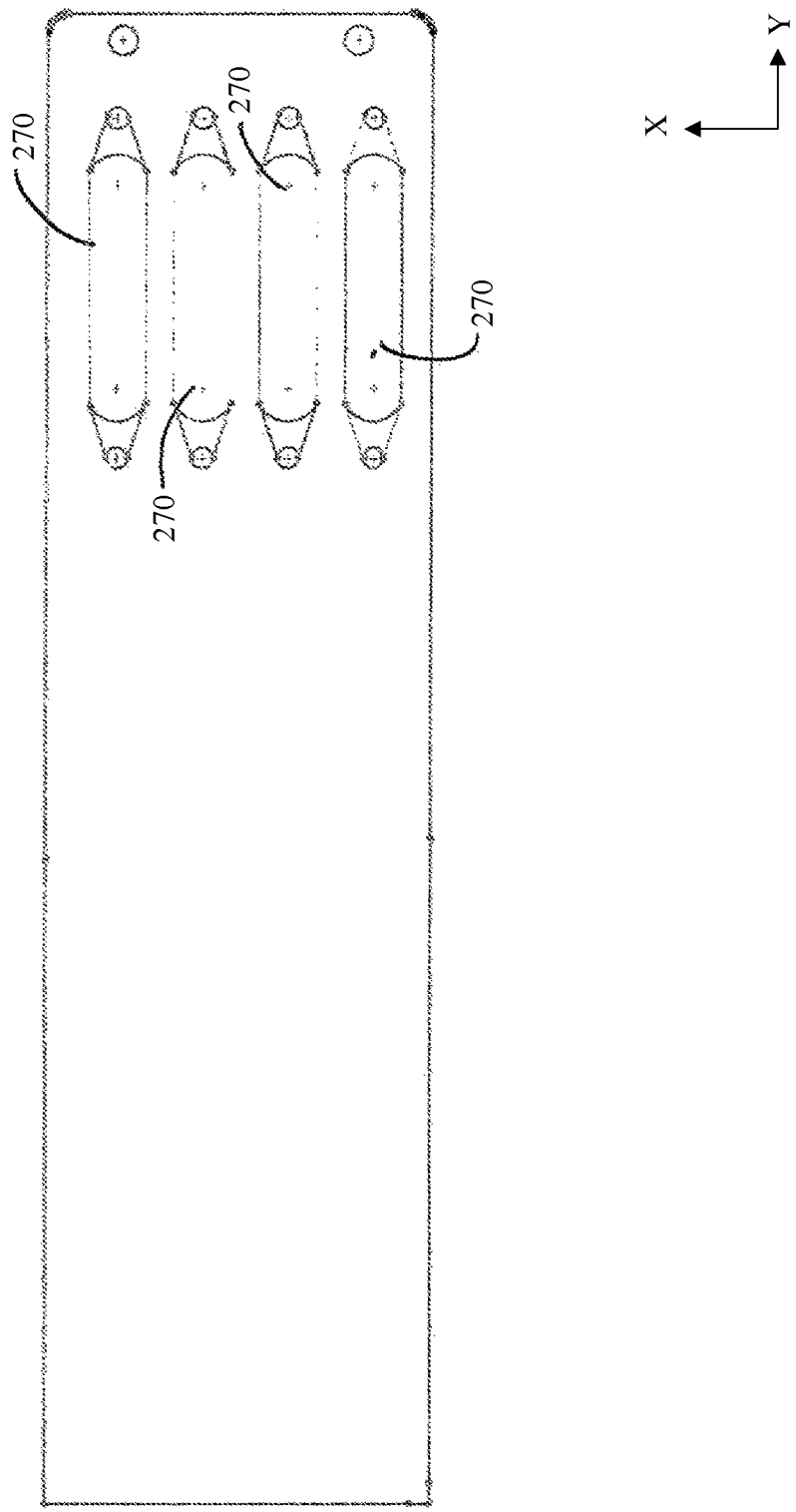
FIG. 17D shows a top view of an exemplary third layer of the sample processing card shown in FIG. 17A.

FIG. 17A shows a top view of a sample processing card 210D, configured for use as a sample processing card in a cartridge assembly 200 which configured for use in cartridge reader unit 100, in accordance with an embodiment herein. Although not expressly shown, it should be understood that the bottom (222) of card 210D may positioned against the top of the substrate 202, and optionally adhered to the substrate 202, as previously described. Substrate 202 may include a PCB, GMR sensor chip 280, electrical contact points 290, memory chip 275, optional heaters, and/or alignment devices 295, in accordance with an embodiment. One or more cut-out sections may be provided, e.g., on the bottom surface in the card 210D, to accommodate receipt of a portion of the GMR sensor chip 280 and/or on-board memory chip 275 of the substrate 202. Exemplary locations of the chip 280 and memory card 275 relative to the additional features in the card 210D are generally shown in FIG. 17A. In accordance with an embodiment, the card 210D is configured for use with a blood-based sample for a PCR test, e.g., ctDNA. As noted herethroughout in the described embodiments, the card 210D may be formed from layers and/or contain parts at different depths therein. Pneumatic control ports 235 (shown in FIG. 17A as two parallel rows of ports (e.g., ports 235) near a front end 205 of the card 210D, connected to communication channels within the card) (which may be part of a pneumatic/pump interface) and alignment devices 295 (e.g., holes) may be provided on a top surface 218. FIGS. 17B, 17C, and 17D show examples of some of the layers and thus locations of the different parts and features in a depth of the card 210D (or in a different layer) in greater detail. The features described below are provided in the card 210D and formed such that they can communicate and move fluid/blood/sample/air throughout the card at different depths or layers. Valves in a valve array zone 230 may be provided relatively below the filtration membrane 220 in the vertical (Z) direction, in accordance with one embodiment. In another embodiment, valve array zone 230 may be provided relatively above the filtration membrane 220. FIG. 17B shows a top view of an exemplary first layer (or top layer) of the card 210D showing blister packs 265A, 265B, 265C, 265D, and 265E and blister packs 285A, 285B, 285C (which, in one embodiment, may be chambers). Blister packs 285 A-C are connected via communication channels to output port(s) 255 to GMR sensor chip 280 (generally represented in FIG. 17A). FIG. 17C shows a top view of an exemplary second layer of the card 210 showing a serpentine channel 242, beads capture chamber 285B, a filtration membrane 220, and wash buffer metering chamber(s) 240B, 240C, 240D, and 240E at a depth therein. As shown in FIGS. 17A and 17C, each fluid metering chamber 240B-E may extend longitudinally between the filtration membrane 220 and pneumatic control ports 235. Each of the chambers 240A-E (four are shown here) may be positioned at a depth within the housing (in the Z-direction), between the top and bottom surfaces 218 and 222, and in a manner such that they are parallel to one another in a lateral direction of the housing and extend a length in the longitudinal direction relative to the centerline A-A. Communication channels (generally shown in FIG. 17A) connect each of the blister packs 265A-D to one of the metering chambers 240 B-E, respectively. FIG. 17D shows a top view of an exemplary third layer of the card 210D showing waste chamber 270. Also, communication channels are provided to connect metering chamber 240-1 (shown in FIG. 17A) to waste chamber 270. In accordance with an embodiment, waste chamber 270 may be a single, large chamber. That is, the (four) chambers 270 as shown in FIG. 17D may be separate sections of a single waste chamber 270, which are connected via channels therebetween. Generally, liquid waste from metering chamber 240-1 may be pulled to waste chamber 270. Two mixing channels 250A and 250B, each having a stepped configuration, are also provided. Of course this is an illustrative example in accordance with one embodiment. The depth and positioning of the channels and features and layers therein may be altered.

In use, a sample (e.g., patient whole blood (e.g., 1 mL)) is injected into the injection port 215 while the vent port 225 is open. The blood sample spreads laterally through and across the filtration membrane 220 and the plasma will be separated from the whole blood sample by applying negative pressure using pneumatic system 330 through pneumatic control ports 235. As shown in FIG. 17A, a number of pneumatic control ports 235 may be provided on the card 210D, e.g., near a bottom portion of the top surface 218 thereof. In addition, in an embodiment, a number of separate valve control ports 535 may be provided as part of card 210D. As shown in FIG. 17A, for example, the valve control ports 535 may be provided adjacent to the pneumatic control ports 235, e.g., at a front end of the card 210D. Magnetic beads and lysis buffer in blister pack 265A is open and pulled to the magnetic beads and lysis buffer metering chamber 240B by applying negative pressure to a corresponding pump port 235 (through a (connected and) corresponding communication channel). Magnetic beads/lysis buffer in the metering chamber 240B is pushed to chamber 240-1 (through a connecting channel) then to a connected waste chamber 270. The surface of the magnetic beads is modified to capture nucleic acids. The size of the magnetic beads is not limited; it can be in a range from 200 nm to 1 um. 500 uL of the separated plasma is mixed with magnetic beads and lysis buffer in chamber 240-1. The beads/lysis buffer and plasma can be mixed by using magnetic fields, e.g., by controlling a second magnetic field generator in the unit 100. The magnetic fields may be on both sides, top or bottom of the chamber. The chamber is also heated at 56 C. The mixture is mixed and heated for 15 mins (e.g., via a heating element provided on a top side of a PCB/substrate 202, as previously noted). After 15 mins, the magnetic beads are immobilized on the chamber surface by applying magnetic field. The liquid is removed to a connected waste chamber(s) 270 by applying negative pressure through corresponding port(s) 235. Wash buffer1 in blister pack 265B is open and pulled to the wash buffer1 metering chamber 240C by applying negative pressure to a corresponding pump port 235 (through a (connected and) corresponding communication channel). Wash buffer1 in the metering chamber 240C is pushed to chamber 240-1 (through a connecting channel)

by applying negative pressure through port 235 (through a (connected and) corresponding communication channel) while beads are immobilized on the chamber surface by applying electrical magnetic fields. Magnetic beads are then mixed with wash buffer in chamber 240-1 by changing the direction of electrical magnetic fields for 2 minutes. The magnetic beads are immobilized on the chamber surface by applying magnetic field. The liquid is removed to waste chamber(s) 270 by applying negative pressure through port(s) 235 (through a (connected and) corresponding communication channel). Wash buffer2 in blister pack 265C is open and pulled to the wash buffer1 metering chamber 240D by applying negative pressure to a corresponding pump port 235 (through a (connected and) corresponding communication channel). Wash buffer1 in the metering chamber 240D is pushed to chamber 240-1 (through a connecting channel) by applying negative pressure through port(s) 235 (through a (connected and) corresponding communication channel) while beads are immobilized on the chamber surface by applying electrical magnetic fields. Magnetic beads are then mixed with wash buffer in chamber 240-1 by changing the direction of electrical magnetic fields for 2 minutes. The magnetic beads are immobilized on the chamber surface by applying magnetic field. The liquid is removed to waste chamber(s) 270 by applying negative pressure through port(s) 235 (through a (connected and) corresponding communication channel). Wash buffer3 in blister pack 265D is open and pulled to the wash buffer1 metering chamber 240E by applying negative pressure to a corresponding pump port 235 (through a (connected and) corresponding communication channel). Wash buffer1 in the metering chamber 240E is pushed to chamber 240-1 (through a connecting channel) by applying negative pressure through port(s) 235 while beads are immobilized on the chamber surface by applying electrical magnetic fields. Magnetic beads are then mixed with wash buffer in chamber 240-1 by changing the direction of electrical magnetic fields for 2 minutes. The magnetic beads are immobilized on the chamber surface by applying magnetic field. The liquid is removed to waste chamber(s) 270 by applying negative pressure through port(s) 235 (through a (connected and) corresponding communication channel). PCR reagents in blister pack 265E is pulled to the PCR reagent metering chamber 240A by applying negative pressure to a connected pump port(s) 235 (through a (connected and) corresponding communication channel). PCR reagent in the metering chamber 240A and the magnetic beads capturing nucleic acids in the chamber 240-1 are pushed to a mixing channel 250A by applying positive pressure to corresponding pump port(s) 235 (through a (connected and) corresponding communication channel). PCR mix is then pushed to the serpentine channel 242 for thermocycling amplification process by applying positive pressure to corresponding pump port 235 (through a (connected and) corresponding communication channel). The serpentine channel 242 may be heated through two or three heaters (e.g., via a heating element provided on a top side of a PCB/substrate 202, as previously noted) at different temperatures for amplification purposes. The serpentine channel 242 may be longer or shorter depends on the specific amplification protocol. The PCR product with magnetic beads are going through the blister pack 285B where magnetic beads are captured by applying electrical magnetic field. DNA single strand enzyme in blister pack 285A is open, and the PCR product solution in beads capture chamber/blister pack 285B and the DNA single strand enzyme in blister pack 285A are pushed to the mixing channel 250B then (through a connecting channel) to the GMR sensor chip 280 (e.g., via an output, like output 255, not shown) and finally to a connected waste chamber 270. Wash buffer4 in blister pack 285B is open and pushed (through output port(s) 255) to the GMR sensor chip 280 (through a connecting channel) on the substrate 202 (not shown) then (back through input port(s) 257) to the connected waste chamber 270. Buffer contains magnetic beads in blister pack 285C is open and pushed, by applying positive pressure to a pump port 235, to the GMR sensor chip 280 (through a connecting channel), and then to a connected waste chamber 270. Valve array zone 230 contains elastomeric material 212 and valves are open or closed by applying pressure through ports 535 (and (through connected corresponding communication channels). The transition sections 351 are formed to reduce bubbles forming in the chambers.

The card 210D may include any type or number of wash buffers therein. For example, in accordance with an embodiment, wash buffer1 may be diluted lysis buffer, wash buffer2 may be a PCR inhibitor removal buffer, wash buffer3 may be an ion removal buffer, and wash buffer4 may be a 50 mM salt buffer, such as Na3PO4. Accordingly, the type and number of wash buffers used therein is not intended to be limiting.

Figure 18B:
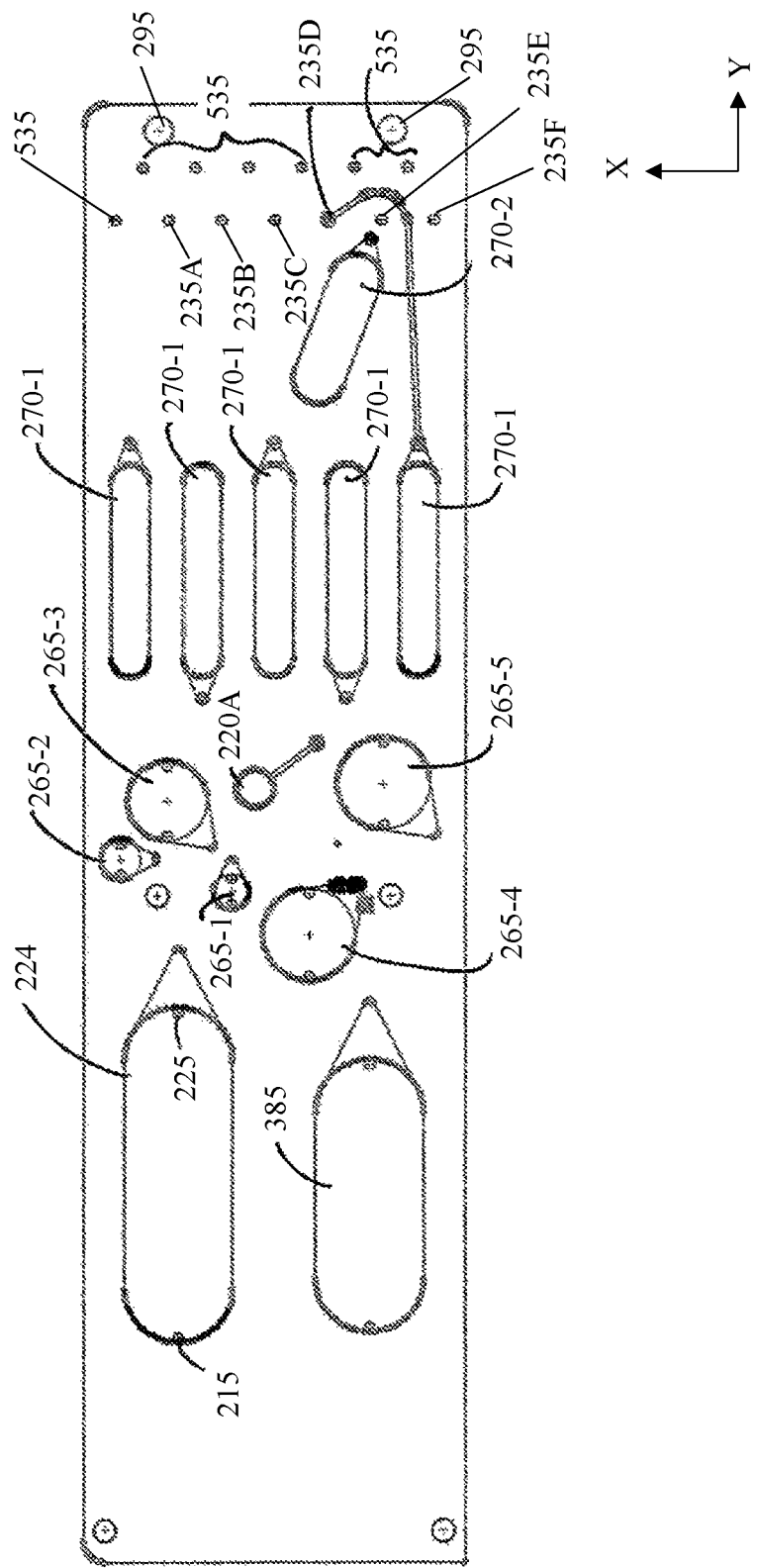
FIG. 18B shows a top view of an exemplary top layer of the sample processing card shown in FIG. 18A.
Figure 18C:
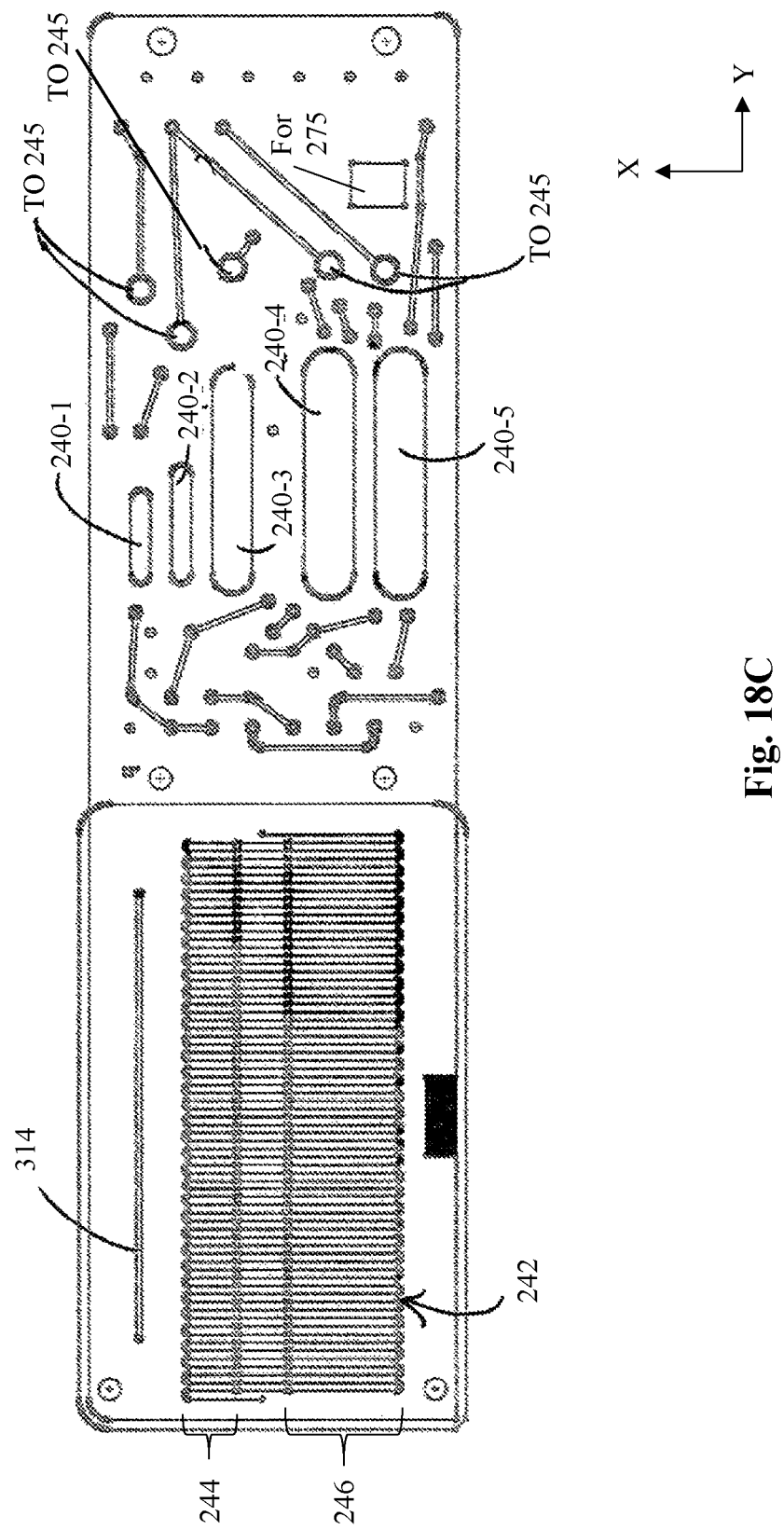
FIG. 18C shows a top view of an exemplary second layer of the sample processing card shown in FIG. 18A.
Figure 18D:
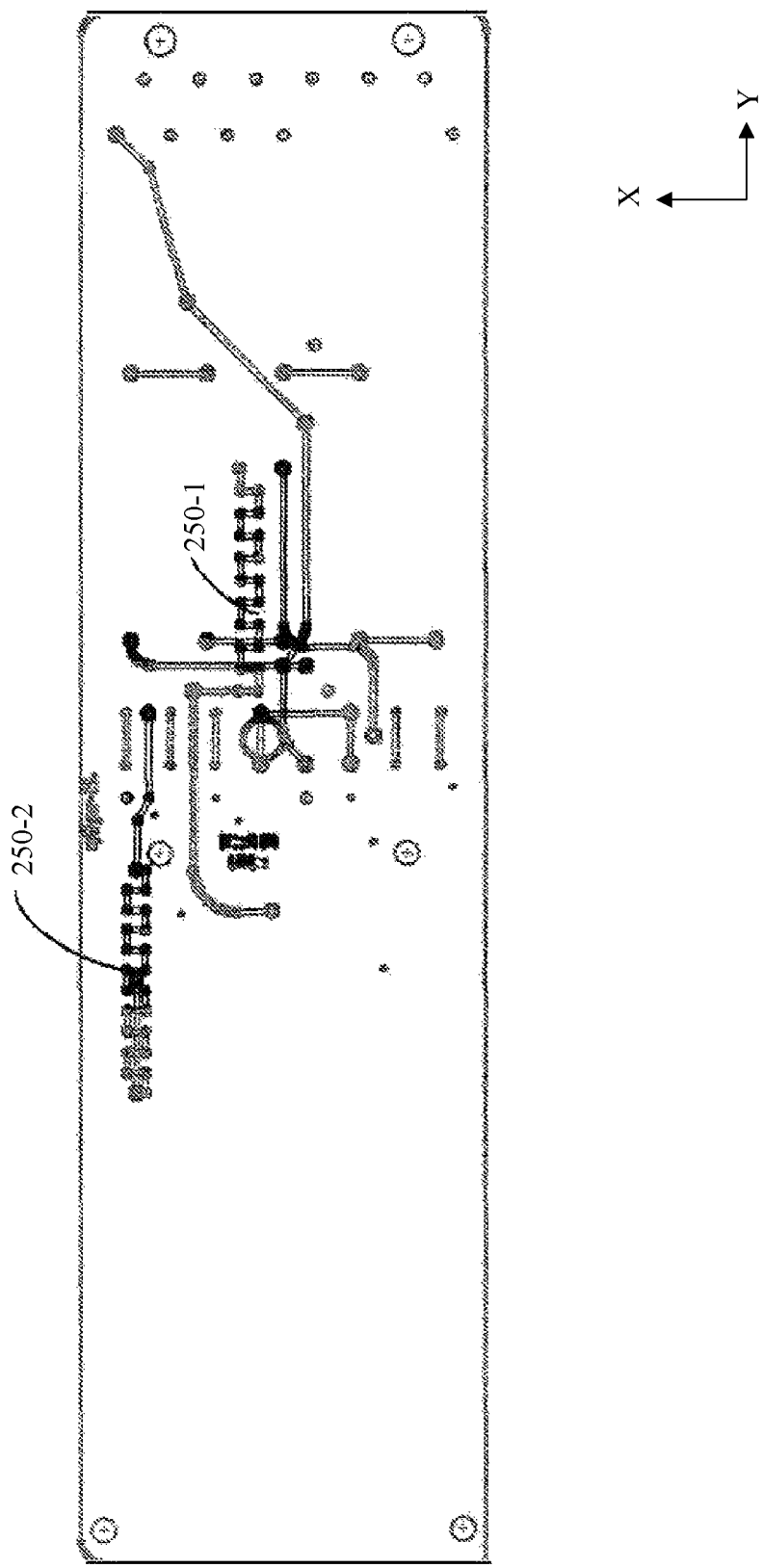
FIG. 18D shows a top view of an exemplary third layer of the sample processing card shown in FIG. 18A.
Figure 18E:
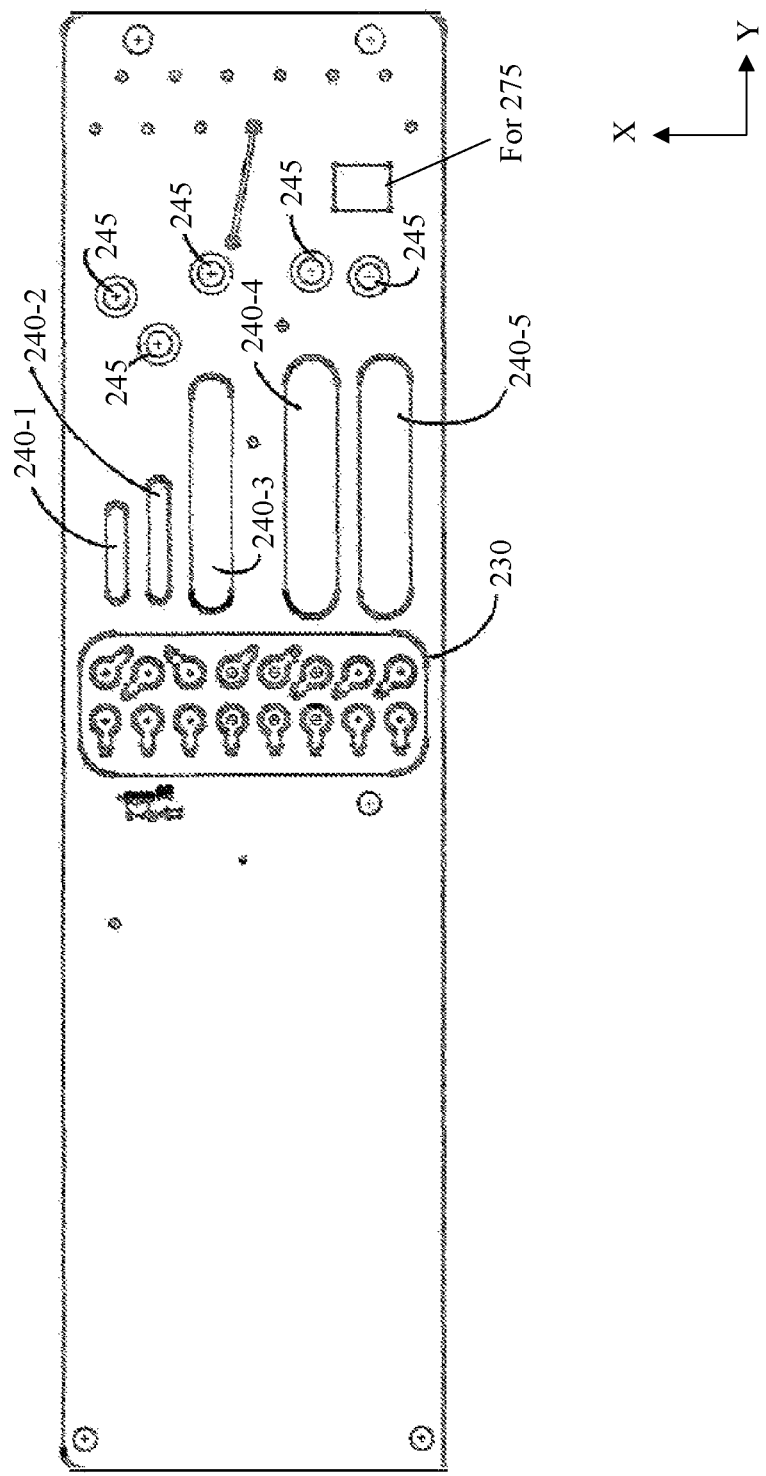
FIG. 18E shows a top view of an exemplary bottom layer of the sample processing card shown in FIG. 18A.

FIG. 18A shows a top view of a microfluidic chamber card 210E, configured for use as a sample processing card in a cartridge assembly 200 which is configured for use in cartridge reader unit 100, in accordance with an embodiment herein. Although not expressly shown, it should be understood that the bottom (222) of card 210E may positioned against the top of the substrate 202, and optionally adhered to the substrate 202, as previously described. Substrate 202 may include a PCB, GMR sensor chip 280, electrical contact points 290, memory chip 275, optional heaters, and/or alignment devices 295, in accordance with an embodiment. One or more cut-out sections may be provided, e.g., on and/or through the bottom surface in the card 210E (e.g., cut-out sections may be provided through one or more layers), to accommodate receipt of a portion of the GMR sensor chip 280 and/or on-board memory chip 275 of the substrate 202. Exemplary locations of the chip 280 and memory card 275 relative to the additional features in the card 210E are generally shown in FIG. 18A. In accordance with an embodiment, the card 210E is configured to receive a high-salt solution with a (cheek) swab sample (PCR). As noted herethroughout in the described embodiments, the card 210E may be formed from layers and/or contain parts at different depths therein. As shown in FIG. 18A, a number of pneumatic control ports 235A-235F may be provided on the card 210E, e.g., near a front end on the top surface 218 thereof. In addition, in an embodiment, a number of separate valve control ports 535 may be provided as part of card 210E. FIGS. 18B-18E show examples of some of the layers and thus locations of the different parts and features in a depth of the card 210E (or in a different layer) in greater detail. The features described below are provided in the card 210E and formed such that they can communicate and move fluid/blood/sample/air throughout the card at different depths or layers. FIG. 18B shows a top view of an exemplary top layer of the card 210E showing sample chamber 224, injection port 215, vent port 225, glass fiber membrane 220A, blister packs/chambers 265-1, 265-2, 265-3, 265-4, and 265-5 and waste chambers/tanks 270-1 and 270-2 provided at a depth therein. Pneumatic control ports 235 (shown in FIGS. 18A and 18B as two parallel rows of ports (e.g., ports 235) near a front end 205 of the card 210E, connected to communication channels within the card) (which may be part of a pneumatic/pump interface) and alignment devices 295 (e.g., holes) may be provided on a top surface 218 and/or layers therebelow. FIG. 18C shows a top view of an exemplary second layer of the card 210E showing PCR heating and cooling (e.g., via a heating element provided on a top side of a PCB/substrate 202, as previously noted) serpentine feature or serpentine channel 242, along with additional fluid/air channels and parts of chambers 240-1 to 240-5 at a depth therein. As shown in FIGS. 18A and 18C, each fluid metering chamber 240-1 to 240-5 may extend longitudinally between the valve array 230 and pneumatic control ports 235. Each of the chambers 240 (five are shown here) may be positioned at a depth within the housing (in the Z-direction), between the top and bottom surfaces of the card 210E, and in a manner such that they are parallel to one another in a lateral direction of the housing and extend a length in the longitudinal direction relative to the centerline A-A. FIG. 18D shows a top view of an exemplary third layer of the card 210E showing PCR mixing channels 250-1 and 250-2 (each having a stepped configuration) and additional communication channels for connecting therewith and connecting other features in the card 210E. FIG. 18E shows a top view of an exemplary bottom layer of the cartridge valve array zone 230, at least part of metering chambers 240-1 to 240-5, gas permeable membrane 245 (GPMs 245), an opening or interface for memory chip 275 or card (provided on the substrate 202), and parts of ports 235 at a depth therein. Valves in a valve array zone 230 may be provided relatively between metering chambers 240-1 to 240-5 and serpentine channel 242 in the longitudinal (Y) direction of the card, in accordance with one embodiment. Of course this is an illustrative example in accordance with one embodiment. The depth and positioning of the channels and features and layers therein may be altered.

In use, a swab sample immersed in high salt solution for 5 minutes, then the solution that contains nucleic acids and proteins from patient swab is injected to the sample chamber 224 through the injection port 215 with the vent port 225 positioned relatively opposite to the injection port 215. The high salt solution is then pulled through the glass fiber membrane 220A then to a corresponding waste chamber 270-1 by applying negative pressure to pump port 235D. Insoluble nucleic acids in high salt solution bind to a glass fiber membrane 220A. Glass fiber membrane 220A is washed by ethanol from chamber 385. Ethanol in chamber 385 is pulled through to the glass fiber membrane 220A then to a corresponding waste chamber 270-1 by applying negative pressure to pump port 235D. Glass fiber membrane 220A is dried by pulling air through for 2 to 5 minutes. Port 306 may be a vent port that is open to the atmosphere such that air may be pulled through the glass fiber membrane 220A by applying negative pressure (vacuum) to a control pump port 535A of the valve actuation interface through a (connected and) corresponding communication channel(s) 554. Low ionic solution in chamber 265-1 (such as water or Tris-EDTA buffer) is pulled through the glass fiber membrane 220A until the solution(s) reach the gas permeable membrane 245 by applying negative pressure to a control port 535A of the valve actuation interface through a (connected and) corresponding communication channel(s) 554 using a connected pump/pneumatic system 330. PCR reagents in chamber 265-2 are pulled to the PCR reagent metering chamber 240-2 until the solution(s) reach the gas permeable membrane 245 by applying negative pressure to a pump port 235B through a (connected and) corresponding communication channel 554. PCR reagent in the metering chamber 240-2 and eluent in the eluent chamber 240-1 are pushed to the PCR mix incubation channel 314 (which acts as a mixing chamber, since fluid/liquid may be stopped, for incubation purposes, during the processing of the sample) via a mixing channel 250-2 by applying positive pressure to pump ports 235A and 235B through a (connected and) corresponding communication channel(s) 554. Port 235F is vented during this process. PCR mix in incubation channel 314 is heated for RNAs to transcribe to DNAs for 10 minutes. Port 235F is closed during this process. PCR mix in incubation channel 314 is then pushed to the serpentine channel 242 for thermocycling amplification process by applying positive pressure to pump port 235B through a (connected and) corresponding communication channel 554. The serpentine channel 242 can be heated through two or three heaters (e.g., provided on an attached substrate 202) at different temperatures for amplification purposes. For example, in an embodiment, a first temperature zone 244 may be provided near or along a first portion or segment (e.g., see FIG. 18C) of the serpentine channel 242, while a second, different temperature zone 246 may be provided near or along a second portion (see FIG. 18C) of the serpentine channel 242. The temperature zones 244 and 246 may be separated by a distance which allows fluid to ramp (heating/cooling). In the exemplary illustration of FIG. 18C, the first temperature zone 244 is approximately half the distance of the second temperature zone 246, but this is illustrative only and not intended to be limiting. The time for applying each temperature zone may depend on flow rate and channel dimension, for example. A total time for applying heating may be dependent upon the number of turns or cycles tied to the serpentine channel 242. The serpentine channel 242 can be longer or shorter depending on the specific amplification protocol. DNA single-strand enzyme in chamber 285-1 is pulled to the DNA single-strand enzyme metering chamber 240-3 until the solution(s) reach the gas permeable membrane 245 by applying negative pressure to a pump port 235C through a (connected and) corresponding communication channel 554. The PCR product solution in amplification serpentine channel 242 and the DNA single-strand enzyme in metering chamber 240-3 are pushed to the mixing channel 250-2 then (through output ports 255) to the GMR sensor chip 280 (provided on the substrate 202 (not shown)) and finally (back through input ports 257) reach the corresponding waste chamber 270-2 of the card 210E. Wash buffer in chamber 265-4 is pulled to the wash buffer metering chamber 240-4 until the solution(s) reach the gas permeable membrane 245 by applying negative pressure to a pump port 235A through a (connected and) corresponding communication channel 554. In accordance with an embodiment, the wash buffer may be a 50 mM salt buffer, such as Na3PO4. Wash buffer in the wash buffer metering chamber 240-4 is pushed to the GMR sensor chip 280 then to a corresponding waste chamber 270-1. The buffer containing magnetic beads in chamber 265-5 is pulled to the wash buffer metering chamber 240-5 until the solution(s) reach the gas permeable membrane 245 by applying negative pressure to a pump port 235B through a (connected and) corresponding communication channel 554. The buffer containing magnetic beads in the metering chamber 240-5 is pushed by applying positive pressure to a pump port 235B to the GMR sensor chip 280 then to corresponding waste chamber 270-2. Valve array zone 230 contains elastomeric material 212. The transition sections 351 are formed to reduce bubbles forming in the chambers.

FIGS. 19 and 20 illustrate a top and a bottom, respectively, of another exemplary cartridge assembly 200 including an exemplary assay sample processing card 210F configured for use as a sample processing card in a cartridge assembly 200 which is configured for use in cartridge reader unit 100, in accordance with an embodiment herein. Although not expressly shown, it should be understood that the bottom (222) of card 210F may positioned against the top of the substrate 202, and optionally adhered to the substrate 202, as previously described. One or more cut-out sections may be provided, e.g., on and/or through the bottom surface in the card 210F to accommodate receipt of a portion of the GMR sensor chips 280A-280D and/or on-board memory chip 275 of the substrate 202. The card 210F may be configured to determine relative kinetics for antibodies, in accordance with yet another embodiment herein. In an embodiment, this card 210F may also be configured for use with a high-salt solution with a (cheek) swab sample. The solutions to be tested are loaded into chambers A2-A12, which are configured to hold a volume of fluid or liquid therein, e.g., one solution per chamber. Chamber A1 is normally used for a positive or negative control. Ligand-coated magnetic beads are loaded into/provided in sample chamber 285. Blister pack(s) 265 are provided in the card 210F to hold wash and block buffers. Valves in a valve array zone (not shown) may be provided in any number of areas in the card 210F of this cartridge assembly 200. Pneumatic control ports 235 (shown in FIG. 19 as two parallel rows of ports (e.g., ports 235) near a front end 205 of the card 210F, connected to communication channels within the card) (which may be part of a pneumatic/pump interface) and alignment devices 295 (e.g., holes) may be provided on a top surface 218, and electrical contact pads 290 and/or alignment devices 295 may be provided on a bottom surface (e.g., underside of the substrate 202), as shown in FIG. 20. Samples in chambers A1-A12 are pulled through (connected and) corresponding channels to one or more GMR sensor chips 280A, 280B, 280C, and/or 280D and to the waste reservoir 270. Blister pack 265 is punctured and releases wash+block buffer through each channel to chips 280A-280D and then to waste reservoir 270. Magnetic beads from sample chamber 285C flow through channels to chips 280 to the waste reservoir 270. Electrical resistance change on each sensor 280A-280D is configured to be measured in real-time to indicate binding speeds of proteins+ligand. Sensors 280A-280D are connected through electrical contact pads 290. Simultaneously, record GMR signals (e.g., on memory card 275 or a cloud server) from GMR sensor chips 280A-280D and display results in real time (e.g., via display 120 on cartridge reader unit 100).

Figure 21:
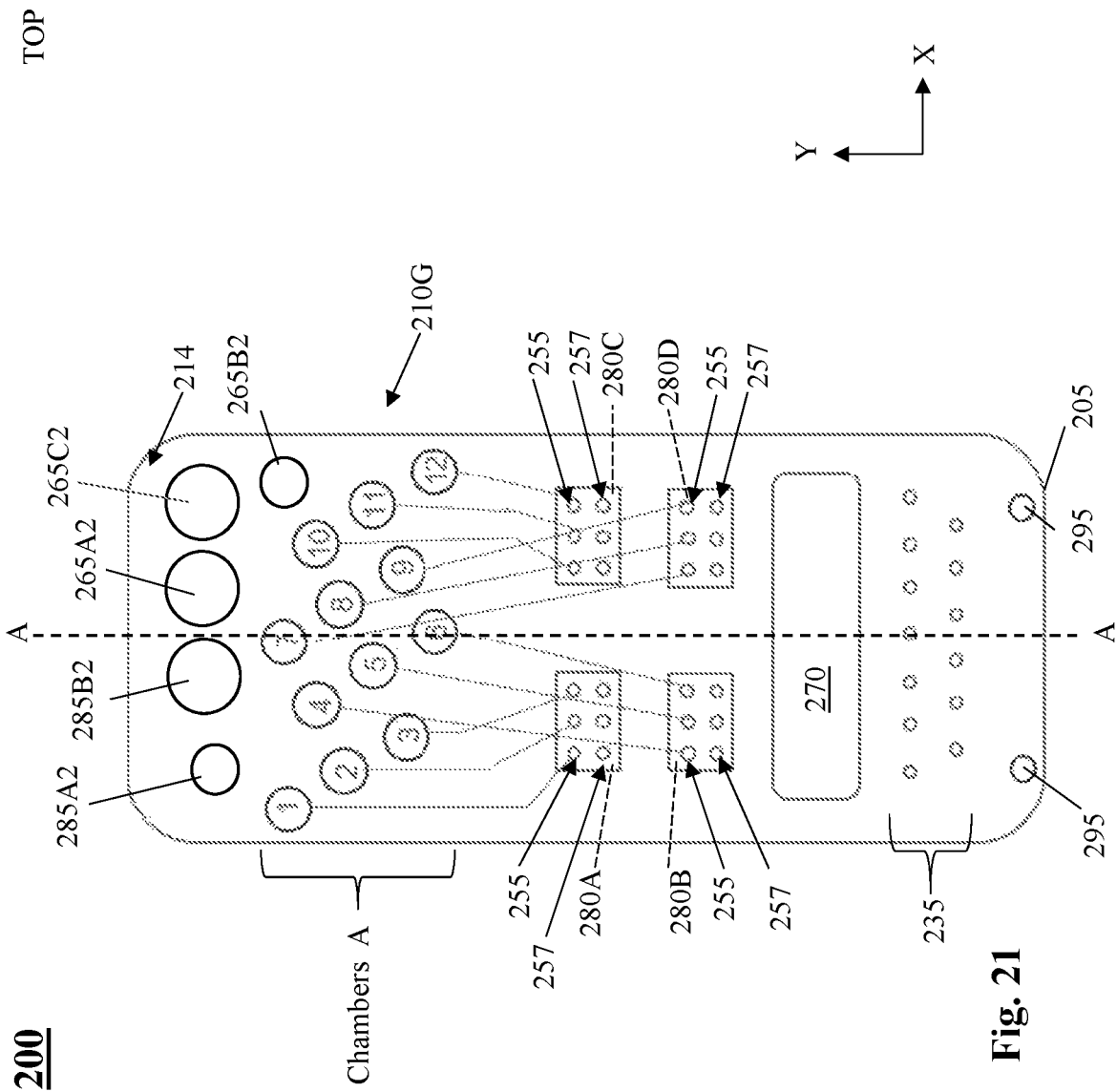
FIGS. 21 and 22 illustrate a top and a bottom, respectively, of an exemplary assay sample processing card configured for use in a cartridge assembly, that determines dissociation constants for antibodies, in accordance with still yet another embodiment herein.
Figure 22:
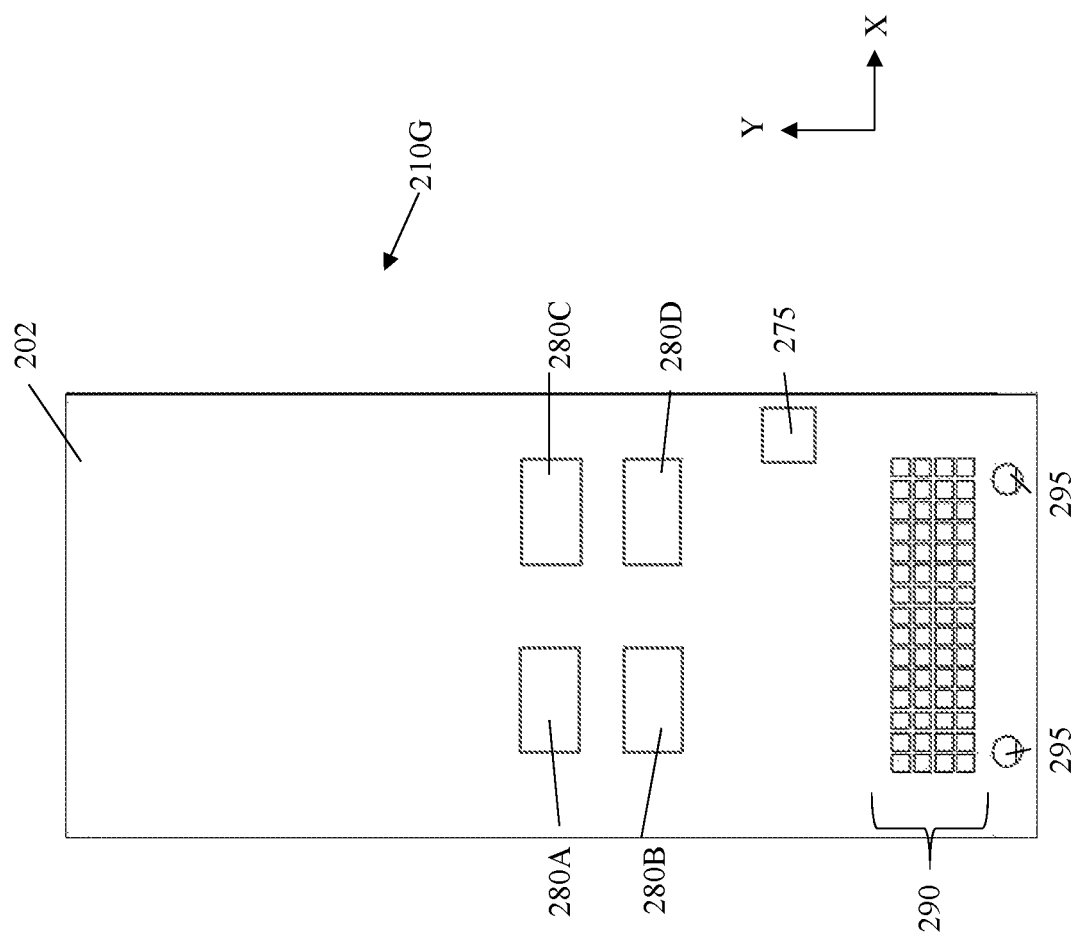

FIGS. 21 and 22 illustrate a top and a bottom, respectively, of an exemplary cartridge assembly 200 including an exemplary assay sample processing card 210G configured for use as a sample processing card in a cartridge assembly 200 which is configured for use in cartridge reader unit 100, in accordance with an embodiment herein. Although not expressly shown, it should be understood that the bottom (222) of card 210G may positioned against the top of the substrate 202, and optionally adhered to the substrate 202, as previously described. One or more cut-out sections may be provided, e.g., on and/or through the bottom surface in the card 210G to accommodate receipt of a portion of the GMR sensor chips 280A-280D and/or on-board memory chip 275 of the substrate 202. The card 210G may be configured to determine dissociation constants for antibodies, in accordance with still yet another embodiment herein. For the sake of brevity, previously described features—such as chambers, outlet ports 255 to the GMR sensor chips 280, waste chamber 270, etc.—are labeled in FIGS. 21-22 with same or similar reference numbers, and thus not necessarily repeated here. Pneumatic control ports 235 (shown in FIG. 21 as two parallel rows of ports (e.g., ports 235) near a front end 205 of the card 210G, connected to communication channels within the card) (which may be part of a pneumatic/pump interface) and alignment devices 295 (e.g., holes) may be provided on a top surface 218, and electrical contact pads 290 and/or alignment devices 295 may be provided on a bottom surface (e.g., underside of the substrate 202), as shown in FIG. 22. In use, the solution to be tested is loaded into chamber 285A2. For example, a positive control solution may be prepared (e.g., by dissolving powder in an immobilization buffer) and loaded into the chamber 285A2. Protein coating solution is loaded into chamber 285B2. Ligand solutions are loaded into chambers A1-A12, one solution per chamber. Such solutions may be either pre-loaded on the card 210 or loaded during the process. Blister pack 265A2 is provided in the card 210G to hold wash and block buffers. Blister pack 265B2 is provided in the card 210G to also hold wash and block buffers. Blister pack 265C2 is provided in the card 210G to hold magnetic beads (e.g., streptavidin-coated magnetic beads). Valves in a valve array zone (not shown) may be provided in any number of areas in the card 210G of this cartridge assembly 200. In use, the sample in chamber 285A is pulled through channel 1 to GMR sensor chip 280A and then to waste reservoir 270. Simultaneously, the sample in chamber 285B2 is pulled through channels 2-12 to GMR sensor chips 280B, 280C, and 280D and then to waste reservoir 270. Blister pack 265A2 is punctured, with its wash+block buffer pulled through each channel 1-12 to chips 280A-280D, and then to waste reservoir 270. Samples in chambers A1-A12 are pulled through channels 1-12 to GMR sensor chips 280A-280D, and then to waste reservoir 270. Blister pack 265B2 is punctured, with its wash buffer pulled through each channel in chips 280A-280D to waste reservoir 270. Magnetic beads from blister pack 265C2 flow through channels to chips 280A-280D and then to waste reservoir 270. Electrical resistance change on each sensor 280A-280D is configured to be measured in real-time to indicate binding speeds of proteins+ligand. Sensors 280A-280D are connected through electrical contact pads 290. Simultaneously, record GMR signals (e.g., on memory card 275 or a cloud server) from GMR sensor chips 280A-280D and display results in real time (e.g., via display 120 on cartridge reader unit 100).

Figure 23:
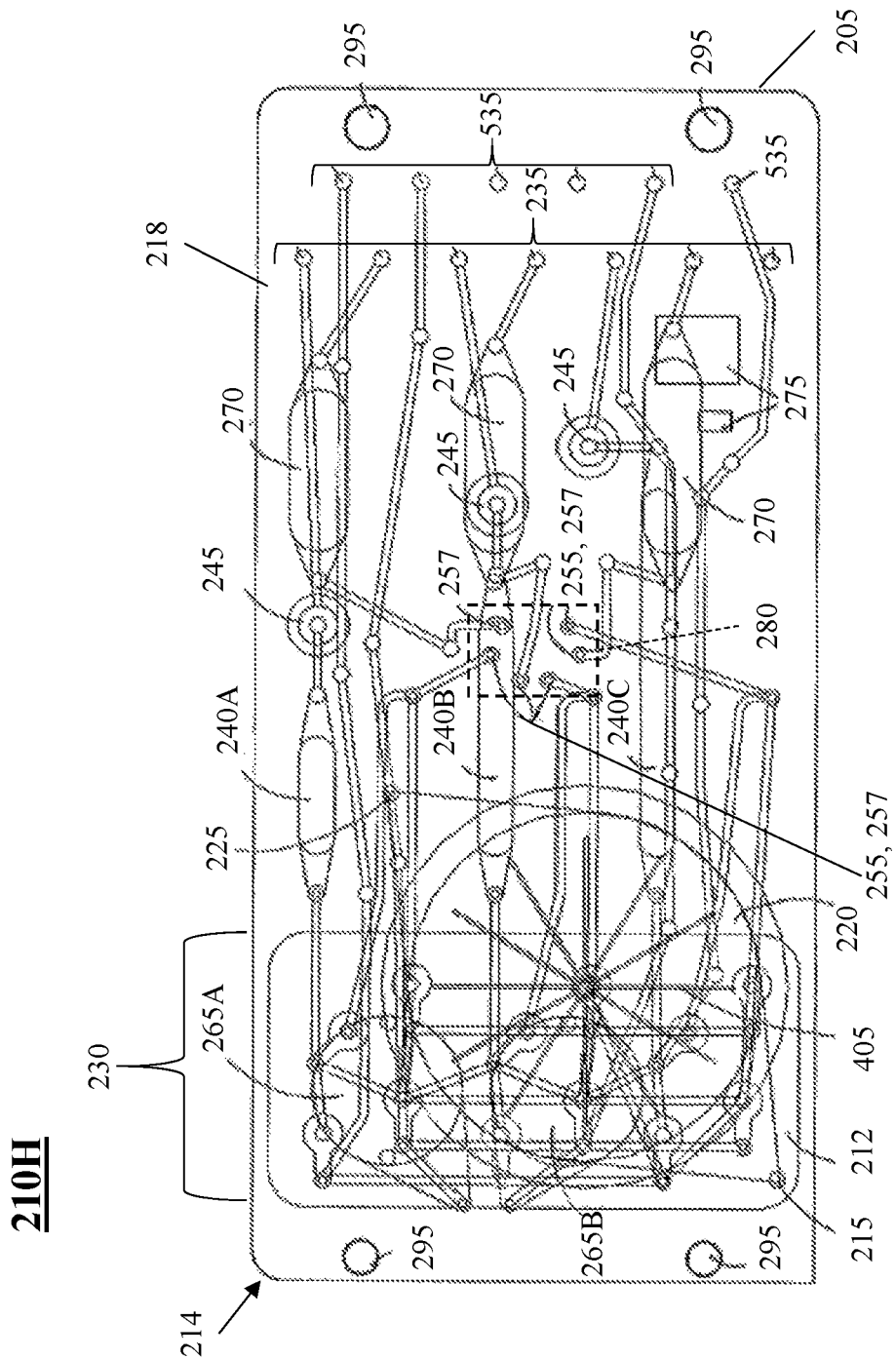
FIG. 23 illustrates a top view of an exemplary assay sample processing card configured for use in a cartridge assembly, that determines dissociation constants for antibodies, in accordance with yet another embodiment.
Figure 24A:
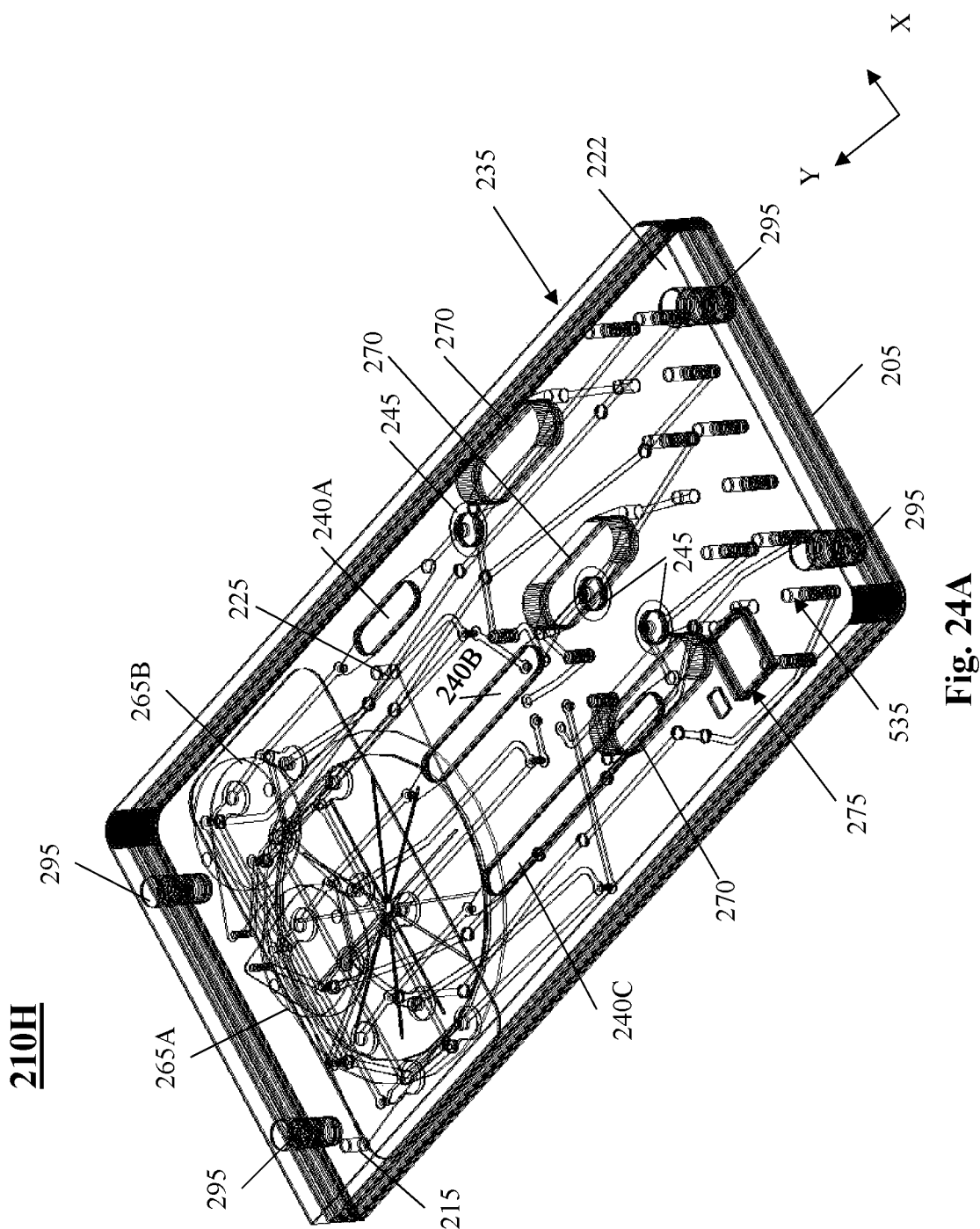
FIG. 24A is an angled view of the card of FIG. 23 from an underside thereof.
Figure 24B:
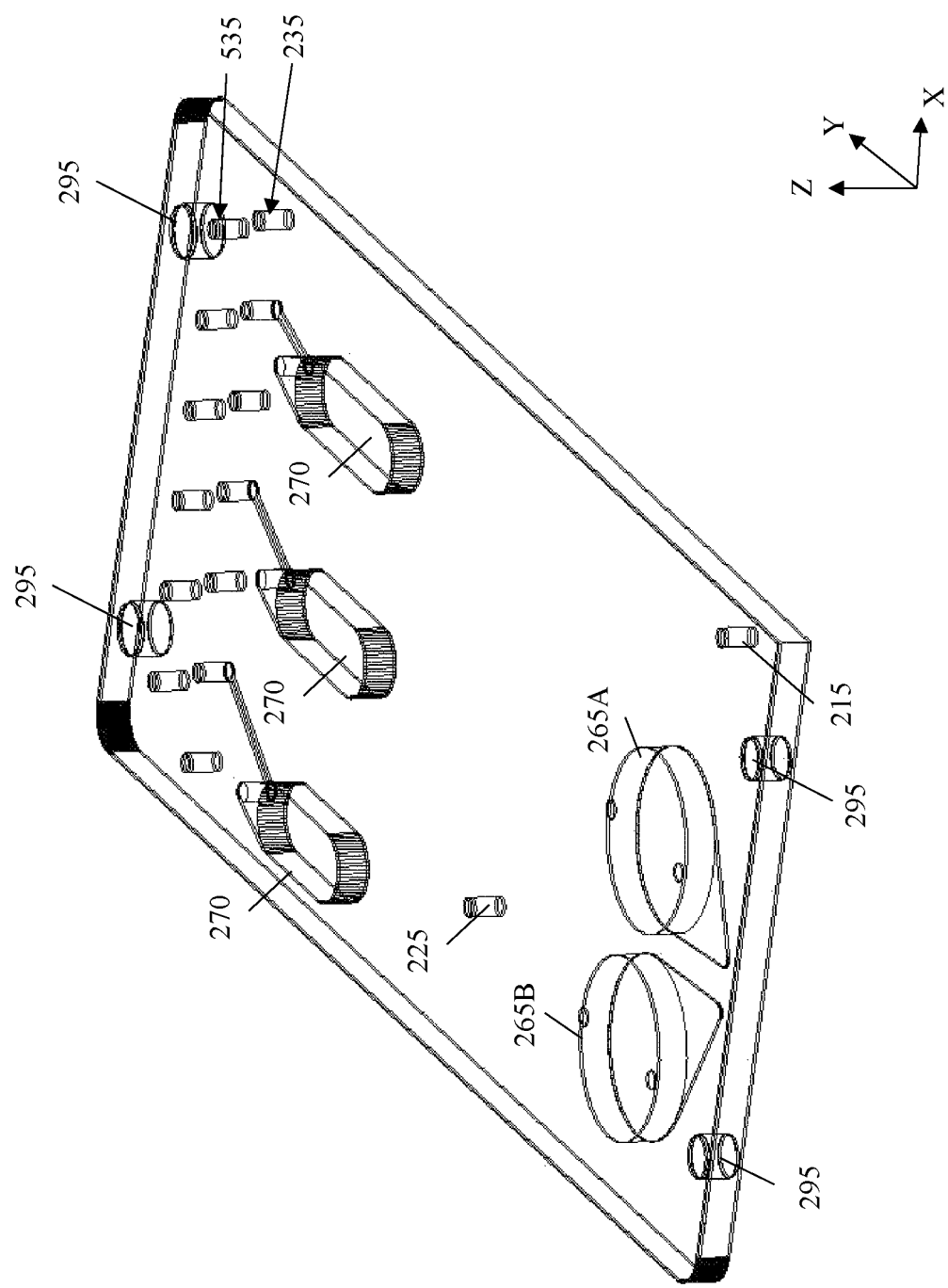
FIGS. 24B and 24C show an angled view and a top view, respectively, of an exemplary top layer of the card shown in FIGS. 23 and 24A.
Figure 24C:
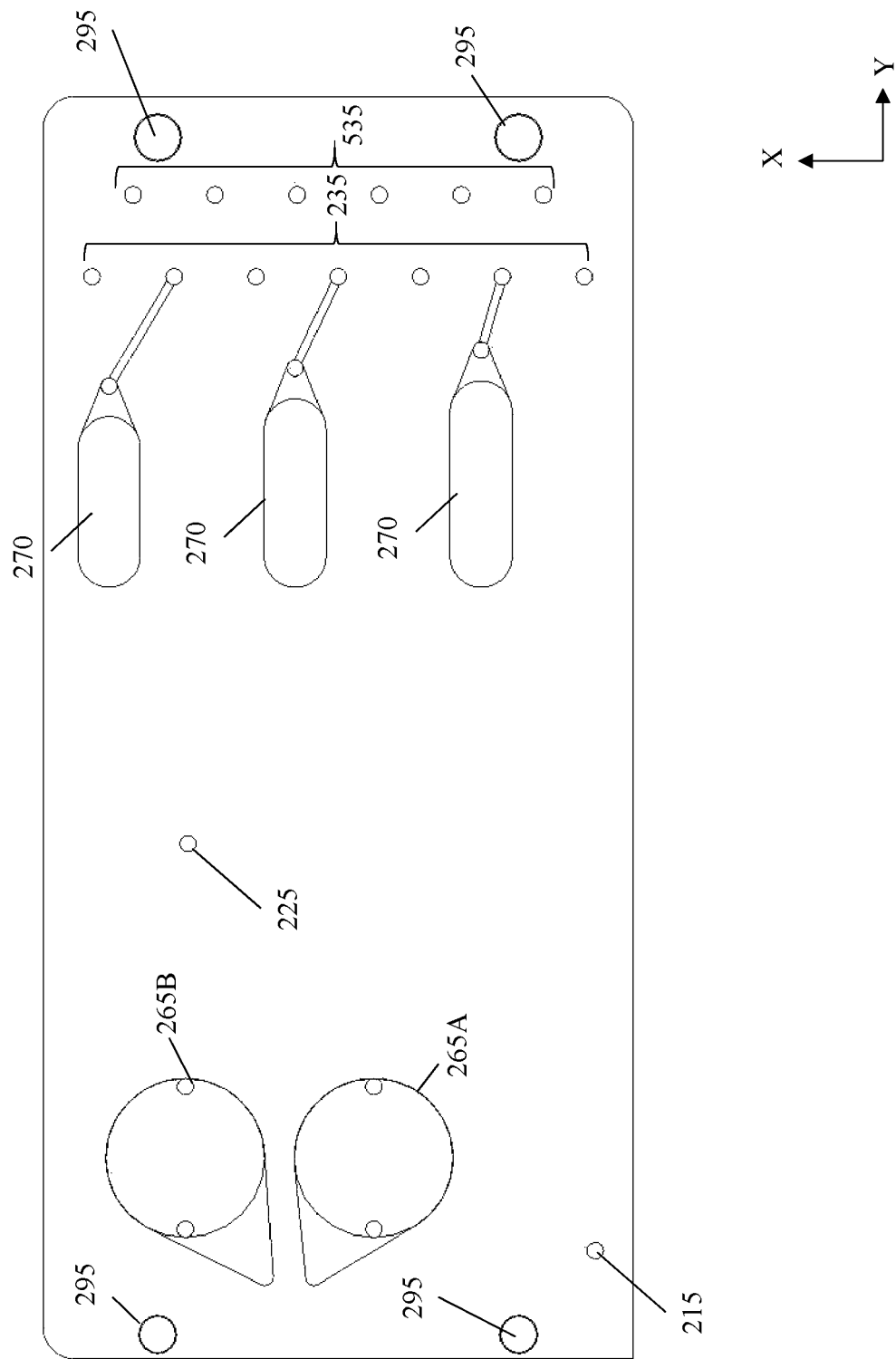
Figure 24D:
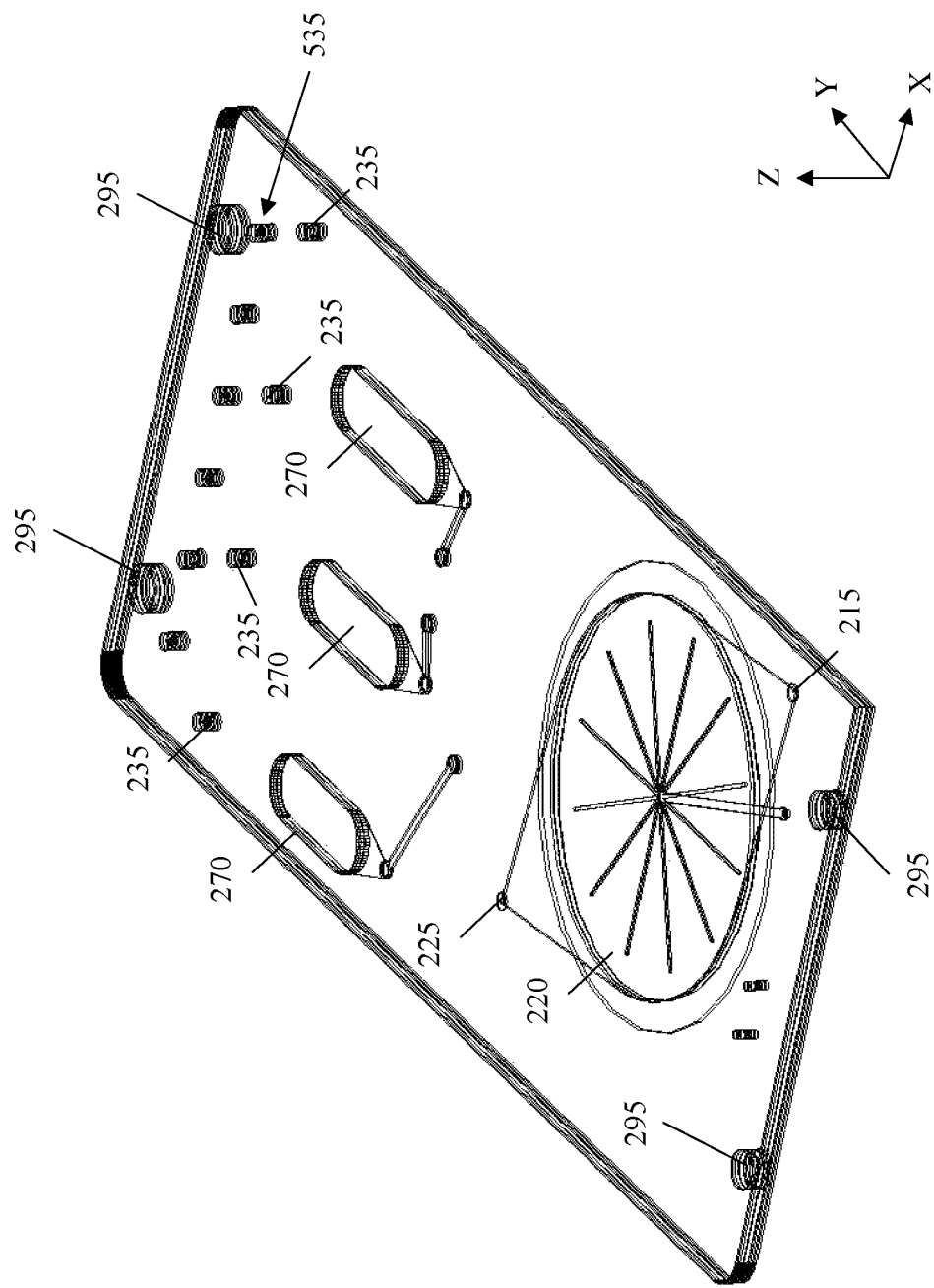
FIGS. 24D and 24E show an angled view and a top view, respectively, of an exemplary second layer of the card shown in FIGS. 23 and 24A.
Figure 24E:
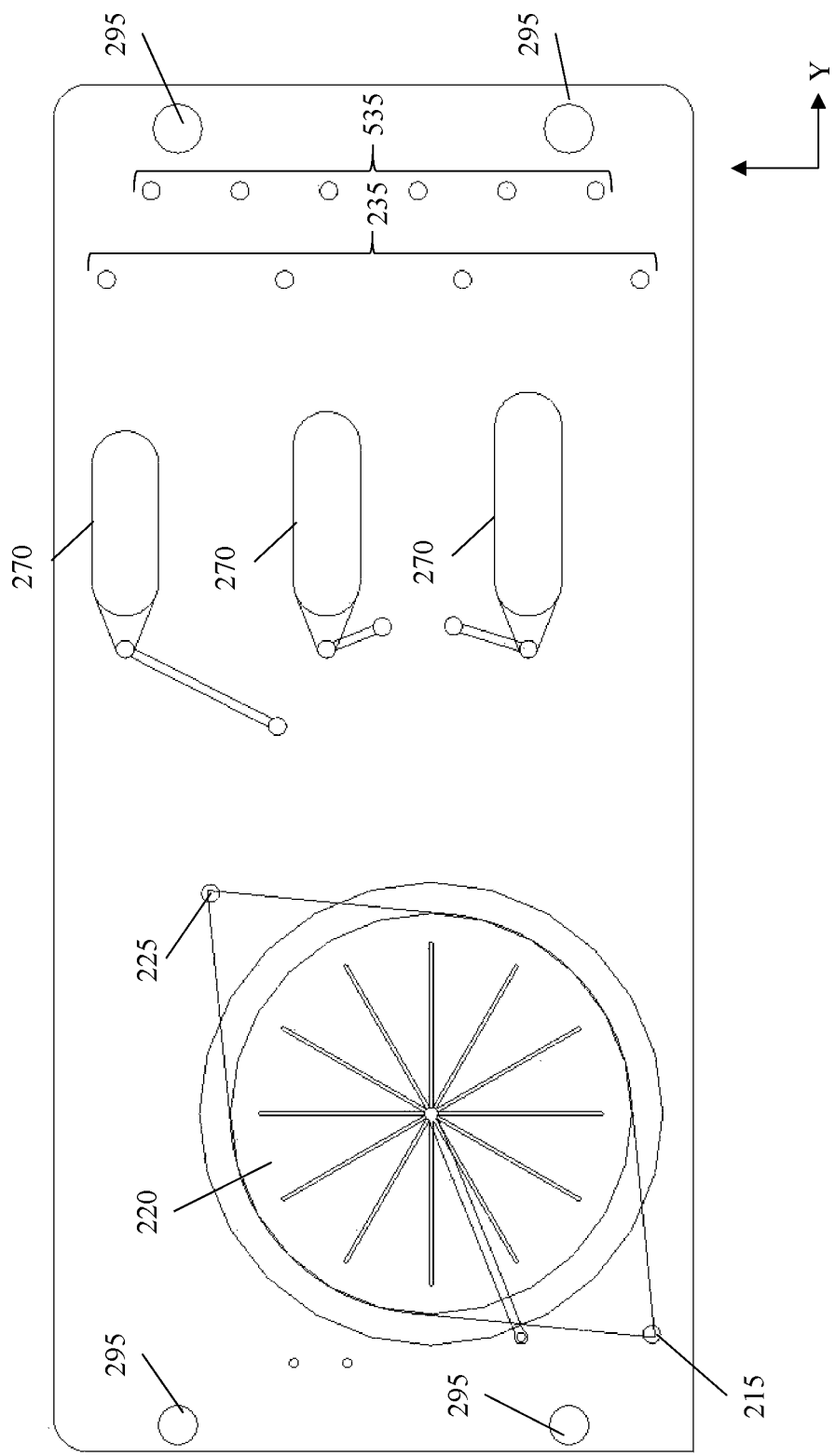
Figure 24F:
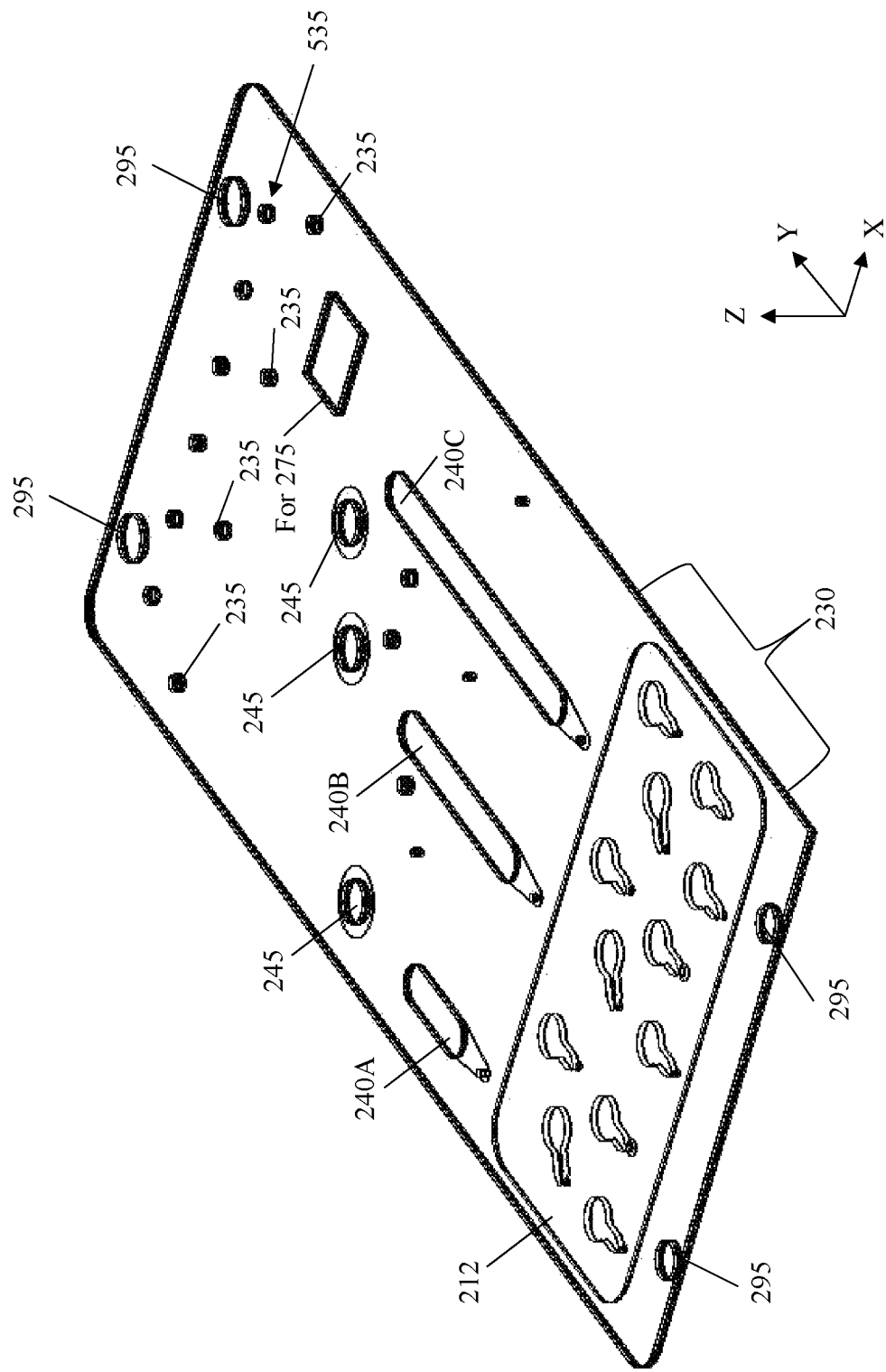
FIGS. 24F and 24G show an angled view and a top view, respectively, of an exemplary third layer of the card shown in FIGS. 23 and 24A.
Figure 24G:
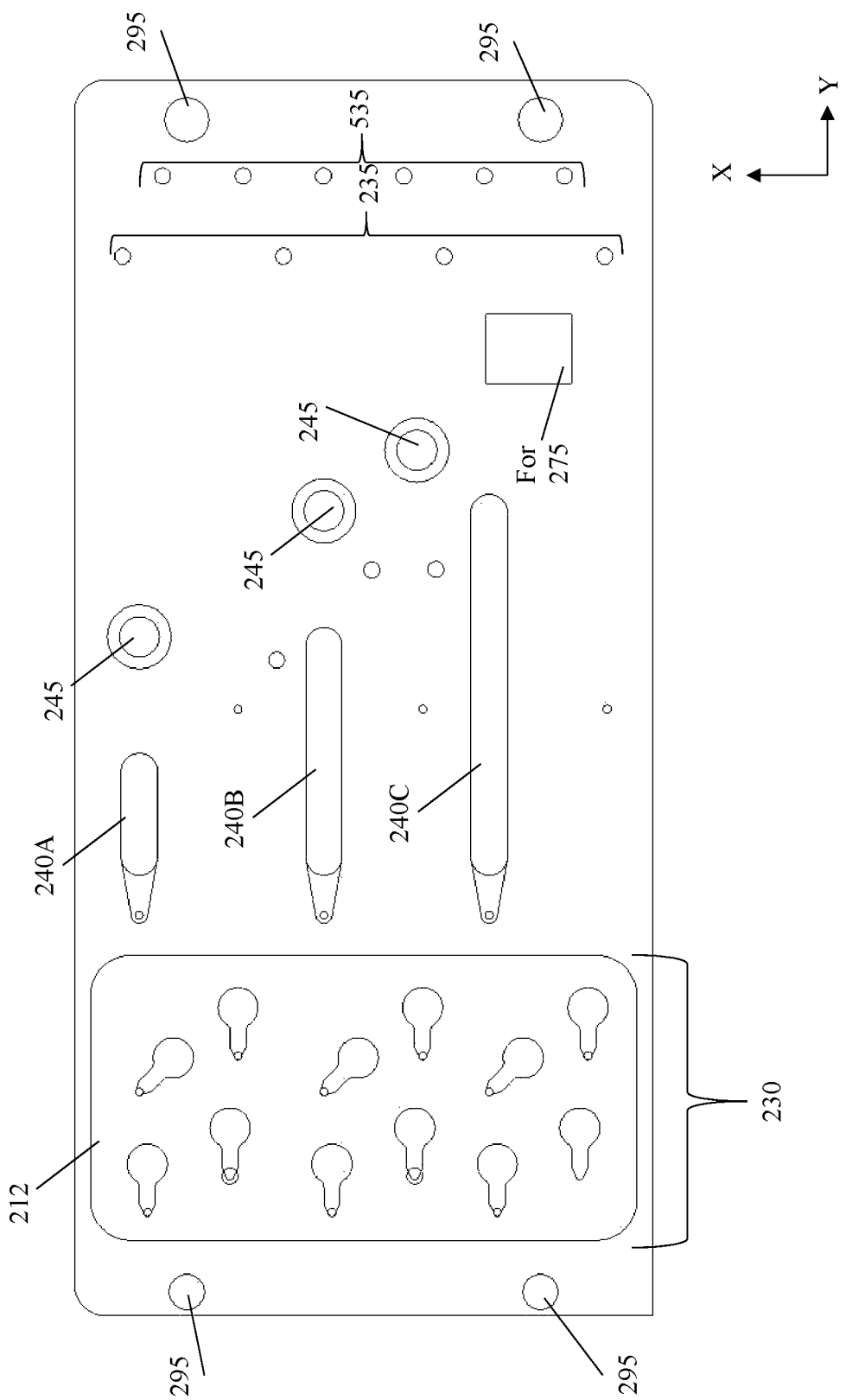
Figure 24H:
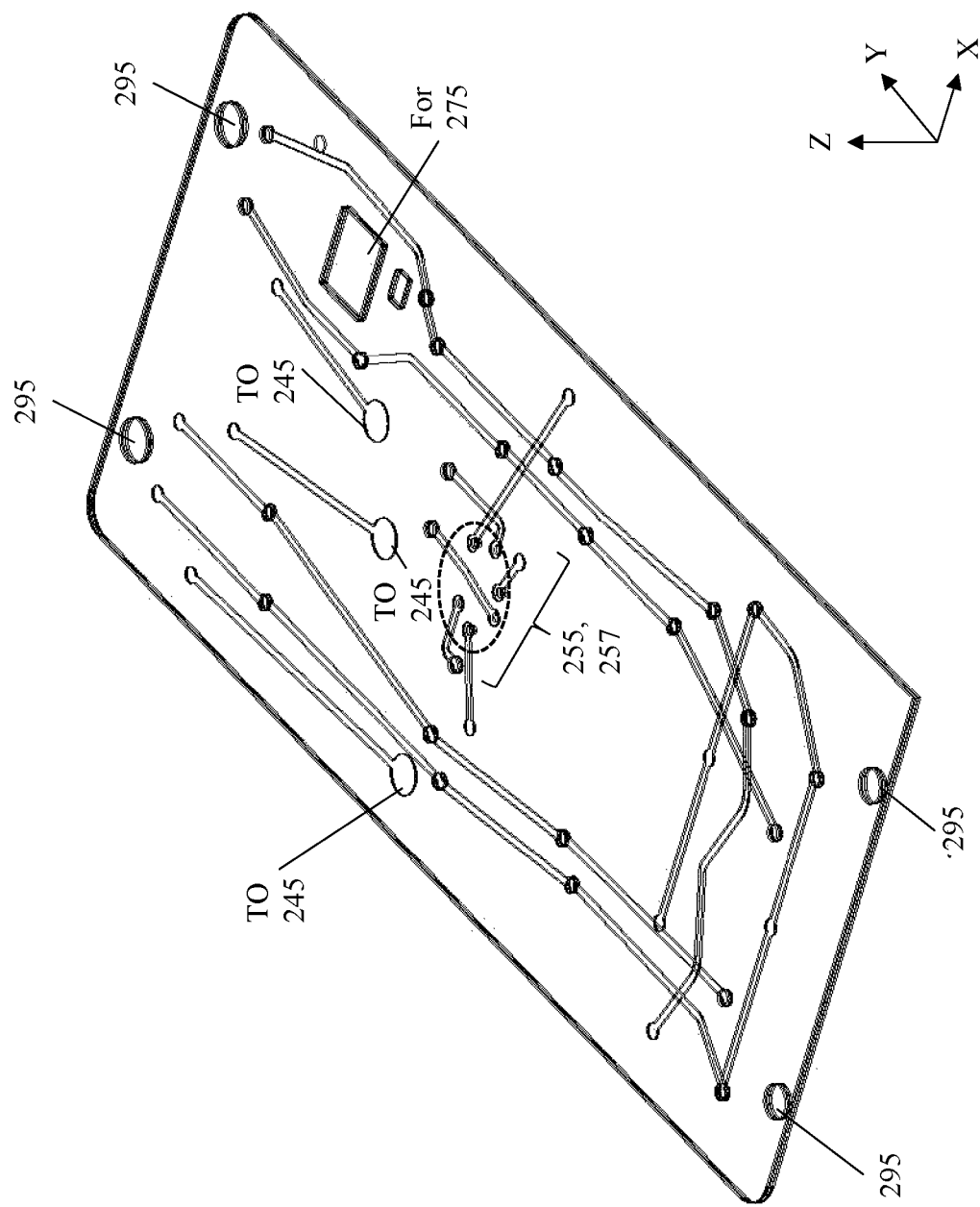
Figure 24I:
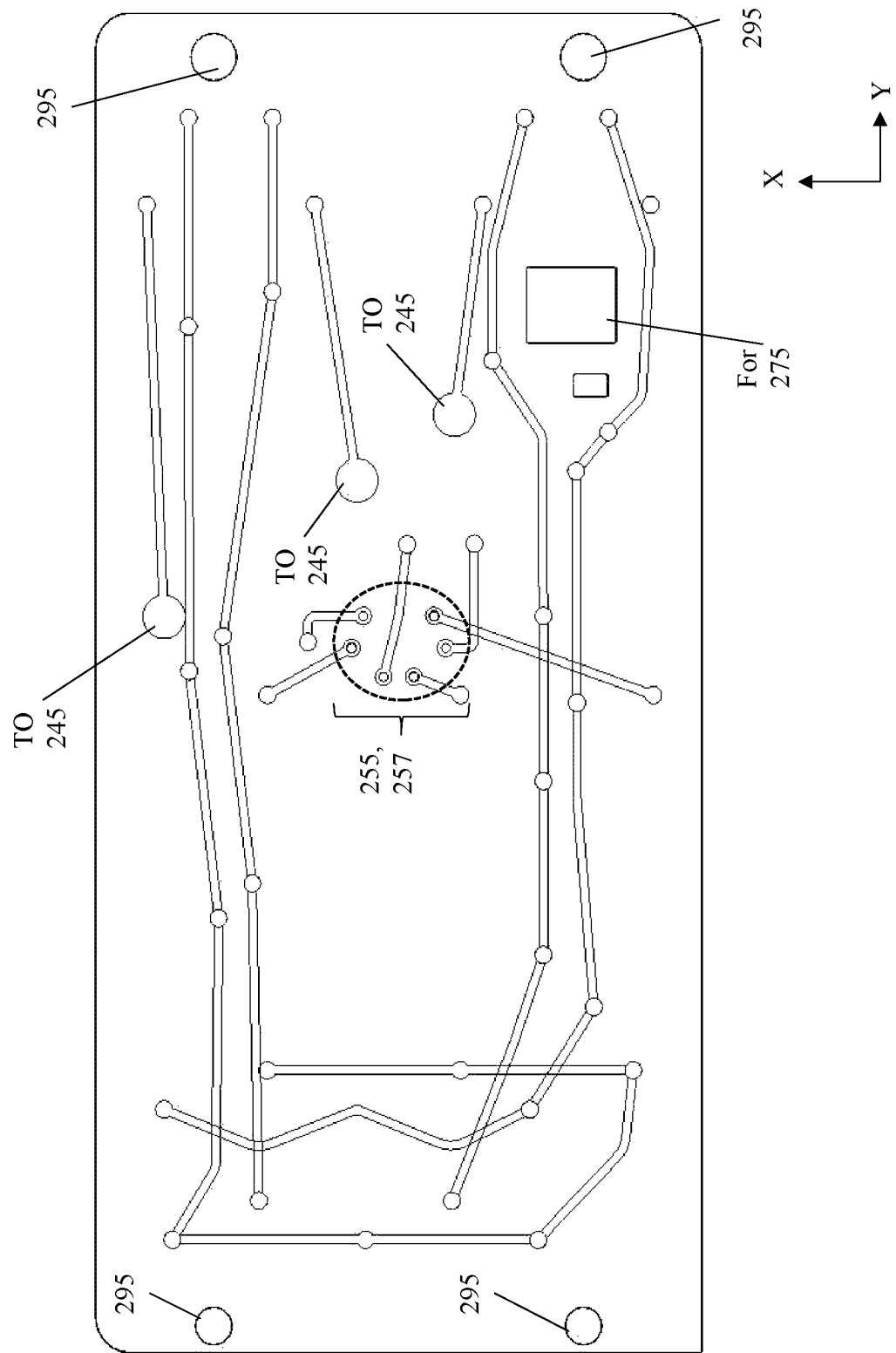

FIGS. 23 and 24A-24I illustrate an exemplary assay sample processing card 210H configured for use as a sample processing card in a cartridge assembly 200 which is configured for use in cartridge reader unit 100, in accordance with an embodiment herein. Although not expressly shown, it should be understood that the bottom (222) of card 210H may positioned against the top of the substrate 202, and optionally adhered to the substrate 202, as previously described. Substrate 202 may include a PCB, GMR sensor chip 280, electrical contact points 290, memory chip 275, optional heaters, and/or alignment devices 295, in accordance with an embodiment. One or more cut-out sections may be provided, e.g., on and/or through the bottom surface 222 (see FIG. 24A) in the card 210H to accommodate receipt of a portion of the GMR sensor chip 280 and/or on-board memory chip 275 of the substrate 202. The card 210H may be configured to determine dissociation constants for antibodies, in accordance with yet another embodiment. More specifically, as noted herethroughout in the described embodiments, the sample processing card 210H may be formed from layers and/or contain parts at different depths therein. Alignment devices 295 may be provided in each of the layers. FIGS. 24A-24I show an example of locations of the different parts and features of the card 210H in a depth of the card (or in a different layer) in greater detail. The features described below are provided in the card 210H and formed such that they can communicate and move fluid/blood/sample/air throughout the card at different depths or layers. FIG. 24A shows features in the layers of card 210H as viewed from an underside or bottom 222 thereof. FIGS. 24B and 24C show an angled view and a top view, respectively, of an exemplary top layer of the sample processing card 210H showing blister packs 265A and 265B, and ports 235, 535, and waste tanks 270 provided at a depth therein. FIGS. 24D and 24E show an angled view and a top view, respectively, of an exemplary second layer of the sample processing card 210H showing a blood filter membrane 220 and injection and vent ports 215, 225, and part of the waste tanks 270 and ports 235, 535 as formed at a depth therein. FIGS. 24F and 24G show an angled view and a top view, respectively, of an exemplary third layer of the sample processing card 210H showing valve area 230 with elastomeric material 212, GPMs 245, and metering chambers 240A, 240B, 240C at a depth therein, along with previously noted features. It is noted that reference to first, second, third, etc. herein is not intended to suggest a specific order and/or layering setup for the card 210H; rather, just different layers that may be provided in the card. Valves in a valve array zone 230 may be provided relatively below the filtration membrane 220 in the vertical (Z) direction, in accordance with one embodiment. In another embodiment, valve array zone 230 may be provided relatively above the filtration membrane 220. As shown in FIG. 23, each fluid metering chamber 240A to 240C may extend longitudinally between the valve array zone 230 and waste tanks 270. Each of the chambers 240 (three are shown here) may be positioned at a depth within the housing (in the Z-direction), between the top and bottom surfaces 218 and 222 of the card 210H, and in a manner such that they are parallel to one another in a lateral direction of the housing and extend a length in the longitudinal direction relative to the centerline A-A. Pneumatic control ports 235 (shown in FIG. 23 as two parallel rows of ports (e.g., ports 235) near a front end 205 of the card 210H, connected to communication channels within the card) (which may be part of a pneumatic/pump interface) and alignment devices 295 (e.g., holes) may be provided on a top surface 218. FIGS. 24H and 24I show an angled view and a top view, respectively, of an exemplary bottom layer of the sample processing card 210H showing GMR output ports 255 (to GMR sensor chip 280) and input ports 257, and air/fluid flow communication channels therein. These channels fluidly connect at least some of the above noted features to each other, for example. Of course this is an illustrative example in accordance with one embodiment. The depth and positioning of the channels and features and layers therein may be altered.

The card 210H may be a two-step, no wet dilution card (or 2SND) for such detection schemes. The method steps for use of card 210H as part of a cartridge assembly 200 that is inserted into cartridge reader unit 100 may be as follows:

1) Load patient sample (blood, urine, saliva, ocular fluid) into sample injection ports 215 (or a single port 215, with the other, opposite illustrated port being a vent port 225).

2) Puncture blister packs 265A and 265B.

3) Activate pneumatic system 330 by connecting to ports 235 to draw blood through membrane 220, through delivery channels 405, over elastomer valve region 212 of valve array zone 230, and into fluid metering chambers 240A-C (which may contain dry reagent, e.g., powder, for mixing with the plasma from blood) until fluid reaches GPMs 245.

4) Once all three GPMs 245 are wetted, reverse direction of pneumatic force on pneumatic control ports 235 to pull fluid from metering chambers 240A-C across elastomer valve region 212, and into the GMR sensor chip 280 via the outlet ports 255.

5) Continue pulling fluid until deposited into waste tanks 270.

6) Activate pneumatic system change via valve ports 535 to open channels to blister pack 265A.

7) Pull fluid from blister pack 265A across elastomer valve region 212, and into GMR sensor chip 280 via output ports 255.

8) Continue pulling fluid until fluid is deposited into waste tanks 270.

9) Repeat steps 6-8, with only change being fluid is pulled from blister pack 265B.

10) GMR signal is measured as the fluid from blister packs 265B, which contained the MNPs, is flowed across the sensor.

Figures 25, 26:
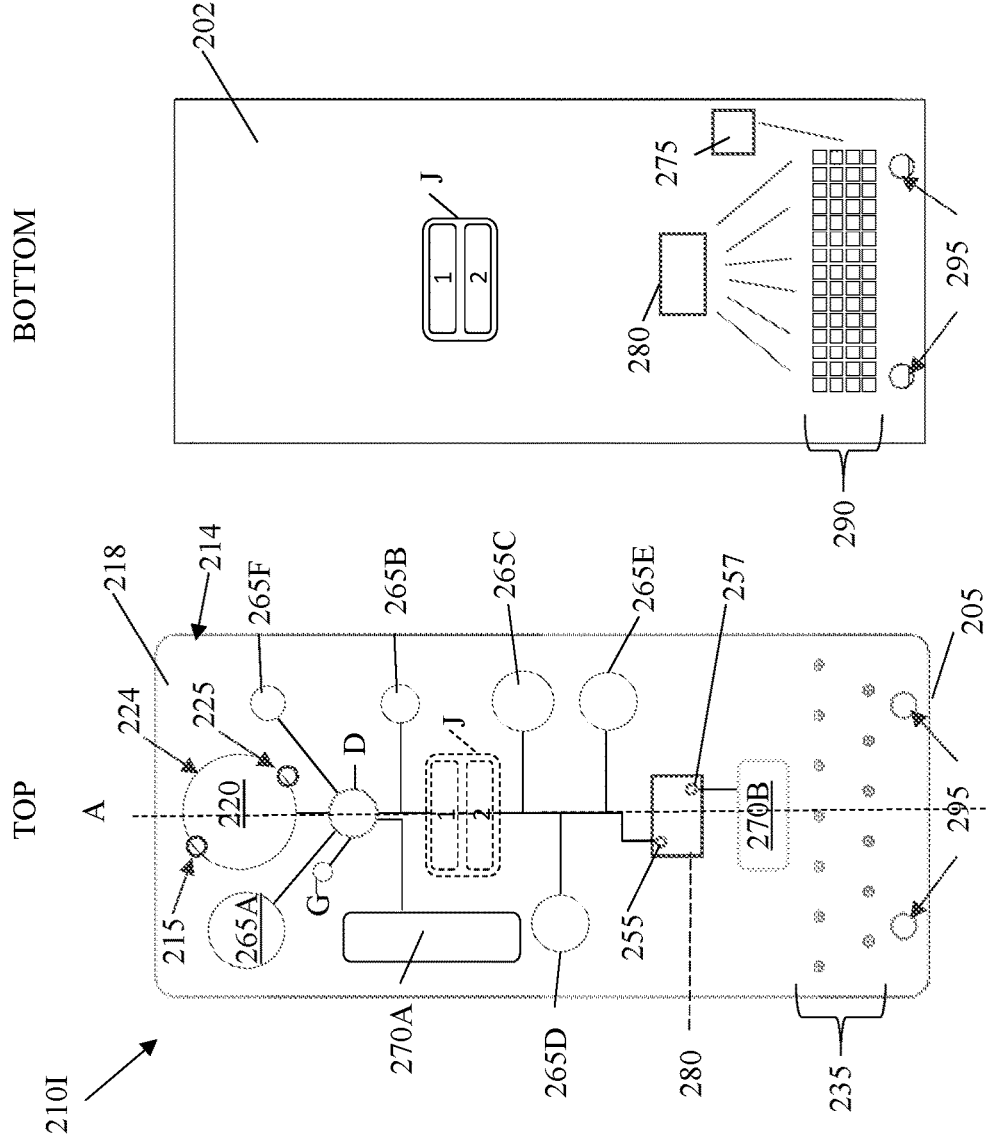
FIGS. 25 and 26 illustrate a top and a bottom, respectively, of another exemplary assay sample processing card configured for use in a cartridge assembly, that determines relative kinetics for antibodies, in accordance with another embodiment herein.

FIGS. 25 and 26 illustrate a top and a bottom, respectively, of another exemplary cartridge assembly 200 including an exemplary assay sample processing card 210I configured for use as a sample processing card in a cartridge assembly 200 which is configured for use in cartridge reader unit 100, in accordance with an embodiment herein. Although not expressly shown, it should be understood that the bottom (222) of card 210I may positioned against the top of the substrate 202, and optionally adhered to the substrate 202, as previously described. The card 210I may be configured to determine an influenza strain, in accordance with yet another embodiment herein. In an embodiment, this card 210I may also be configured for use with a high-salt solution buffer containing viral RNA with a (cheek or buccal) swab sample. Again, for the sake of brevity, previously described features—such as outlet port 255 and input port 257 to the GMR sensor chips 280, waste chambers 270A, blister packs 265, etc.—are labeled in FIGS. 25-26 with same or similar reference numbers, and thus not necessarily repeated here. Pneumatic control ports 235 (shown in FIG. 25 as two parallel rows of ports (e.g., ports 235) near a front end 205 of the card 210I, connected to communication channels within the card) (which may be part of a pneumatic/pump interface) and alignment devices 295 (e.g., holes) may be provided on a top surface 218, and electrical contact pads 290 and/or alignment devices 295 may be provided on a bottom surface (e.g., underside of the substrate 202), as shown in FIG. 26. During use, for example, a buccal swab sample may be injected into injection port 215 and filtered via filter 220 into receiving area 224 or sample chamber. Wash buffer1 may be provided in blister pack 265A, PCR reagents may be provided in blister pack 265B, an enzyme may be provided in blister pack 265C, Wash buffer2 may be provided in blister pack 265D, and magnetic beads solution (e.g., Streptavidin-coated beads) may be provided in blister pack 265E. Eluant may be provided in blister pack 265F. Pneumatic control ports 235 are provided on the card 210I for pneumatic control of fluids therein. Memory 275 may provide features for controlling the card 210I as well as store array parameters. Waste reservoirs 270A and 270B are also provided.

Also included on card 210I are glass fiber membrane (D) (which may be similar to the previously described glass fiber membrane 220A), Air vent (G) (which may be similar to vent port 225). PCR heating zones (J) and two heaters (1&2) may be provided on the substrate 202. In an embodiment, the heaters 1&2 are configured to operate at different temperatures, Further, in an embodiment, to utilize the card 210H for influenza testing, influenza strain specific single strand DNA (ssDNA) fragments may be printed on sensor 280 during card 210I and cartridge assembly 200.

The method steps for use of card 210I as part of a cartridge assembly 200 that is inserted into cartridge reader unit 100 may be as follows:

1) 300 uL of high-salt solution buffer containing viral RNA from buccal swab sample is injected into receiving area 224 through injection port 215 while air is vented at opposite vent port 225

2) Insert cartridge assembly so that alignment devices 295, pneumatic control ports 235, and electrical contact pads 290 connect to the cartridge reader 310 in the cartridge reader unit 100

3) Read parameters from on-cartridge memory 275 to instruct cartridge reader unit 100 how to reproduce the assay (i.e. complete the steps below in this sequence)

4) Glass fiber membrane (D) capture viral RNA from sample in receiving area 224 and are directed into waste reservoir 270A via application of pressure through ports 235

5) Puncture blister pack 265A to release 400 uL of wash buffer1

6) Wash buffer1 from blister pack 265A flows through glass fiber membrane (D) and into waste reservoir 270A 7) Open vent (G) to dry glass fiber membrane (D)

8) Puncture blister pack 265F to release 20 uL of eluant

9) Eluant from 265F elutes bound RNA on glass fiber membrane (D)

10) Puncture blister pack 265B to release 15 uL of PCR reagents

11) RNA eluent mixes with PCR reagents from blister pack 265B and goes to PCR heating zones (J)

12) RNA is first transcribed to DNA by heating at (45-55° C.) before starting PCR cycle.

13) PCR cycle: double strand DNA (dsDNA) denatures (separate dsDNA to two ssDNA) at heater #1 (94-96° C.), and primer annealing & elongation (generate dsDNA from ssDNA) at heater #2 (50-75° C.). One strand of the amplified dsDNA is biotinylated. Repeat these steps to amplify dsDNA 14) Puncture blister pack 265C to release 75 uL of exonuclease 15) Enzyme from blister pack 265C mixes with PCR product and the mix flows over sensor 280 and into waste reservoir 270B 16) Enzyme degrades dsDNA to ssDNA. Non-biotinylated ssDNA is degraded. Biotinylated ssDNAs then hybrid with the printed DNA fragments on sensor 280

17) Puncture blister pack 265D to release 100 uL of Wash buffer2

18) Wash buffer2 from blister pack 265D flows over sensor 280 and into waste reservoir 270B 19) Puncture blister pack 265E to release 100 uL of magnetic beads solution 20) Magnetic beads from blister pack 265E flows over sensor 280 and into waste reservoir 270B 21) Record GMR sensor signals at sensor 280 while beads bind to sensor surface: Streptavadin on beads bind to biotin on ssDNAs 22) Positive GMR sensor signals indicate the presence of influenza. Signal from each sensor is strain specific Electrical resistance change on sensor 280 is configured to be measured in real-time to indicate concentration of analyte. Sensor 280 is connected through electrical contact pads 290. Simultaneously, GMR signals from GMR sensor chip 280 may be recorded (e.g., on memory card 275 or a cloud server) and the results may be displayed in real time (e.g., via display 120 on cartridge reader unit 100).

Figure 27A:
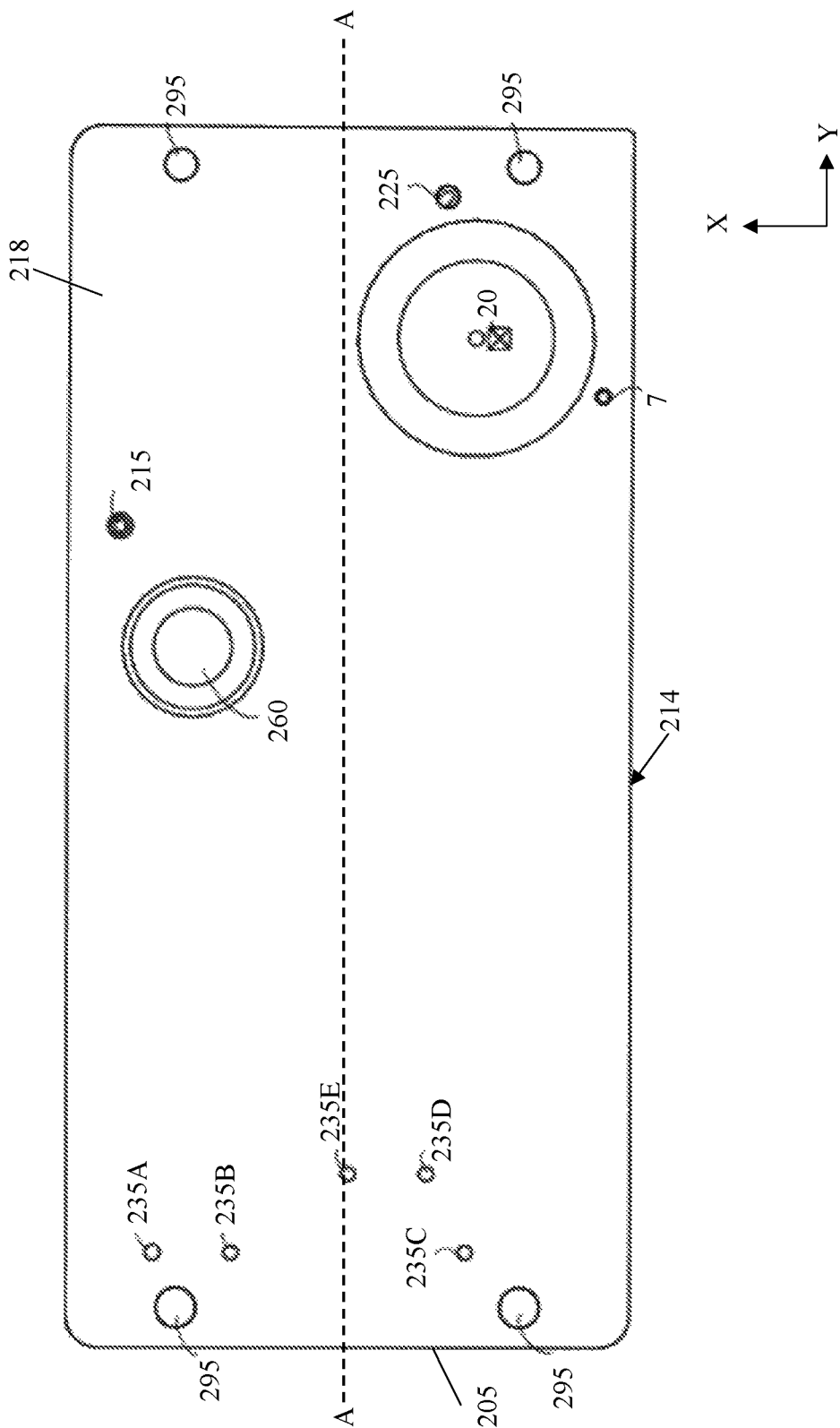
FIG. 27A shows a top view of a sample processing card configured for use in a cartridge assembly, in accordance with yet embodiment herein.
Figure 27B:
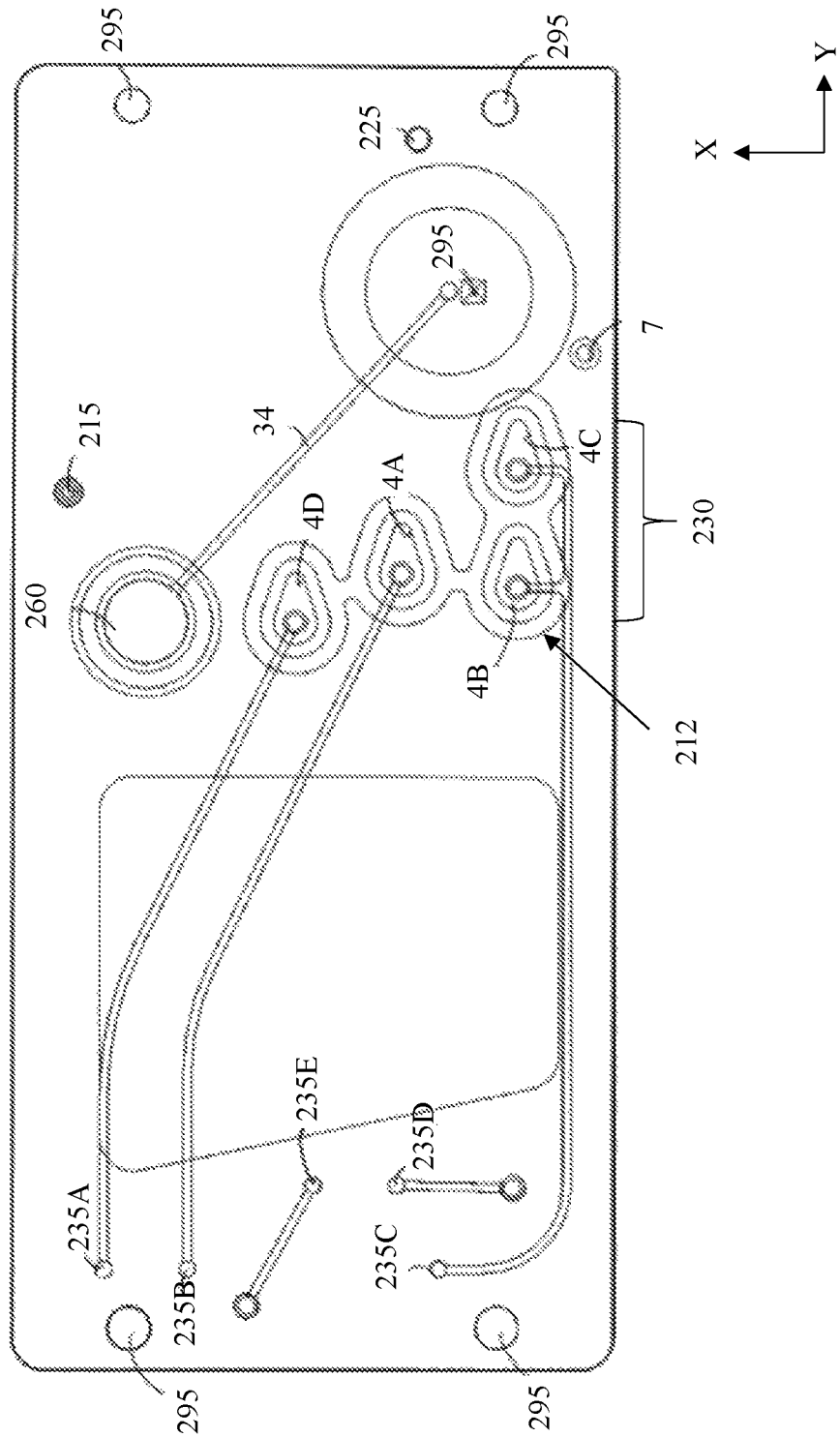
FIG. 27B shows a top view of an exemplary first layer of the sample processing card shown in FIG. 27A.
Figure 27C:
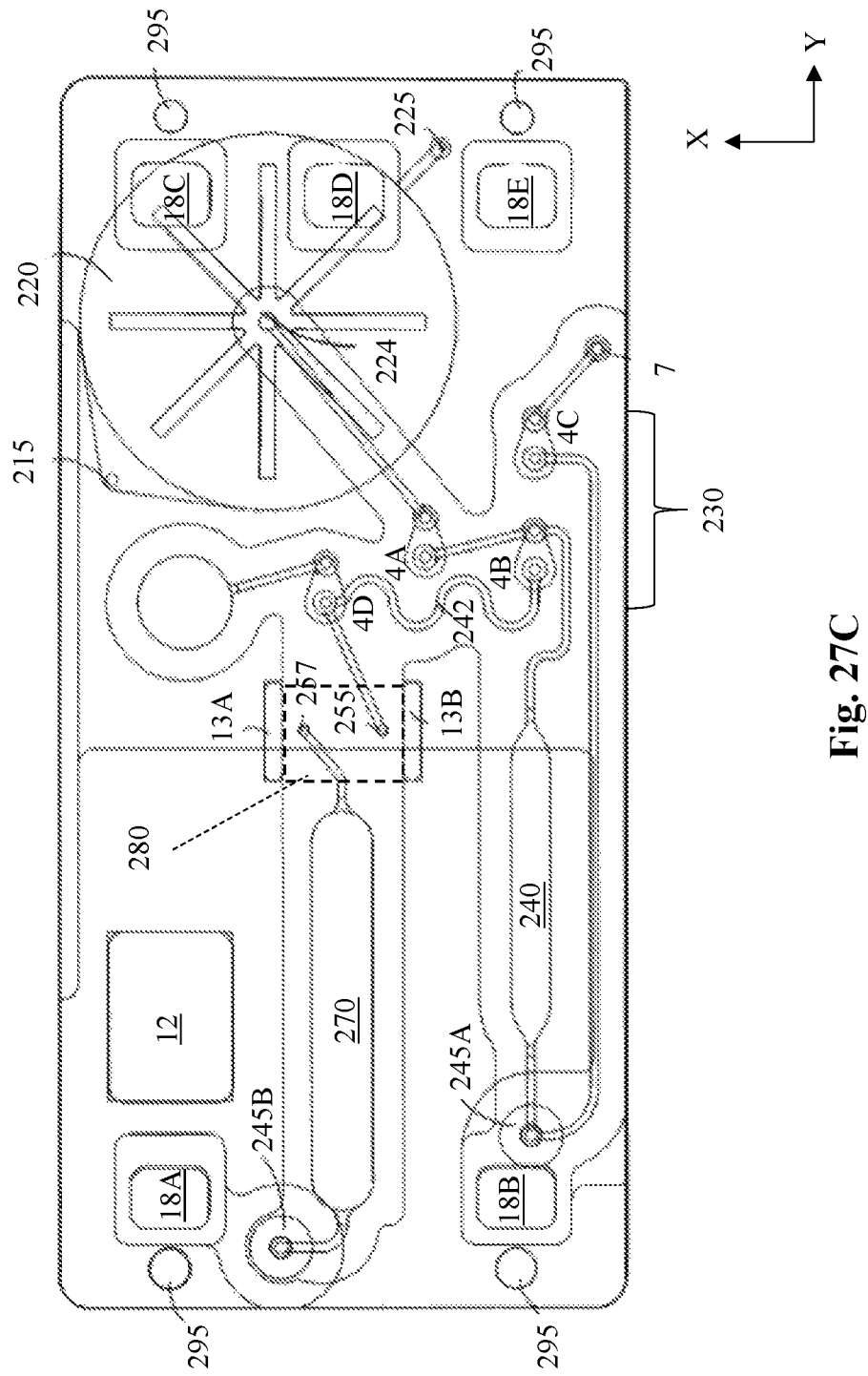
FIG. 27C shows a top view of an exemplary second layer of the sample processing card shown in FIG. 27A.
Figure 27D:
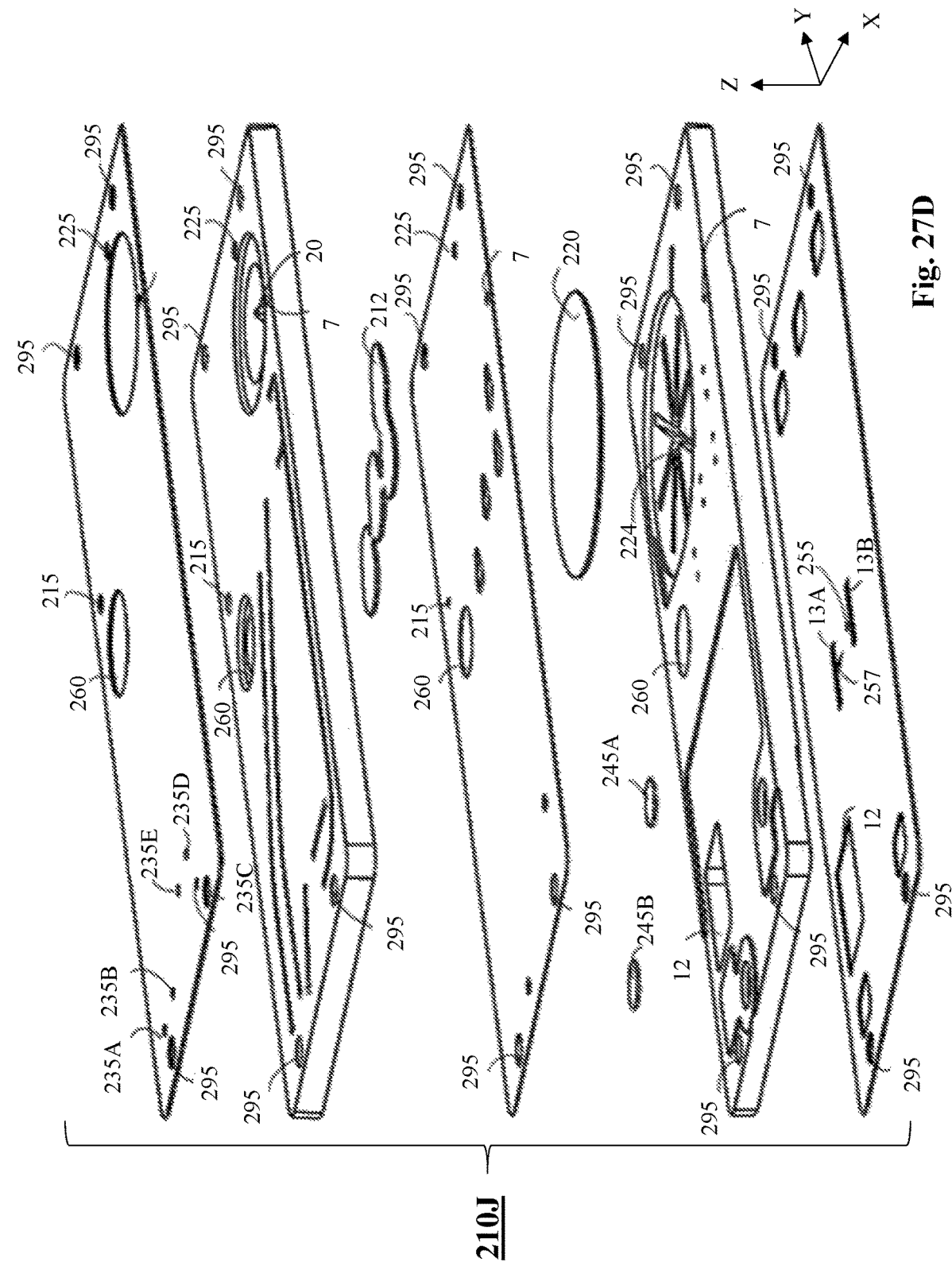
FIG. 27D shows an exploded view of exemplary layers and parts of the sample processing card shown in FIG. 27A.

FIG. 27A shows a top view of a sample processing card 210J, configured for use as a sample processing card in a cartridge assembly 200 which configured for use in cartridge reader unit 100, in accordance with an embodiment herein. As noted herethroughout in the described embodiments, the card 210J may be formed from layers and/or contain parts at different depths therein. FIGS. 27B, 27C, and 27D show examples of some of the layers and features, thus locations of the different parts and features, in a depth of the card 210J in greater detail. The features described below are provided in the card 210J and formed such that they can communicate and move fluid/blood/sample/air throughout the card at different depths or layers. Although not expressly shown, it should be understood that the bottom (222) of card 210J may positioned against the top of the substrate 202, and optionally adhered to the substrate 202, as previously described. Substrate 202 may include a PCB, GMR sensor chip 280, electrical contact points 290, memory chip 275, optional heaters, and/or alignment devices 295, in accordance with an embodiment. Pneumatic control ports 235 (shown in FIG. 27A as an assembly of ports 235 near a front end 205 of the card 210J, connected to communication channels within the card) (which may be part of a pneumatic/pump interface) and alignment devices 295 (e.g., holes) may be provided on top surface 218. FIG. 27B shows a top view of an exemplary first layer of the card 210J showing features such as reagent well 260, sharp feature 20, valves 4A-4D of the valve array 230, and ports 235A-235E. Valves 4A-4D in a valve array zone 230 may be provided relatively below the filtration membrane 220 in the vertical (Z) direction, in accordance with one embodiment. In another embodiment, valve array zone 230 may be provided relatively above the filtration membrane 220. FIG. 27C shows a top view of an exemplary second layer of the card 210J showing a serpentine channel 242, a filtration membrane 220, metering chamber 240, waste chamber 270, and some other parts from the first layer at a depth therein. The single metering chamber 240 of this embodiment may extend longitudinally between the valve array zone 230 and GPM 245. The chamber 240 may be positioned at a depth within the housing (in the Z-direction), between the top and bottom surfaces 218 and 222 of the card 210J, and may be provided on one side relative to the centerline A-A. FIG. 27D shows additional features and layers of the card 210J, used with the layers of FIGS. 27B-C. Of course this is an illustrative example in accordance with one embodiment. The depth and positioning of the channels and features and layers therein may be altered.

In use, a patient sample is loaded via pipette into an injection port 215, allowing the sample to flow across the filter membrane 220 surface towards a vent port 225. A magnetic bead solution is loaded into the reagent well 260. Alternatively, a blister pack containing magnetic bead solution may be placed above a sharp feature 20 (e.g. pin) that will pierce the blister pack and allow fluid to travel through the channel 34 and be deposited into the reagent well 260. Once the cartridge assembly 200 has been inserted into the cartridge reader unit 100, an off-card pneumatic system 330 is connected via manifold to the pneumatic control ports 235, which, as shown in FIG. 27A, may be provided at the front end the card. The first step of the assay uses the off card pneumatic system to supply vacuum and pressure to the channel of the card to elicit a mechanical change in the elastomer valve membrane 212 material, which is seated over specific valves 4A-4D in valve array zone 230. The assay begins with the opening of valve 4A and the closing of 4B-D, and a negative pressure applied to 235D to draw the sample through the filter membrane 220 material and into the collection channels of receiving area 224 therebelow. The filtered sample continues through the channel and across a valve 4A gate into a metering chamber 240. Inside the metering chamber 240 may be some dried reagent that the assay requires be mixed with the patient sample via diffusion. The fluid continues to flow into this channel until it wets a gas permeable membrane 245A, which signals to the external system (cartridge reader 310) that the step has completed. The second step in the assay procedure involves the opening of valve 4C, which vents the metering chamber 240 line to atmosphere through a via air vent 7 (or port) located at the rear/other end of the card. Another valve 4B is also opened, while valve 4A is closed. The fluid is the drained from the metering chamber 240 across the open valve 4B and though a serpentine mixing feature 242 towards the output port 255 to GMR sensor 280 (which is located on an attached substrate 202, not shown, but whose location is generally represented in FIG. 27C). fluid enters the outlet port 225 and is drawn through the sensor 280, then back into the card through the inlet/input port 257, to be deposited into the waste chamber 270. This fluid movement is achieved through negative pressure at pneumatic port 235E, with gas permeable membrane 245B preventing any fluid from entering the off card pneumatic infrastructure from the waste chamber 270. The third step of the assay closes the previously opened valves 4B-C and opens valve 4D. The magnetic nanoparticles are drawn into the GMR sensor 280 via the outlet port 225 and exit from the GMR sensor via inlet or input port 257 into the waste tank 270. The detection stage occurs when the magnetic nanoparticles begin flowing across the GMR sensor, and assay completion is when the volume of the solution in the waste tank 270 is such that it wets the gas permeable membrane 245B, informing the system that the test is complete.

In addition to the above described features, card 210J may also include features 13A/B that are cut into the bottom of the card near the GMR sensor interface, whose purpose is to avoid contacting any epoxy along the wire bonding on the sensor. Another feature 12 is a cut out in the bottom of the card to prevent cartridge contact with hardware present on the PCB substrate that the cartridge is seated upon. The alignment devices 295 are used to align the cartridge components during assembly of the card 210J (e.g., during assembly of the layers) and for seating the cartridge assembly 200 into the cartridge receiver 130 (e.g., into the receiving tray) of the cartridge reader unit 100. The sharp feature 20 used to puncture the blister pack may be located near a top 218 of the card, e.g., in a top layer thereof. On the bottom 222 of the card 210 there may be a number (e.g., five) of standoffs 18A-E that support the card 210 on the PCB substrate 202 when attached thereto. The serpentine mixing channel 242 is designed to facilitate localized mixing of dried reagent and loaded sample.

The table below depicts pressure configured to be applied to the ports 235A-235E of the cartridge. A "+" indicates a positive pressure, and a "−" indicates a negative pressure, while an "x" indicates no pressure being applied. The pressure state of 235A, 235B, and 235C may be configured to control the elastomer valves 212 on the card 210J, where a negative pressure opens the valve, and a positive pressure closes the valve.

|  | P1 (air) | P2 (air) | P3 (air) | P4 (fluid) | P5 (fluid) |
|---|---|---|---|---|---|
| Assay Step 1 | − | + | + | − | x |
| Assay Step 2 | + | + | − | x | − |
| Assay Step 3 | + | − | + | x | − |

In accordance with yet another embodiment, to prepare a sample for processing using a sample processing card 210 that is part of a cartridge assembly 200 inserted into a unit 100, a patient sample such as whole blood is loaded onto the card through injection port. Pneumatic manifold connected to device via pneumatic ports draws liquid into the card, while valve ports control the open/closed configuration of the elastomer material used for valving. A negative pressure pulls the patient sample through the membrane, resulting in plasma. This plasma is drawn into the quantitation metering chambers until the fluid reached the gas permeable membranes. Off card transducers detect a pressure change once all three GPMs are wetted, at which point a positive pressure is introduced to the fluid, forcing the volumes from the metering chambers into the GMR sensor. As the fluid is pushed, it re-enters the card and is deposited into the waste tanks. The off-card pneumatics system changes the valve configuration via the pneumatic ports, allowing the wash buffer from a blister pack enter the card, flow across the GMR sensor=, and be deposited in the waste tanks. The same procedure is used for a blister pack containing the magnetic nano particles. Once all three fluids have passed through the card into the GMR sensor and into the waste tanks, the assay is complete.

In another embodiment, a sample preparation technique using a sample processing card 210 that is part of a cartridge assembly 200 inserted into a unit 100, a patient sample of any fluid may be loaded onto a filter membrane and drawn through using a negative pressure gradient supplied by off-card pneumatics, resulting in a cleaned or purified sample. Heat may be applied to the card to elicit a change in chemistry for the biomolecules stored inside, or as an intermediate step in some assay process such as PCR. Cooling may be applied to the card to influence the biochemical properties of the fluids being processed, or as a part of an assay process prior to sensing. Mixing of fluids in the card is achieved by selectively applying positive and negative pressures to the fluids to create a flow path across channel geometries comprised of sharp turns and vertical movements to expedite mixing of two dissimilar fluids. Dilution on-card is achieved by mixing a patient sample or filtered derivative with a reagent or buffer stored on-card. The mixing is mediated by driving the two fluids together using a positive or negative pressure gradient and drawing them through the geometries described above. In this way, the native concentration of select biomolecules present in a patient sample become less concentrated relative to the total volume of the mixed solution. Reagents are added by inducing a change in the valve elastomer material mediated by a positive or negative pressure produced from the off-card pneumatics system, opening the system to the reagent solution. This solution may then be drawn into the card and introduced to the assay. The card design may allow for the designation of regions for chemical reaction areas where two or more solutions may be combined and undergo a chemical change for use downstream in the assay. Heating and cooling operations may also be applied to this area as needed.

The herein disclosed cartridges may be fabricated by stacking and laminating different types and layers of laser cut, polymer materials, to produce the described channel geometries and shapes shown in the Figures. In addition to these layers, the gas permeable membrane, filtration membrane, and/or elastomer material zones and valves may also be laser cut and placed in designated regions of the cartridge to provide the required functionality. However, any number of manufacturing methods and/or materials may be used to manufacture the cartridges.

The herein disclosed cartridges uses interfaces, valves, and channels to allow for autonomous metering and mixture of (stored) reagents with a patient blood sample that is input therein as part of a single application or process. The metering of the fluids and subsequent mixing operations are controlled entirely by off-cartridge pump(s) and controller(s) that are connected to the cartridge, which allows for a complete automation of the assay process that previously required human technicians. The standardization of geometries and fluid movement also allows for a more stable platform, as more elements of the system are controlled.

Also, using such disposable point of care cartridges, a wider range of detection is possible while using a smaller amount of patient blood sample, without sacrificing speed in the production of results.

Further, the structural features of the disclosed cartridges permits multiple assays to run in parallel.

The illustrated structural features shown in the Figures of this disclosure are not intended to be limiting. For example, the numbers of sets, valves, metering chambers, membranes, mixing channels, and/or ports are not intended to be limited with regards to those shown. In some embodiments, more channels may be provided. In some embodiments, less channels may be provided. The number of valves is also not intended to be limiting. Also, although not necessary depicted in all of the Figures, it should be understood that each of the described sample processing cards 210 and/or cartridge assemblies 200 of FIGS. 5-27D may include the previously described receiving area 224 therein. Further, the location of the memory chip 275 on the substrate 202 is not intended to be limiting. As noted herein, in some embodiments, the sample processing card 210 may provide cut out sections to accommodate the memory chip 275 (e.g., in a case where memory chip 275 is provided on a top side of a substrate 202 and protrudes therefrom, and is placed against bottom 222 of the card 210 to form the cartridge assembly 200). In other embodiments, a face of the memory chip 275 may be placed against the bottom 222. In a similar fashion, the number and location of GMR sensor chip(s) 280, and any output ports 255 and input ports 257 associated therewith, as provided in the exemplary embodiments herein and shown in FIGS. 5-27D are also not intended to be limiting. Also, in some embodiments, the sample processing card 210 may provide cut out sections to accommodate the GMR sensor chip(s) 280 of the substrate 202 (e.g., in a case where sensor(s) are provided on a top side of a substrate 202 and protrude therefrom, and are placed against bottom 222 of the card 210 when forming the cartridge assembly 200). In other embodiments, a face of the GMR sensor chip(s) 280 may be placed against the bottom 222 (such as shown in FIGS. 2D and 2E).

In yet another embodiment, the cartridge assembly 200 may utilize an assay cartridge as its sample processing card 210 as disclosed in U.S. patent application Ser. No. 15/923,223, entitled "CARDIAC BIOMARKER ASSAY CARTRIDGE OR CARD", filed on Mar. 16, 2018, which is hereby incorporated by reference herein in its entirety.

Although the cartridge is described throughout as being used with a reagent and a patient or medical blood sample, it should be noted that the herein disclosed cartridges are not limited to use with blood or solely in medical practices. Another fluid(s) that may be separable and combined with a reagent or reactionary material may be employed in the herein disclosed cartridge for assaying.

In accordance with an embodiment, the described valving and fluid metering strategies could be replicated and utilized in other card designs as well. That is, the channels and/or elastomeric features (deflection portions), along with use of a pump and/or controller for pneumatic movement and control via pressurized air, may be applied to other card designs. Accordingly, the number and type of channels as shown in the Figures is not intended to be limited to the illustrated design; indeed, additional embodiments of sample processing card designs are described with reference to FIGS. 5-27A.

Any reference to any of the cards 210 and/or cartridge assembly 200 "in use", "during" use, and the like, as described herethroughout, refers to the cartridge assembly 200 being inserted into the cartridge reader unit 100, with an established electrical and pneumatic connection therebetween (e.g., via electrical contact portions 290 and pneumatic interface).

It should be understood that any reference to application of a magnetic field during processing as described with reference to FIGS. 5-27D refers to utilizing the aforementioned magnetic field generator 360 and/or second magnetic field generator provided within the cartridge reader unit 100.

The illustrated structural features shown in the Figures of this disclosure are not intended to be limiting. For example, the numbers of sets, valves, metering chambers, membranes, mixing channels, and/or ports are not intended to be limited with regards to those shown. In some embodiments, more channels may be provided. In some embodiments, less channels may be provided. The number of valves is also not intended to be limiting.

Although the cartridge assembly 200 and sample processing card 210 may be described herein as being used with a reagent and a patient or medical blood sample, it should be noted that the herein disclosed cartridge assembly 200 is not limited to use with blood or solely in medical practices. Other fluids that may be separable and combined with a reagent or reactionary material may be employed in the herein disclosed cartridge for assaying. Other samples may derive from saliva, urine, fecal samples, epithelial swabs, ocular fluids, biopsies (both solid and liquid) such as from the mouth, water samples, such as from municipal drinking water, tap water, sewage waste, ocean water, lake water, and the like.

Figure 28:
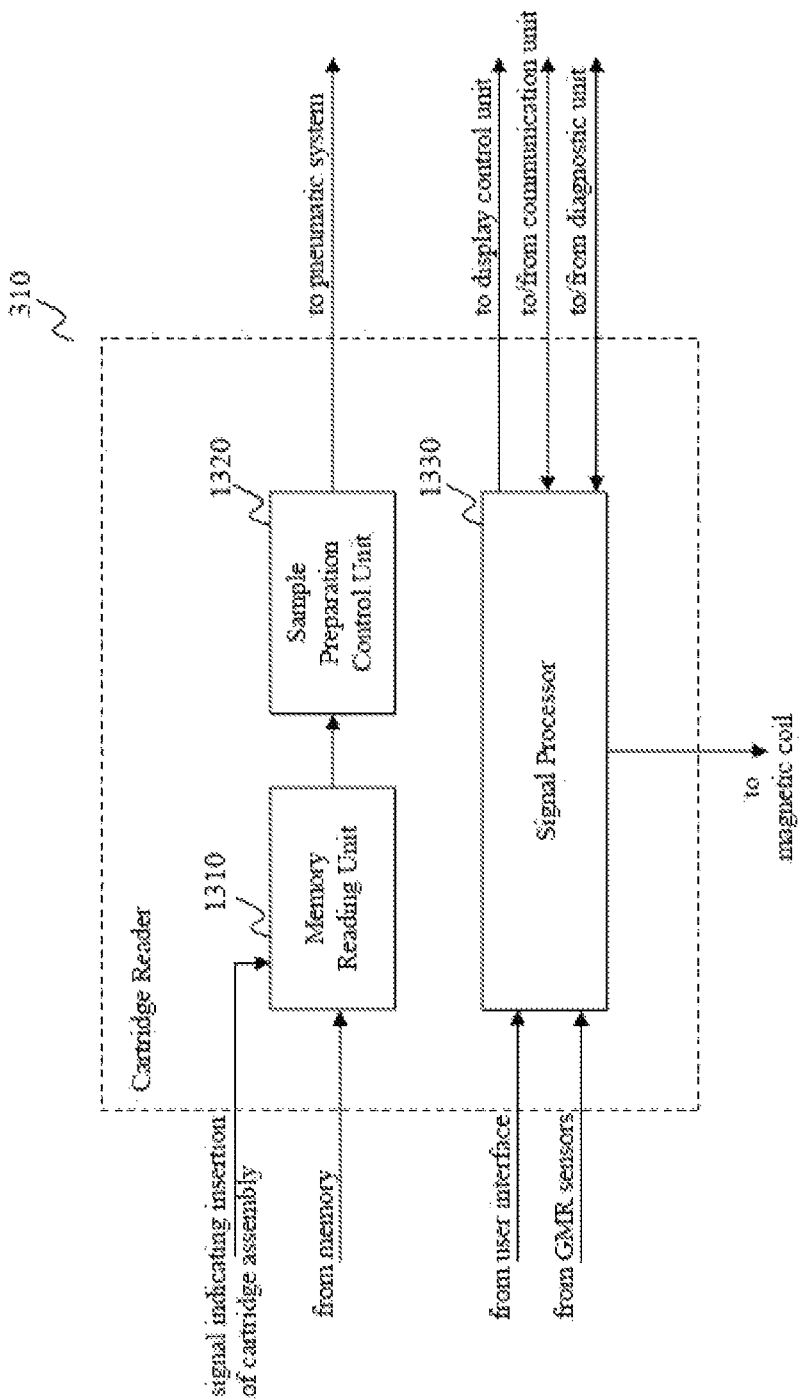
FIG. 28 schematically shows functional blocks of the cartridge reader in accordance with an embodiment of this disclosure.

FIG. 28 schematically shows functional blocks of the cartridge reader 310 in accordance with an embodiment. As shown in FIG. 28, the cartridge reader 310 may be divided roughly into a sample preparation control part and a signal processing part. A memory reading unit 1310 and a sample preparation control unit 1320 form the sample preparation control part. The memory reading unit 1310 may be adapted to, upon receipt of a signal indicating that a cartridge assembly 200 has been inserted into the cartridge reader 310, read information stored in the memory chip 275 on the cartridge assembly 200. The sample preparation control unit 1320 may be configured to, based on the information read from the memory chip 275, generate pneumatic control signals and send them to the pneumatic system 330. In some embodiments, when insertion of the cartridge assembly 200 into the cartridge reader 310 is recognized, an indication signal may be created by the cartridge assembly 200 and sent to the memory reading unit 1310 to inform of the insertion event. Alternatively, in other embodiments, such an indication signal may be created by other components at the cartridge reader 310 and sent to the memory reading unit 1310.

The signal processing function of the cartridge reader 310 is mainly performed by a signal processor 1330. The signal processor 1330 may be adapted to control electrical elements, prepare and collect signals, and process, display, store, and/or relay detection results to external systems. For example, the signal processor 1330 operates to generate a control signal for controlling the magnetic field generator 360, resulting in magnetic field excitation applied onto the GMR sensors in the cartridge assembly 200. After receiving measurement signals from the GMR sensors in the cartridge assembly 200 and from at least one reference resistor disposed in the cartridge assembly 200 and/or the signal processor 1330, the signal processor 1330 processes the measurements signals to obtain test results of the analyte detection. Via the display control unit 120, the test results may be displayed on an integrated or external display. Moreover, the signal processor 1330 may be coupled to the user interface 140 for receiving instructions from the user. Additionally, in some embodiments, the signal processor 1330 may be coupled to the communication unit 340 and/or with the diagnostic unit 350, enabling evaluation and diagnosis from the test results alone or in combination with other externally available data.

Figure 29:
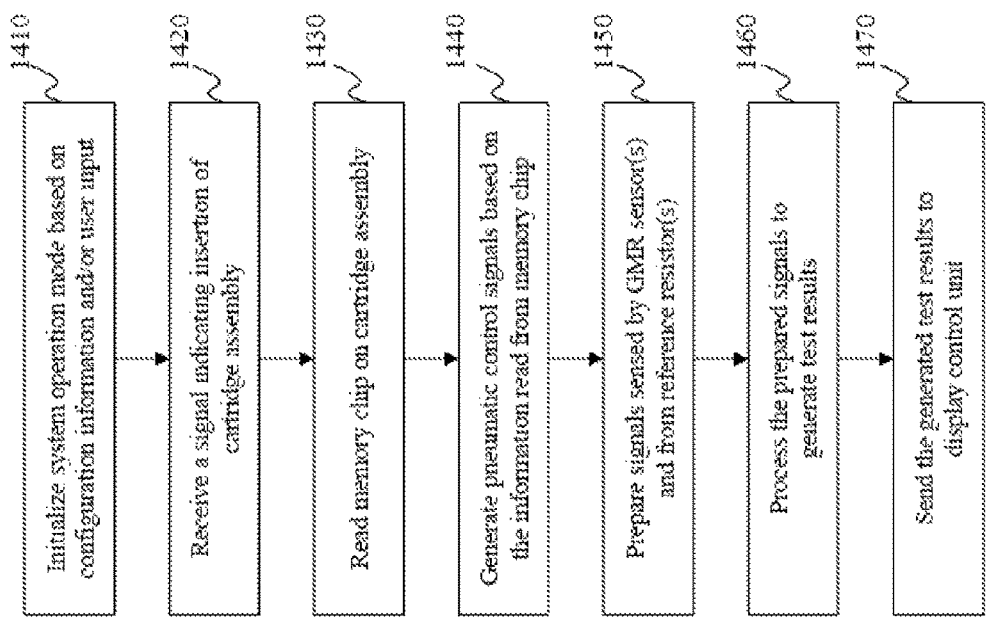
FIG. 29 is a flowchart of a process of the cartridge reader, in accordance with an embodiment of this disclosure.

FIG. 29 is a flowchart of the process of the cartridge reader 310 in accordance with an embodiment. As shown in FIG. 29, the cartridge reader 310 starts its operation at step 1410 by initializing an operation mode based on system configuration profile and/or instructions inputted by the user via the user interface 140. Then, the process waits at step 1420 for a signal indicating that a cartridge assembly 200 has been inserted into the cartridge reader 310. This signal may be created by either the cartridge assembly 200 or the cartridge reader 310 upon recognition of the insertion. In response to receiving such a signal, at step 1430, the cartridge reader 310 reads the memory chip 275 on the cartridge assembly 200. Then, at step 1440, the cartridge reader 310 generates control signals based on the read information, and sending them to the pneumatic system 330 for pneumatic control used in preparation of the sample to be tested. At step 1450, the cartridge reader 310 prepares measurement signals at the GMR sensors and at the at least one reference resistor and receives the signals. Then, at step 1460, the cartridge reader 310 processes the received measurement signals to generate test results. Finally, at step 1470, the cartridge reader 310 sends the generated test results to the display control unit 120 for display to the user.

Figure 30:
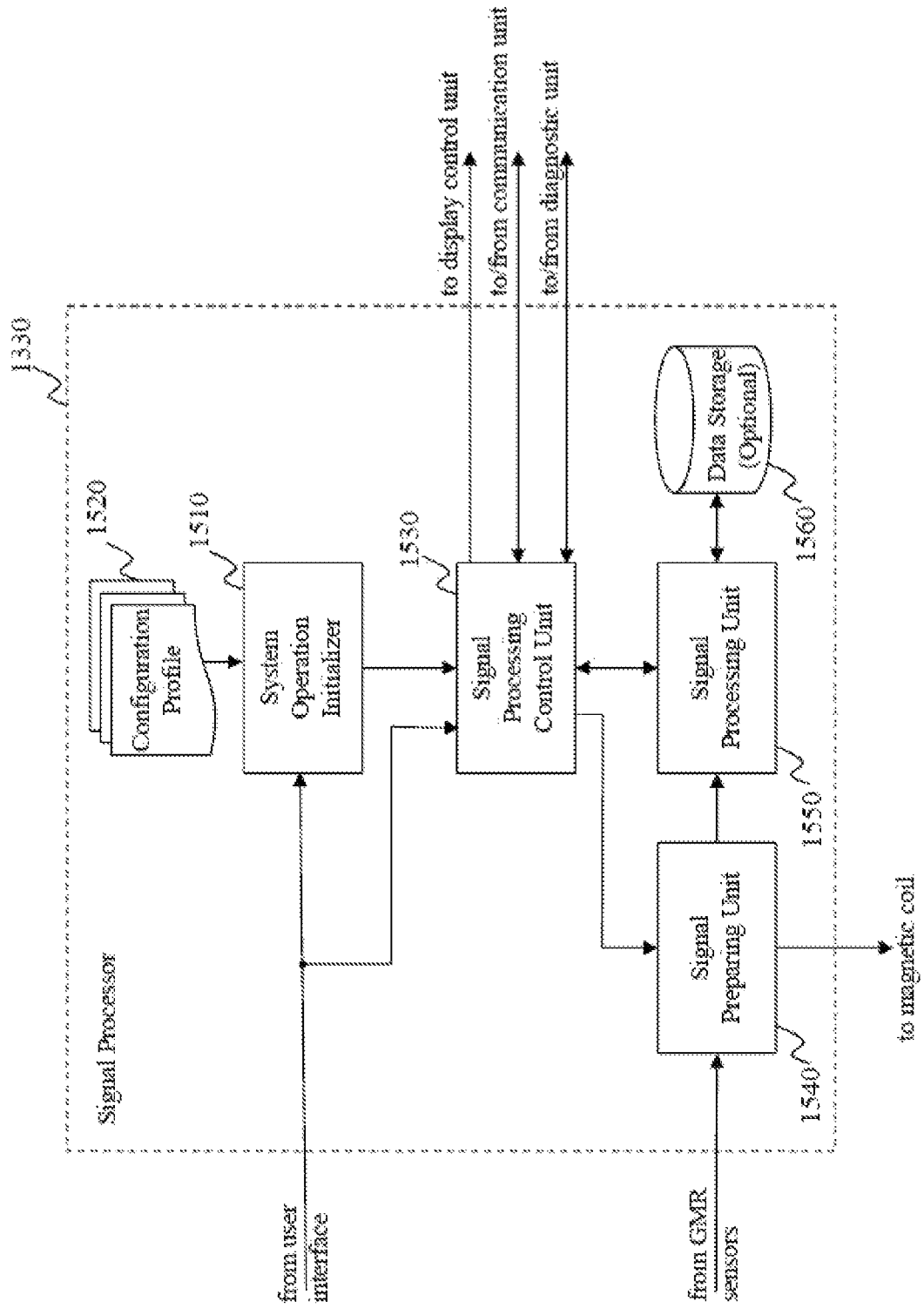
FIG. 30 schematically shows functional blocks of a signal processor, in accordance with an embodiment of this disclosure.

FIG. 30 schematically shows the functional blocks of the signal processor 1330 in accordance with an embodiment. As shown in FIG. 30, the signal processor 1330 may include a system operation initializer 1510, a configuration profile 1520, a signal processing control unit 1530, a signal preparing unit 1540, a signal processing unit 1550 and an optional data storage 1560. The system operation initializer 1510 may be configured to, based on system configuration information read from the configuration profile 1520 and/or instructions received via the user interface 140, set up a system operation environment and initialize the functions of the signal processor 1330, in particular those of the signal processing control unit 1530. The signal processing control unit 1530 operates to generate control signals for controlling the signal preparing unit 1540 and the signal processing unit 1550, for example. It may also operate to control display of the detection results via the display control unit 120 on a display, and to control communication of data between the signal processing control unit 1550 and the communication unit 340 and/or the diagnostic unit 350. The signal preparing unit 1540 may be configured to, under the control of the signal processing control unit 1530, prepare measurement circuits, excite an AC magnetic field applied to the GMR sensors and create carrier signal applied to the measurement circuits, collect measurement signals from the measurement circuits, and feed the measurement signals after amplification and analog-to-digital-conversion to the signal processing unit 1550, in accordance with embodiments. The signal processing unit 1550 may be configured to process the received measurement signals by analytically solving for detection results, and send the detection results to the signal processing control unit 1530. Additionally, in some embodiments, the result data may be stored in the optional data storage 1560.

Figure 31:
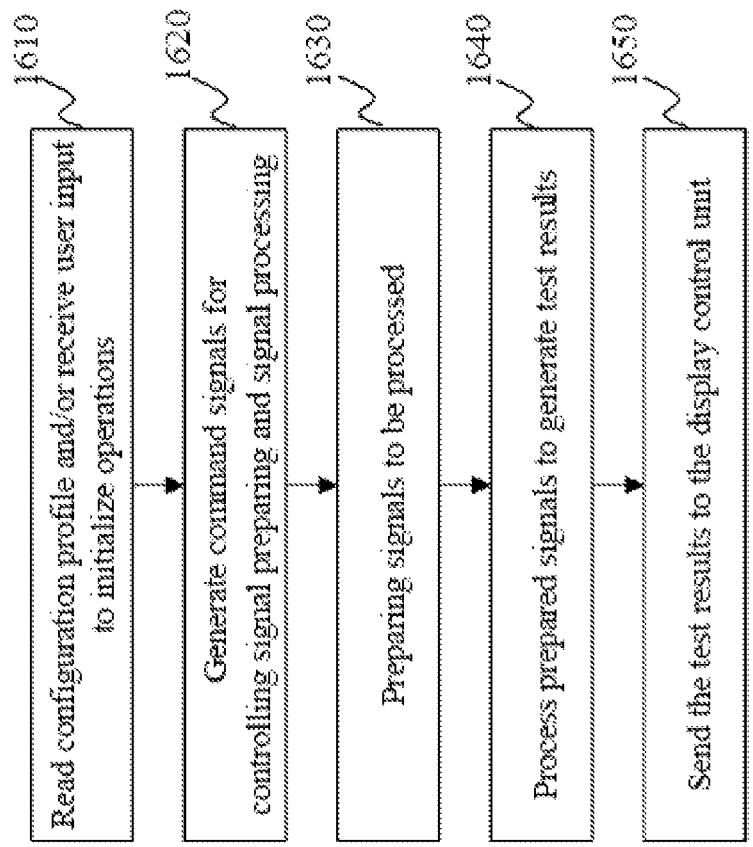
FIG. 31 is a flowchart of the process for the signal processor as noted in FIG. 30, in accordance with an embodiment of this disclosure.

FIG. 31 is a flowchart of the process for the signal processor 1330 in accordance with an embodiment. As shown in FIG. 31, the process starts at step 1610 by reading system configuration information from the configuration profile and/or receiving user instructions via the user interface 140 to initialize the system operation environment. Then, at step 1620, a series of control signals are generated by the signal processing control unit 1530 for administrating the operations of the signal preparing unit 1540 and the signal processing unit 1550. At step 1630, measurement circuits are built up by the signal preparing unit 1540 based on the control signals from the signal processing control unit 1530, so as to prepare measurement signals from the GMR sensors and the at least one reference resistor. Then, at step 1640, the prepared measurement signals are processed by the signal processing unit 1550 to solve for test results of the analyte detection. Finally, at step 1650, the generated test results are sent from the signal processing unit 1550 to the display control unit 120 for display to the user.

In accordance with an embodiment, there is provided a cartridge assembly for preparing a test sample and sensing analytes therein using a sensor. The cartridge assembly includes: a sample processing card having: an injection port for receiving the test sample within a body of the card; at least one metering chamber for receiving the test sample; a mixing material source for introducing one or more mixing materials to the at least one metering chamber; fluid communication channels fluidly connecting the injection port and the mixing material source to the at least one metering chamber; and at least one output port fluidly connected to the at least one metering chamber for delivering the test sample and the one or more mixing materials to the sensor. The cartridge assembly also includes a substrate attached to the sample processing card. The substrate has associated therewith: the sensor for sensing analytes in the test sample, the sensor being configured to receive the test sample and the one or more mixing materials via the at least one output port; electrical contact portions configured to establish an electrical connection with the reader unit; and a memory chip for storing information related to processing of the test sample within the sample processing card. The cartridge assembly further includes a pneumatic interface comprising at least one pneumatic control port and corresponding communication channel fluidly connected to the at least one metering chamber, the pneumatic interface configured for connection to an off-board pneumatic system of a reader unit, the pneumatic interface configured to enable application of positive and negative pressurized fluid to the sample processing card to move the test sample and one or more mixing materials therein. The memory chip may store a pneumatic system protocol that includes steps and settings for selectively applying pressure to the pneumatic interface and thus delivering at least the test sample from the sample processing card to the sensor.

In some embodiments, the sample processing card further comprises one or more waste chambers therein, the one or more waste chambers being fluidly connected to either the at least one metering chamber, an input port from the sensor, or both, via one or more communication channels.

In some embodiments, the sample processing card further comprises a gas permeable membrane fluidly connected to the at least one metering chamber, wherein the gas permeable membrane is configured to receive and deliver atmospheric air into the sample processing card.

In some embodiments, the sample processing card further comprises at least one mixing channel for mixing the test sample and the one or more mixing materials into a substantially homogeneous mixture, the mixing channel being selectively connected to the at least one metering chamber and configured to deliver the substantially homogeneous mixture to the sensor via the at least one output port.

In some embodiments, the at least one mixing channel comprises a stepped configuration relative to a longitudinal axis of the sample processing card.

In some embodiments, a vent port may be provided in the sample processing card, wherein the vent port is open to atmosphere and configured to vent air from the sample processing card.

In some embodiments, the sample processing card further comprises a filtration membrane for filtering the test sample injected into the injection port.

In some embodiments, the mixing material source is one or more of: a blister pack, a storage chamber, a cartridge, and a well.

In some embodiments, the one or more mixing materials comprises one or more of: a reagent, a buffer, and a beads solution.

In some embodiments, the sample processing card further comprises a plurality of valves therein, the plurality of valves being connected to the communication channels within the sample processing card and each of the valves being configured for movement between an open position and a closed position to thereby open fluid communication to a connected communication channel and close fluid communication to a connected communication channel, respectively. In some embodiments, each valve comprises an elastomeric deflection portion configured for movement between the open and closed positions. In some embodiments, the pneumatic interface further comprises one or more valve control ports configured to deliver pressurized air to one or more of the plurality of valves, to move the one or more plurality of valves between the open position and the closed position.

In some embodiments, the sensor comprises a giant magnetoresistance (GMR) sensor.

In some embodiments, the substrate comprises a printed circuit board configured to establish communication between the sensor, the electrical contact pads, and memory chip when the electrical connection is established with the reader unit.

In some embodiments, the substrate comprises a laminated layer applied to the sample processing card.

In some embodiments, the pneumatic interface is provided on the sample processing card. In some embodiments, the at least one pneumatic control port is provided on a top surface of the sample processing card.

In some embodiments, alignment devices for alignment of the cartridge assembly with the reader unit.

In some embodiments, a serpentine channel is provided in the sample processing card of the cartridge assembly, the serpentine channel being connected to the mixing channel.

In some embodiments, the sample processing card comprises layers, and wherein the at least one metering chamber and the mixing material source are provided on a same layer.

In some embodiments, the sample processing card comprises layers, and wherein the at least one metering chamber is provided on a separate layer as compared to the mixing material source.

In some embodiments, the sample processing card comprises layers, and wherein the at least one metering chamber is provided on a separate layer as compared to the one or more waste chambers.

In some embodiments, the sample processing card comprises layers, and wherein the at least one metering chamber and the filtration membrane are provided on a same layer.

In some embodiments, the sample processing card comprises layers, and wherein the at least one metering chamber and the plurality of valves are provided on a same layer.

In some embodiments, the sample processing card comprises layers, and wherein the one or more waste chambers and the plurality of valves are provided on a same layer.

In some embodiments, has a heater provided on the substrate.

In some embodiments, a method of using the cartridge assembly comprises: injecting the test sample into the injection port; establishing the electrical connection with the reader unit; and selectively applying pressurized air to the pneumatic interface using the off-board pneumatic system to move the test sample and the one or more mixing materials within the communication channels and to the sensor.

While the principles of the disclosure have been made clear in the illustrative embodiments set forth above, it will be apparent to those skilled in the art that various modifications may be made to the structure, arrangement, proportion, elements, materials, and components used in the practice of the disclosure.

It will thus be seen that the features of this disclosure have been fully and effectively accomplished. It will be realized, however, that the foregoing preferred specific embodiments have been shown and described for the purpose of illustrating the functional and structural principles of this disclosure and are subject to change without departure from such principles. Therefore, this disclosure includes all modifications encompassed within the spirit and scope of the following claims.

What is claimed is:

1. A cartridge assembly for preparing a test sample and sensing analytes therein using a sensor, the cartridge assembly comprising:
   a sample processing card comprising:
      an injection port for receiving the test sample within a body of the card;
      at least one metering chamber for receiving the test sample injected into the injection port;
      a mixing material source for introducing one or more mixing materials to the at least one metering chamber;
      fluid communication channels fluidly connecting the injection port and the mixing material source to the at least one metering chamber; and at least one output port, fluidly connected to the at least one metering chamber via channels, for delivering the test sample and the one or more mixing materials to the sensor;

and a substrate attached to the sample processing card, the substrate having associated therewith:
  the sensor for sensing analytes in the test sample, the sensor being configured to receive the test sample and the one or more mixing materials via the at least one output port of the sample processing card;
  electrical contact portions configured to establish an electrical connection with a reader unit; and
  a memory chip for storing information related to processing of the test sample within the sample processing card;

wherein the cartridge assembly further comprises a pneumatic interface comprising at least one pneumatic control port and a corresponding communication channel fluidly connected to the at least one metering chamber of the sample processing card, the pneumatic interface configured for connection to an off-board pneumatic system of the reader unit, the pneumatic interface configured to enable application of positive and negative pressurized fluid to the sample processing card to move the test sample and one or more mixing materials within the fluid communication channels and to the sensor, and wherein the memory chip stores a pneumatic system protocol configured to selectively applying pressure to the pneumatic interface upon connection with the reader unit and thus delivering at least the test sample from the sample processing card to the sensor.

2. The cartridge assembly according to claim 1, wherein the sample processing card further comprises one or more waste chambers therein, the one or more waste chambers being fluidly connected to either the at least one metering chamber, an input port from the sensor, or both, via one or more communication channels.

3. The cartridge assembly according to claim 2, wherein the sample processing card comprises layers that are stacked vertically on one another, and wherein the at least one metering chamber is provided on a separate layer as compared to the mixing material source and/or the one or more waste chambers.

4. The cartridge assembly according to claim 1, wherein the sample processing card further comprises a gas permeable membrane fluidly connected to the at least one metering chamber, wherein the gas permeable membrane is configured to receive and deliver atmospheric air into the sample processing card via the fluid communication channels, and wherein the fluid communication channels are provided in the body below the gas permeable membrane and the at least one metering chamber.

5. The cartridge assembly according to claim 1, wherein the sample processing card further comprises at least one mixing channel for mixing the test sample and the one or more mixing materials into a substantially homogeneous mixture, the at least one mixing channel being connected to the at least one metering chamber via a connecting channel extending therebetween and configured to deliver the substantially homogeneous mixture to the sensor via the at least one output port.

6. The cartridge assembly according to claim 5, wherein the at least one mixing channel comprises a stepped configuration between a first end and a second end thereof relative to a longitudinal axis of the sample processing card, the stepped configuration including alternating first portions and second portions, the first portions extending longitudinally in a longitudinal direction and the second portions extending laterally relative to the longitudinal axis of a housing of the sample processing card.

7. The cartridge assembly according to claim 5, further comprising a serpentine channel therein extending longitudinally in a longitudinal direction of the sample processing card, the serpentine channel being connected to the at least one mixing channel and configured to direct the test sample to the sensor.

8. The cartridge assembly according to claim 1, further comprising a vent port in the sample processing card, wherein the vent port is open to atmosphere and configured to vent air from the sample processing card.

9. The cartridge assembly according to claim 1, wherein the sample processing card further comprises a filtration membrane for filtering the test sample injected into the injection port to produce a filtered test sample, wherein the at least one metering chamber is configured to receive the filtered test sample.

10. The cartridge assembly according to claim 9, wherein the sample processing card further comprises a plurality of valves therein, the plurality of valves being connected to the fluid communication channels within the sample processing card and each of the valves being configured for movement between an open position and a closed position to thereby open fluid communication to a connected fluid communication channel and close fluid communication to a connected communication channel, respectively.

11. The cartridge assembly according to claim 10, wherein each valve comprises an elastomeric deflection portion configured for movement between the open and closed positions.

12. The cartridge assembly according to claim 10, wherein the pneumatic interface further comprises one or more valve control ports configured to deliver pressurized air to one or more of the plurality of valves, to move the one or more plurality of valves between the open position and the closed position.

13. The cartridge assembly according to claim 10, wherein the sample processing card comprises layers that are stacked vertically on one another, and wherein the at least one metering chamber is provided on a same layer as one or more of the group consisting of: the mixing material source, the filtration membrane, and the plurality of valves.

14. The cartridge assembly according to claim 1, wherein the sensor comprises a giant magnetoresistance (GMR) sensor.

15. The cartridge assembly according to claim 1, wherein the substrate comprises a printed circuit board configured to establish communication between the sensor, the electrical contact portions, and memory chip when the electrical connection is established with the reader unit.

16. The cartridge assembly according to claim 1, wherein the substrate comprises a laminated layer applied to the sample processing card.

17. The cartridge assembly according to claim 1, wherein the pneumatic interface is provided on the sample processing card.

18. The cartridge assembly according to claim 1, further comprising alignment devices for alignment of the cartridge assembly with the reader unit.

19. The cartridge assembly according to claim 1, further comprising a heater provided on the substrate.

20. A method of using the cartridge assembly according to claim 1 with the reader unit having the pneumatic system; the method comprising:

injecting the test sample into the injection port;

establishing the electrical connection with the reader unit; and selectively applying pressurized air to the pneumatic interface using the pneumatic system to move the test sample and the one or more mixing materials within the fluid communication channels and to the sensor.

* * * * *